US012578349B2

(12) United States Patent     (10) Patent No.:   US 12,578,349 B2

Gorin et al.           (45) Date of Patent:     Mar. 17, 2026

(54) BLOOD TESTING SYSTEM AND METHOD

(71) Applicant: CA CASYSO GmbH, Basel (CH)

(72) Inventors: Michael M. Gorin, Incline Village, NV (US); Robert S. Hillman, San Diego, CA (US); Cory Lee McCluskey, Encinitas, CA (US); Hubert Martin Schwaiger, Munich (DE)

(73) Assignee: CA CASYSO GmbH, Basel (CH)

( * ) Notice: Subject to any disclaimer, the term of this patent is extended or adjusted under 35 U.S.C. 154(b) by 1342 days.

(21) Appl. No.: 17/030,115

(22) Filed: Sep. 23, 2020

(65) Prior Publication Data

US 2021/0003597 A1     Jan. 7, 2021

Related U.S. Application Data

(60) Division of application No. 14/958,889, filed on Dec. 3, 2015, now Pat. No. 10,816,559, which is a continuation-in-part of application No. 14/500,248, filed on Sep. 29, 2014, now Pat. No. 10,175,225.

(51) Int. Cl.
    *G01N 33/86*        (2006.01)
    *G01N 33/49*        (2006.01)

(52) U.S. Cl.
    CPC ......... *G01N 33/86* (2013.01); *G01N 33/4905* (2013.01)

(58) Field of Classification Search
    CPC ........................... G01N 33/86; G01N 33/4905
    See application file for complete search history.

(56) References Cited

U.S. PATENT DOCUMENTS

| | | | |
|---|---|---|---|
| 2,555,937 | A | 6/1951 | Rosenthal et al. |
| 2,995,425 | A | 8/1961 | Hans |
| 3,714,815 | A | 2/1973 | Hartert |
| 3,803,903 | A | 4/1974 | Lin |
| 3,903,903 | A | 9/1975 | Matsumura |
| 4,112,740 | A | 9/1978 | Brandestini |
| 4,148,216 | A | 4/1979 | Do et al. |
| 4,193,293 | A | 3/1980 | Cavallari |
| D260,428 | S | 8/1981 | Fekete |
| 4,319,194 | A | 3/1982 | Cardinal et al. |
| 4,443,408 | A | 4/1984 | Mintz |

(Continued)

FOREIGN PATENT DOCUMENTS

| | | | |
|---|---|---|---|
| AU | 2011237383 B2 | 10/2012 | |
| CN | 1816306 A | 8/2006 | |

(Continued)

OTHER PUBLICATIONS

Cimbala, J., "Introduction to Pressure in Fluid Mechanics," Learning Module, The Pennsylvania State University, [online] Retrieved from the Internet <URL:https://www.me.psu.edu/cimbala/Learning/Fluid/Pressure/pressure_basics. htm> [retrieved on Jan. 22, 2024], 3 pages.

(Continued)

*Primary Examiner* — Samuel P Siefke

(74) *Attorney, Agent, or Firm* — ArentFox Schiff LLP

(57) ABSTRACT

Some embodiments of a blood coagulation testing system include an analyzer console device and a single-use cartridge component configured to releasably install into the console device. In some embodiments, the blood coagulation testing system can operate as an automated thromboelastometry system that is particularly useful, for example, at a point-of-care site.

34 Claims, 17 Drawing Sheets

(56) References Cited

U.S. PATENT DOCUMENTS

| | | | |
|---|---|---|---|
| 4,558,589 A | 12/1985 | Hemmes et al. |
| 4,599,219 A | 7/1986 | Cooper et al. |
| 4,671,939 A | 6/1987 | Mintz |
| 4,695,956 A | 9/1987 | Leveen et al. |
| 4,705,756 A | 11/1987 | Spillert et al. |
| 4,726,220 A | 2/1988 | Feier et al. |
| 4,752,449 A | 6/1988 | Jackson et al. |
| 4,753,776 A | 6/1988 | Hillman et al. |
| 4,756,884 A | 7/1988 | Hillman et al. |
| 4,765,180 A | 8/1988 | Clifton |
| 4,767,600 A | 8/1988 | Vicario |
| 4,814,247 A | 3/1989 | Spillert et al. |
| D302,294 S | 7/1989 | Hillman |
| 4,849,340 A | 7/1989 | Oberhardt |
| 4,852,577 A | 8/1989 | Smith et al. |
| 4,868,129 A | 9/1989 | Gibbons et al. |
| D305,360 S | 1/1990 | Fechtner |
| 4,900,679 A | 2/1990 | Spillert et al. |
| 4,948,961 A | 8/1990 | Hillman et al. |
| 4,956,089 A | 9/1990 | Hurst |
| 4,963,498 A | 10/1990 | Hillman et al. |
| 5,009,316 A | 4/1991 | Klein |
| 5,016,469 A | 5/1991 | Henderson |
| 5,028,142 A | 7/1991 | Ostoich et al. |
| 5,056,357 A | 10/1991 | Dymling et al. |
| 5,077,017 A | 12/1991 | Gorin et al. |
| 5,091,304 A | 2/1992 | La Duca et al. |
| 5,104,813 A | 4/1992 | Besemer et al. |
| 5,104,975 A | 4/1992 | McCormick et al. |
| D327,743 S | 7/1992 | Frenkel et al. |
| 5,162,237 A | 11/1992 | Messenger et al. |
| 5,164,598 A | 11/1992 | Hillman et al. |
| 5,165,237 A | 11/1992 | Athey et al. |
| 5,169,786 A | 12/1992 | Caroll et al. |
| 5,204,525 A | 4/1993 | Hillman et al. |
| 5,205,159 A | 4/1993 | Carr, Jr. |
| 5,207,988 A | 5/1993 | Lucas |
| 5,222,808 A | 6/1993 | Sugarman et al. |
| 5,223,219 A | 6/1993 | Subramanian et al. |
| 5,223,227 A | 6/1993 | Zuckerman |
| 5,234,839 A | 8/1993 | McCormick et al. |
| 5,273,517 A | 12/1993 | Barone et al. |
| 5,287,732 A | 2/1994 | Sekiguchi |
| 5,300,779 A | 4/1994 | Hillman et al. |
| 5,302,348 A | 4/1994 | Cusack et al. |
| D347,067 S | 5/1994 | Shartle et al. |
| 5,311,908 A | 5/1994 | Barone et al. |
| 5,331,964 A | 7/1994 | Trahey et al. |
| 5,372,946 A | 12/1994 | Cusack et al. |
| 5,378,431 A | 1/1995 | Vogler et al. |
| 5,447,440 A | 9/1995 | Davis et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,531,102 A | 7/1996 | Brookfield et al. |
| 5,534,226 A | 7/1996 | Gavin et al. |
| 5,602,037 A | 2/1997 | Ostgaard et al. |
| 5,605,154 A | 2/1997 | Ries et al. |
| 5,606,971 A | 3/1997 | Sarvazyan et al. |
| 5,628,961 A | 5/1997 | Davis et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,660,993 A | 8/1997 | Cathey et al. |
| 5,673,699 A | 10/1997 | Trahey et al. |
| 5,731,212 A | 3/1998 | Gavin et al. |
| 5,744,898 A | 4/1998 | Smith et al. |
| 5,763,199 A | 6/1998 | Coller |
| 5,777,212 A | 7/1998 | Sekiguchi et al. |
| 5,777,215 A | 7/1998 | Calatzis et al. |
| 5,788,928 A | 8/1998 | Carey et al. |
| 5,800,781 A | 9/1998 | Gavin et al. |
| 5,810,731 A | 9/1998 | Sarvazyan et al. |
| 5,854,005 A | 12/1998 | Coller |
| 5,854,076 A | 12/1998 | Kundu et al. |
| 5,854,423 A | 12/1998 | Venegas |
| 5,888,826 A | 3/1999 | Ostgaard et al. |
| 5,899,861 A | 5/1999 | Friemel et al. |
| 5,902,937 A | 5/1999 | Amrani et al. |
| 5,921,928 A | 7/1999 | Greenleaf et al. |
| 5,922,551 A | 7/1999 | Durbin et al. |
| 5,922,591 A | 7/1999 | Anderson et al. |
| 5,952,560 A | 9/1999 | Collings et al. |
| 6,012,712 A | 1/2000 | Bernstein |
| 6,016,712 A | 1/2000 | Warden et al. |
| 6,033,546 A | 3/2000 | Ramsey |
| 6,039,691 A | 3/2000 | Walker et al. |
| 6,046,051 A | 4/2000 | Jina |
| 6,066,243 A | 5/2000 | Anderson et al. |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen-Bacrie et al. |
| 6,197,595 B1 | 3/2001 | Anderson et al. |
| 6,200,532 B1 | 3/2001 | Wu et al. |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lane et al. |
| 6,242,267 B1 | 6/2001 | Herron et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,318,191 B1 | 11/2001 | Chen |
| 6,371,912 B1 | 4/2002 | Nightinggale et al. |
| 6,398,956 B1 | 6/2002 | Coville et al. |
| 6,402,704 B1 | 6/2002 | McMorrow |
| 6,403,381 B1 | 6/2002 | Mann et al. |
| 6,412,344 B1 | 7/2002 | Danicich et al. |
| 6,413,782 B1 | 7/2002 | Parce et al. |
| 6,429,025 B1 | 8/2002 | Parce et al. |
| 6,436,722 B1 | 8/2002 | Clark et al. |
| 6,448,024 B1 | 9/2002 | Bruegger |
| 6,451,610 B1 | 9/2002 | Gorman et al. |
| 6,454,714 B1 | 9/2002 | Ng et al. |
| 6,479,299 B1 | 11/2002 | Parce et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,555,381 B2 | 4/2003 | Baugh et al. |
| 6,573,104 B2 | 6/2003 | Carr, Jr. et al. |
| 6,613,286 B2 | 9/2003 | Braun et al. |
| 6,613,573 B1 | 9/2003 | Cohen |
| D481,133 S | 10/2003 | Blouin et al. |
| 6,632,678 B2 | 10/2003 | Aiken et al. |
| D482,454 S | 11/2003 | Gebrian |
| 6,662,031 B1 | 12/2003 | Khalil et al. |
| 6,670,133 B2 | 12/2003 | Knapp et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,699,718 B1 | 3/2004 | Bruegger |
| 6,716,168 B2 | 4/2004 | Nock et al. |
| 6,726,629 B1 | 4/2004 | Frinking et al. |
| 6,750,053 B1 | 6/2004 | Widrig Opalsky et al. |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,830,936 B2 | 12/2004 | Anderson et al. |
| 6,838,055 B2 | 1/2005 | Sando et al. |
| 6,890,299 B2 | 5/2005 | Cohen et al. |
| 6,942,836 B2 | 9/2005 | Freudenthal et al. |
| 6,951,127 B1 | 10/2005 | Bi |
| 6,951,544 B2 | 10/2005 | Trahey et al. |
| 6,979,569 B1 | 12/2005 | Carver et al. |
| 7,005,857 B2 | 2/2006 | Stiene et al. |
| 7,132,078 B2 | 11/2006 | Rawson |
| 7,179,652 B2 | 2/2007 | Cohen et al. |
| 7,192,726 B1 | 3/2007 | Carr, Jr. et al. |

(56) References Cited

U.S. PATENT DOCUMENTS

| | | | |
|---|---|---|---|
| 7,202,048 | B2 | 4/2007 | Carr, Jr. |
| 7,205,115 | B2 | 4/2007 | McHugh et al. |
| 7,207,939 | B2 | 4/2007 | Husher |
| 7,247,488 | B2 | 7/2007 | Ghai et al. |
| 7,258,411 | B2 | 8/2007 | Parce et al. |
| 7,261,861 | B2 | 8/2007 | Kautzky |
| 7,374,538 | B2 | 5/2008 | Nightingale et al. |
| 7,399,637 | B2 | 7/2008 | Wright et al. |
| 7,412,877 | B1 | 8/2008 | Bi |
| 7,419,638 | B2 | 9/2008 | Saltsman et al. |
| 7,422,905 | B2 | 9/2008 | Clague et al. |
| 7,439,069 | B2 | 10/2008 | Nippoldt et al. |
| 7,491,175 | B2 | 2/2009 | Ruether et al. |
| 7,497,997 | B2 | 3/2009 | Glezer et al. |
| 7,524,670 | B2 | 4/2009 | Cohen et al. |
| 7,595,169 | B2 | 9/2009 | Swaim et al. |
| 7,674,616 | B2 | 3/2010 | Farnam, III et al. |
| 7,732,213 | B2 | 6/2010 | Cohen et al. |
| 7,745,223 | B2 | 6/2010 | Schubert et al. |
| 7,790,362 | B2 | 9/2010 | Coller et al. |
| 7,811,792 | B2 | 10/2010 | Cohen et al. |
| 7,842,234 | B2 | 11/2010 | Lauks et al. |
| 7,892,188 | B2 | 2/2011 | Walker et al. |
| 7,897,114 | B2 | 3/2011 | Poissy et al. |
| 7,901,629 | B2 | 3/2011 | Calatzis et al. |
| 7,912,661 | B2 | 3/2011 | Zeng et al. |
| 7,938,573 | B2 | 5/2011 | Gau et al. |
| 7,939,288 | B2 | 5/2011 | Wrabetz et al. |
| 7,947,505 | B2 | 5/2011 | Kawasaki et al. |
| 7,951,606 | B2 | 5/2011 | Pei et al. |
| 7,959,875 | B2 | 6/2011 | Zhou et al. |
| 7,972,271 | B2 | 7/2011 | Johnson et al. |
| 7,976,795 | B2 | 7/2011 | Zhou et al. |
| 8,003,401 | B2 | 8/2011 | Tonnessen et al. |
| D645,973 | S | 9/2011 | Hoenes |
| 8,017,382 | B2 | 9/2011 | Davis et al. |
| 8,058,023 | B2 | 11/2011 | Gurbel |
| 8,062,883 | B2 | 11/2011 | Woudenberg et al. |
| 8,067,226 | B2 | 11/2011 | Woudenberg et al. |
| 8,084,272 | B2 | 12/2011 | Campbell et al. |
| 8,110,392 | B2 | 2/2012 | Battrell et al. |
| 8,168,442 | B2 | 5/2012 | Petersen et al. |
| 8,202,492 | B2 | 6/2012 | Linder et al. |
| 8,216,526 | B2 | 7/2012 | Locascio et al. |
| 8,222,024 | B2 | 7/2012 | Davis et al. |
| 8,238,182 | B2 | 8/2012 | Bond et al. |
| 8,318,109 | B2 | 11/2012 | Saltsman et al. |
| 8,372,343 | B2 | 2/2013 | Goldstein |
| 8,377,392 | B2 | 2/2013 | Miller et al. |
| 8,383,045 | B2 | 2/2013 | Schubert et al. |
| 8,409,527 | B2 | 4/2013 | Linder et al. |
| 8,431,413 | B2 | 4/2013 | Dority et al. |
| 8,448,499 | B2 | 5/2013 | Schubert et al. |
| 8,475,737 | B2 | 7/2013 | Linder et al. |
| 8,548,759 | B2 | 10/2013 | Walker et al. |
| 8,574,828 | B2 | 11/2013 | Coller et al. |
| 8,591,448 | B2 | 11/2013 | Powers et al. |
| 8,591,829 | B2 | 11/2013 | Taylor et al. |
| 8,697,009 | B2 | 4/2014 | Saltsman et al. |
| 8,709,787 | B2 | 4/2014 | Handique |
| 8,740,818 | B2 | 6/2014 | Walker et al. |
| 8,765,062 | B2 | 7/2014 | Linder et al. |
| 8,802,445 | B2 | 8/2014 | Linder et al. |
| 8,857,244 | B2 | 10/2014 | Schubert et al. |
| 8,883,510 | B2 | 11/2014 | Gehring et al. |
| 8,932,523 | B2 | 1/2015 | Linder et al. |
| 9,061,280 | B2 | 6/2015 | Tanaami et al. |
| 9,062,342 | B2 | 6/2015 | Carrera Fabra et al. |
| 9,063,121 | B2 | 6/2015 | Gilbert et al. |
| 9,068,966 | B2 | 6/2015 | Delmenico et al. |
| 9,075,047 | B2 | 7/2015 | Linder et al. |
| 9,086,423 | B2 | 7/2015 | Schubert et al. |
| 9,110,084 | B2 | 8/2015 | Schubert et al. |
| D737,993 | S | 9/2015 | Tan et al. |
| 9,238,223 | B2 | 1/2016 | Handique |
| 9,272,280 | B2 | 3/2016 | Viola et al. |
| 9,285,377 | B2 | 3/2016 | Schubert et al. |
| 9,341,637 | B2 | 5/2016 | Coller et al. |
| 9,354,243 | B2 | 5/2016 | Chapman et al. |
| 9,410,971 | B2 | 8/2016 | Viola et al. |
| 9,506,938 | B2 | 11/2016 | Coller et al. |
| D777,343 | S | 1/2017 | Gorin et al. |
| 9,739,789 | B2 | 8/2017 | Schubert et al. |
| 9,915,671 | B2 | 3/2018 | Schubert et al. |
| 9,977,039 | B2 | 5/2018 | Viola et al. |
| 10,023,897 | B2 | 7/2018 | Mori et al. |
| 10,031,144 | B2 | 7/2018 | Viola et al. |
| 10,175,225 | B2 | 1/2019 | McCluske et al. |
| 10,481,168 | B2 | 11/2019 | Viola et al. |
| 10,746,750 | B2 | 8/2020 | Schubert et al. |
| 10,843,185 | B2 | 11/2020 | Gorin et al. |
| 11,061,038 | B2 | 7/2021 | Schubert et al. |
| 11,131,680 | B2 | 9/2021 | Schubert et al. |
| 11,360,106 | B2 | 6/2022 | Schubert et al. |
| 11,879,899 | B2 | 1/2024 | Schubert et al. |
| 11,892,459 | B2 | 2/2024 | Schubert et al. |
| 2001/0046685 | A1 | 11/2001 | Moskowitz et al. |
| 2002/0013530 | A1 | 1/2002 | Cespedes et al. |
| 2002/0040187 | A1 | 4/2002 | Alam et al. |
| 2002/0081741 | A1 | 6/2002 | Braun et al. |
| 2002/0177958 | A1 | 11/2002 | Widrig Opalsky et al. |
| 2003/0013958 | A1 | 1/2003 | Govari et al. |
| 2003/0073244 | A1 | 4/2003 | Cohen et al. |
| 2003/0105398 | A1 | 6/2003 | Vitek |
| 2003/0113929 | A1 | 6/2003 | Baugh et al. |
| 2003/0170883 | A1 | 9/2003 | Martin et al. |
| 2003/0171676 | A1 | 9/2003 | Trahey et al. |
| 2003/0199082 | A1 | 10/2003 | Miller |
| 2003/0204141 | A1 | 10/2003 | Nock et al. |
| 2004/0053351 | A1 | 3/2004 | Fischer et al. |
| 2004/0065143 | A1 | 4/2004 | Husher |
| 2004/0068184 | A1 | 4/2004 | Trahey et al. |
| 2004/0072278 | A1 | 4/2004 | Chou et al. |
| 2004/0072357 | A1 | 4/2004 | Stiene et al. |
| 2004/0076546 | A1 | 4/2004 | Bissett |
| 2004/0088317 | A1 | 5/2004 | Fabrick et al. |
| 2004/0089616 | A1 | 5/2004 | Kellogg et al. |
| 2004/0131500 | A1 | 7/2004 | Chow |
| 2004/0167403 | A1 | 8/2004 | Nightingale et al. |
| 2004/0189311 | A1 | 9/2004 | Glezer et al. |
| 2004/0200909 | A1 | 10/2004 | McMillan et al. |
| 2004/0203163 | A1 | 10/2004 | Cohen et al. |
| 2004/0214337 | A1 | 10/2004 | Kautzky |
| 2005/0004463 | A1 | 1/2005 | Chen et al. |
| 2005/0015001 | A1 | 1/2005 | Lec et al. |
| 2005/0053305 | A1 | 3/2005 | Li et al. |
| 2005/0123447 | A1 | 6/2005 | Koike et al. |
| 2005/0136541 | A1 | 6/2005 | De Haan |
| 2005/0148899 | A1 | 7/2005 | Walker et al. |
| 2005/0164373 | A1 | 7/2005 | Oldham et al. |
| 2005/0215901 | A1 | 9/2005 | Anderson et al. |
| 2005/0216987 | P1 | 9/2005 | Murakami |
| 2005/0220668 | A1 | 10/2005 | Coville |
| 2005/0233460 | A1 | 10/2005 | Clague et al. |
| 2005/0233466 | A1 | 10/2005 | Wright et al. |
| 2007/0036679 | A1 | 2/2007 | Munenaka |
| 2007/0038095 | A1 | 2/2007 | Greenleaf et al. |
| 2007/0059208 | A1 | 3/2007 | Desmond |
| 2007/0059840 | A1 | 3/2007 | Cohen et al. |
| 2007/0078631 | A1 | 4/2007 | Ariyoshi et al. |
| 2007/0099290 | A1 | 5/2007 | Iida et al. |
| 2007/0105236 | A1 | 5/2007 | Chang et al. |
| 2007/0140902 | A1 | 6/2007 | Calatzis et al. |
| 2007/0184508 | A1 | 8/2007 | Cohen et al. |
| 2007/0243105 | A1 | 10/2007 | Kratzer et al. |
| 2007/0243632 | A1 | 10/2007 | Coller et al. |
| 2007/0245810 | A1 | 10/2007 | Carter et al. |
| 2007/0259348 | A1 | 11/2007 | Phadke et al. |
| 2007/0266778 | A1 | 11/2007 | Corey et al. |
| 2007/0276236 | A1 | 11/2007 | Jong |
| 2008/0026476 | A1 | 1/2008 | Howell et al. |
| 2008/0038828 | A1 | 2/2008 | Cohen et al. |
| 2008/0160500 | A1 | 7/2008 | Fuller et al. |
| 2008/0194041 | A1 | 8/2008 | Guirguis |

(56) References Cited

U.S. PATENT DOCUMENTS

| | | |
|---|---|---|
| 2008/0194967 A1 | 8/2008 | Sliwa et al. |
| 2008/0200343 A1 | 8/2008 | Clemens |
| 2008/0227217 A1 | 9/2008 | Yamamoto et al. |
| 2008/0249408 A1 | 10/2008 | Palmeri et al. |
| 2008/0251383 A1 | 10/2008 | Sobek et al. |
| 2008/0261261 A1 | 10/2008 | Grimes et al. |
| 2008/0280285 A1 | 11/2008 | Chen et al. |
| 2008/0297169 A1 | 12/2008 | Greenquist et al. |
| 2008/0299587 A1 | 12/2008 | Durbin |
| 2009/0112483 A1 | 4/2009 | Cohen |
| 2009/0130645 A1 | 5/2009 | Schubert et al. |
| 2009/0181411 A1 | 7/2009 | Battrell et al. |
| 2009/0269837 A1 | 10/2009 | Shevkoplyas et al. |
| 2009/0305315 A1 | 12/2009 | Gandola et al. |
| 2010/0056383 A1 | 3/2010 | Ririe et al. |
| 2010/0104474 A1 | 4/2010 | Van Haag et al. |
| 2010/0154520 A1 | 6/2010 | Schubert |
| 2010/0184201 A1 | 7/2010 | Schubert et al. |
| 2010/0190193 A1 | 7/2010 | Calatzis et al. |
| 2010/0274130 A1 | 10/2010 | Anand et al. |
| 2010/0294767 A1 | 11/2010 | Catteau et al. |
| 2010/0317538 A1 | 12/2010 | Seki et al. |
| 2011/0034805 A1 | 2/2011 | Walker et al. |
| 2011/0151491 A1 | 6/2011 | Dennis et al. |
| 2011/0172661 A1 | 7/2011 | Designer et al. |
| 2011/0201099 A1 | 8/2011 | Anderson et al. |
| 2011/0237913 A1 | 9/2011 | Schubert et al. |
| 2011/0252352 A1 | 10/2011 | Viola et al. |
| 2012/0043202 A1 | 2/2012 | Miyamura et al. |
| 2012/0084022 A1 | 4/2012 | Giovangrandi et al. |
| 2012/0232803 A1 | 9/2012 | Viola et al. |
| 2012/0244392 A1 | 9/2012 | Kleiman |
| 2012/0252127 A1 | 10/2012 | Gregor et al. |
| 2012/0294767 A1 | 11/2012 | Viola et al. |
| 2012/0329082 A1 | 12/2012 | Viola et al. |
| 2013/0137172 A1 | 5/2013 | Ririe et al. |
| 2013/0190584 A1 | 7/2013 | Walker et al. |
| 2013/0270113 A1 | 10/2013 | Huang |
| 2013/0323846 A1 | 12/2013 | Schubert et al. |
| 2013/0323847 A1 | 12/2013 | Schubert et al. |
| 2013/0323848 A1 | 12/2013 | Schubert et al. |
| 2013/0333448 A1 | 12/2013 | Schubert et al. |
| 2014/0004613 A1 | 1/2014 | Goldstein |
| 2014/0234859 A1 | 8/2014 | Coller et al. |
| 2014/0271409 A1 | 9/2014 | Knight et al. |
| 2014/0328732 A1 | 11/2014 | Delmenico et al. |
| 2015/0132860 A1 | 5/2015 | Cook et al. |
| 2015/0253271 A1 | 9/2015 | Giridhar et al. |
| 2015/0260735 A1 | 9/2015 | Delmenico et al. |
| 2015/0316460 A1 | 11/2015 | Redl |
| 2016/0032355 A1 | 2/2016 | Zaman et al. |
| 2016/0091415 A1 | 3/2016 | Gorin |
| 2016/0091483 A1 | 3/2016 | McCluskey et al. |
| 2016/0091509 A1 | 3/2016 | Di Tullio et al. |
| 2016/0091511 A1 | 3/2016 | Di Tullio et al. |
| 2016/0091514 A1 | 3/2016 | Gorin et al. |
| 2016/0091515 A1 | 3/2016 | Gorin et al. |
| 2016/0091516 A1 | 3/2016 | Gorin et al. |
| 2016/0091517 A1 | 3/2016 | Gorin et al. |
| 2016/0139159 A1 | 5/2016 | Viola et al. |
| 2016/0195557 A1 | 7/2016 | Schubert et al. |
| 2016/0313357 A1 | 10/2016 | Viola et al. |
| 2016/0361715 A1 | 12/2016 | Shi et al. |
| 2016/0377638 A1 | 12/2016 | Bels et al. |
| 2017/0097367 A1 | 4/2017 | Schubert et al. |
| 2017/0254318 A1 | 9/2017 | Lee et al. |
| 2018/0133714 A1 | 5/2018 | Wo et al. |
| 2018/0306774 A1 | 10/2018 | Viola et al. |
| 2021/0172966 A1 | 6/2021 | Schubert et al. |
| 2021/0341499 A1 | 11/2021 | Schubert et al. |

FOREIGN PATENT DOCUMENTS

| | | |
|---|---|---|
| CN | 1853104 A | 10/2006 |
| CN | 1985168 A | 6/2007 |
| CN | 101035479 A | 9/2007 |
| CN | 101195112 A | 6/2008 |
| CN | 101301632 A | 11/2008 |
| CN | 100540145 | 9/2009 |
| CN | 101563562 A | 10/2009 |
| CN | 102265151 | 11/2011 |
| CN | 103170377 A | 6/2013 |
| CN | 103175950 A | 6/2013 |
| CN | 103217401 A | 7/2013 |
| CN | 104204787 A | 12/2014 |
| CN | 104903728 A | 9/2015 |
| CN | 103649751 B | 3/2017 |
| DE | 2740932 A1 | 11/1978 |
| DE | 10135569 A1 | 2/2003 |
| DE | 202014002289 U1 | 9/2014 |
| EP | 0404456 A2 | 12/1990 |
| EP | 1162457 A2 | 12/2001 |
| EP | 1347058 A2 | 9/2003 |
| EP | 1367392 A1 | 12/2003 |
| EP | 1367392 B1 | 12/2003 |
| EP | 1394546 A1 | 3/2004 |
| EP | 1627725 A2 | 2/2006 |
| EP | 1884778 A1 | 2/2008 |
| EP | 1901065 A1 | 3/2008 |
| EP | 2208996 A1 | 7/2010 |
| EP | 2202517 B1 | 8/2012 |
| EP | 2555704 B1 | 2/2013 |
| EP | 2676143 A2 | 12/2013 |
| EP | 3001196 A2 | 3/2016 |
| EP | 3001196 B1 | 9/2018 |
| GB | 2257256 A | 1/1993 |
| JP | 1971-004947 A | 11/1971 |
| JP | S5550162 | 4/1980 |
| JP | 1987-140047 A | 6/1987 |
| JP | H01140047 A | 6/1987 |
| JP | 1991-031764 A | 2/1991 |
| JP | H04-32767 | 2/1992 |
| JP | H09-504372 | 4/1997 |
| JP | 1997-159596 A | 6/1997 |
| JP | 09-507580 A | 7/1997 |
| JP | 2001258868 | 9/2001 |
| JP | 2001-516880 A | 10/2001 |
| JP | 2005-164296 | 6/2005 |
| JP | 2005-534895 A | 11/2005 |
| JP | 2006-053142 A | 2/2006 |
| JP | 2007-051881 A | 3/2007 |
| JP | 2007517221 A | 6/2007 |
| JP | 2007-532878 A | 11/2007 |
| JP | 2008-503722 A | 2/2008 |
| JP | 2008-302322 A | 12/2008 |
| JP | 2010-078575 A | 4/2010 |
| JP | 2010-078608 | 8/2010 |
| JP | 2010-266453 A | 11/2010 |
| JP | 2011-174952 A | 9/2011 |
| JP | 2012-042426 A | 3/2012 |
| JP | 2012-513582 A | 6/2012 |
| JP | 2012-515340 A | 7/2012 |
| JP | 2013-524176 A | 6/2013 |
| JP | 2014-010109 A | 1/2014 |
| JP | 2015-045642 A | 3/2015 |
| JP | 2015-516583 | 6/2015 |
| JP | 2016-118530 | 6/2016 |
| JP | 2016-118530 A | 6/2016 |
| WO | WO 1989/006803 A1 | 7/1989 |
| WO | 96/03870 A1 | 2/1996 |
| WO | WO 96/38730 A1 | 12/1996 |
| WO | 97/41432 A1 | 11/1997 |
| WO | WO 1999/014595 A1 | 3/1999 |
| WO | 200250535 A1 | 6/2002 |
| WO | WO 2002/050535 A1 | 6/2002 |
| WO | WO 2002/063273 A2 | 8/2002 |
| WO | 2005026690 | 3/2005 |
| WO | 2005106467 A1 | 11/2005 |
| WO | WO 2006/091650 A2 | 8/2006 |
| WO | WO 2006/126290 A1 | 11/2006 |
| WO | WO 2006/137334 A1 | 12/2006 |
| WO | WO 2007/047961 A2 | 4/2007 |
| WO | 2008/047875 A1 | 4/2008 |
| WO | WO 2008/075181 A2 | 6/2008 |

(56)                    References Cited

FOREIGN PATENT DOCUMENTS

| | | | |
|---|---|---|---|
| WO | WO 2008/093216 A1 | 8/2008 |
| WO | WO 2009/073851 A1 | 6/2009 |
| WO | 2009152094 A2 | 12/2009 |
| WO | WO 2010/072620 A1 | 7/2010 |
| WO | 2011035162 A1 | 3/2011 |
| WO | WO 2011/117017 A1 | 9/2011 |
| WO | 2011120556 | 10/2011 |
| WO | 2011127436 A2 | 10/2011 |
| WO | 2012159021 A2 | 11/2012 |
| WO | 2013105987 A2 | 7/2013 |
| WO | WO 2013/172003 A1 | 11/2013 |
| WO | WO 2014/115478 A1 | 7/2014 |
| WO | WO 2014/162285 A1 | 10/2014 |
| WO | WO 2014/172243 A1 | 10/2014 |
| WO | 2015095658 | 6/2015 |
| WO | 2016/118530 A1 | 7/2016 |
| WO | 2016196236 | 12/2016 |
| WO | WO 2014/103744 A1 | 1/2017 |
| WO | 2017096284 | 6/2017 |
| WO | WO 2017/096284 A1 | 6/2017 |

OTHER PUBLICATIONS

Extended European Search Report in Application No. 23201178.3 dated Jan. 31, 2024, 11 pages.
Non-Final Office Action in U.S. Appl. No. 18/212,002 dated Feb. 6, 2024, 9 pages.
Reply to Office Action in U.S. Appl. No. 18/089,505, filed Feb. 6, 2024, 12 pages.
Notification of Reasons for Refusal in Japanese Application No. 2023-082050 dated Mar. 22, 2024 [with English translation], 5 pages.
Office Action in Ex Parte Reexamination of U.S. Pat. No. 11,061,038, issued Apr. 26, 2022, (37 pages).
Examination Report in Australian Application No. 2022201777 dated May 16, 2023, 2 pages.
Action and Response History in U.S. Appl. No. 17/393,036, downloaded on Oct. 31, 2023, 60 pages.
Action and Response History in U.S. Appl. No. 16/572,567, downloaded on Oct. 31, 2023, 97 pages.
Action and Response History in U.S. Appl. No. 90/019,098, downloaded on Oct. 31, 2023, 233 pages.
Action and Response History in U.S. Appl. No. 18/089,505, downloaded on Oct. 31, 2023, 18 pages.
Non-Final Office Action in U.S. Appl. No. 18/211,917 dated Oct. 31, 2023, 14 pages.
Reply to Non-Final Office Action in U.S. Appl. No. 18/211,917 dated Dec. 5, 2023,4 pages.
Action and Response History in U.S. Appl. No. 16/708,334, downloaded on Oct. 31, 2023, 56 pages.
Order Granting Request For Ex Parte Reexamination of U.S. Pat. No. 11,061,038, issued Dec. 10. 2021, 15 pages.
Paper 10, Scheduling Order for IPR2021-00293 of U.S. Pat. No. 10,746,750, issued Jul. 11, 2021, 11 pages.
Paper 9, Decision Granting Institution of Inter Partes Review under 35 U.S.C. § 314 for IPR2021-00293 of U.S. Pat. No. 10,746,750, issued Jul. 1, 2021, 29 pages,.
Patent Owner's Response to Petition under 37 C.F.R. §42.120 for IPR2021-00293 of U.S. Pat. No. 10,746,750, filed Sep. 24, 2021, 24 pages.
Patent Owner's Preliminary Response for IPR2021-00293 of U.S. Pat. No. 10,746,750, filed Apr. 22, 2021, 6 pages.
Petitioner's Reply to Patent Owner's Response under 37 C.F.R. §42.120 for IPR2021-00293 of U.S. Pat. No. 10,746,750, filed Dec. 16, 2021, 30 pages.
Exhibit 1004. Response to Non-Final Office Action for IPR2021-00293 of U.S. Patent No. U.S. Appl. No. 16/146,333, filed Dec. 19, 2019, 10 pages.
Exhibit 2001. Statutory Terminal Disclaimer for IPR2021-00293 of U.S. Pat. No. 10,746,750, filed Apr. 22, 2021, 3 pages.

Exhibit 1031, Paper 21, Patent Owner's Sur-Reply for IPR2018-00950 of U.S. Pat. No. 9,915,671, filed May 6, 2019, 34 pages.
Exhibit 1030, Paper 19, Petitioner's Reply to Patent Owner's Response for IPR2018-00950 of U.S. Pat. No. 9,915,671, filed Apr. 4, 2019, 32 pages.
Exhibit 2003, Definition of "Duct" retrieved from Dictionary.com., for IPR2021-00293 of U.S. Pat. No. 10,746,750, filed Apr. 22, 2021, 8 pages.
Exhibit 1032, Request for Rehearing for IPR2018-00950 of U.S. Pat. No. 9,915,671, filed Nov. 1, 2019, 15 pages.
Exhibit 1029, Patent Owner's Response for IPR2018-00950 of U.S. Pat. No. 9,915,671, filed Jan. 4, 2019, 37 pages,.
Request for Ex Parte Reexamination of U.S. Pat. No. 11,061,038 Filed by a Third Party Requester November 3. 2021, 341 pages.
Appendix A of Request for Ex Parte Reexamination of U.S. Pat. No. 11,061,038 filed by a Third Party Requester, November 3. 2021, 102 pages.
Appendix B of Request for Ex Parte Reexamination of U.S. Pat. No. 11,061,038 filed by a Third Party Requester, November 3. 2021, 112 pages.
Appendix C of Request for Ex Parte Reexamination of U.S. Pat. No. 11,061,038 filed by a Third Party Requester, November 3. 2021, 126 pages.
Appendix D of Request for Ex Parte Reexamination of U.S. Pat. No. 11,061,038 filed by a Third Party Requester, November 3. 2021, 139 pages.
Exhibit 1001. U.S. Pat. No. 11,061,038, issued Jul. 13, 2021, of Request for Ex Parte Reexamination filed by a Third Party Requester, Nov. 3, 2021, 39 pages.
Exhibit 1002. File History of U.S. Pat. No. 11,061,038, issued Jul. 13, 2021, of Request for Ex Parte Reexamination filed by a Third Party Requester, Nov. 3, 2021, 417 pages.
Exhibit 1003. PTAB-IPR2018-00950 Declaration of Scott L. Diamond, of Request for Ex Parte Reexamination filed by a Third Party Requester, Nov. 3, 2021, 201 pages.
Exhibit 1004. U.S. Pat. No. 5,629,209, issued May 13, 1977, of Request for Ex Parte Reexamination filed by a Third Party Requester, Nov. 3, 2021, 39 pages.
Exhibit 1005. PTAB-IPR2018-00950 Lang 2006 (German), of Request for Ex Parte Reexamination filed by a Third Party Requester, Nov. 3, 2021, 14 pages.
Exhibit 1006. PTAB-IPR2018-00950 Lang 2006 (certified English translation), of Request for Ex Parte Reexamination filed by a Third Party Requester, Nov. 3, 2021, 28 pages.
Exhibit 1007. PTAB-IPR2018-00950 Lang 2006 (Supplemental English translation), of Request for Ex Parte Reexamination filed by a Third Party Requester, Nov. 3, 2021, 10 pages.
Exhibit 1008. IPR2021-00293 Statutory Disclaimer, of Request for Ex Parte Reexamination filed by a Third Party Requester, Nov. 3, 2021, 4 pages.
Exhibit 1009. U.S. Pat. No. 6,016,712, issued Jan. 25, 2000, of Request for Ex Parte Reexamination filed by a Third Party Requester, Nov. 3, 2021, 24 pages.
Exhibit 1010. U.S. Pat. No. 9,915,671, issued May 13, 2018, of Request for Ex Parte Reexamination filed by a Third Party Requester, Nov. 3, 2021, 25 pages.
Exhibit 1011. IPR2018-00950 Final Written Decision (Paper 30), of Request for Ex Parte Reexamination filed by a Third Party Requester, Nov. 3, 2021, 50 pages.
Exhibit 1012. IPR2021-00293 Petition for IPR of U.S. Pat. No. 10,746,750 (Paper 2), of Request for Ex Parte Reexamination filed by a Third Party Requester, Nov. 3, 2021, 80 pages.
Exhibit 1013. IPR2021-00293 Trial Instituted Decision (Paper 9), of Request for Ex Parte Reexamination filed by a Third-Party Requester, Nov. 3, 2021, 30 pages.
Exhibit 1014. IPR2018-00950 Petition for IPR of U.S. Pat. No. 9,915,671 (Paper 2), of Request for Ex Parte Reexamination filed by a Third-Party Requester, Nov. 3, 2021, 77 pages.
Exhibit 1015. IPR2018-00950 Patent Owner's Response (Paper 13), of Request for Ex Parte Reexamination filed by a Third-Party Requester, Nov. 3, 2021, 38 pages.

(56) References Cited

OTHER PUBLICATIONS

Exhibit 1016. IPR2018-00950 General Order (Paper 34), of Request for Ex Parte Reexamination filed by a Third-Party Requester, Nov. 3, 2021, 7 pages.

Exhibit 1017. IPR2021-00293 Patent Owner's Response (Paper 11), of Request for Ex Parte Reexamination filed by a Third-Party Requester, Nov. 3, 2021, 25 pages.

Exhibit 1018. Dictionary.com online dictionary—cavity; ductwork; duct, of Request for Ex Parte Reexamination filed by a Third-Party Requester, Nov. 3, 2021, 22 pages.

Exhibit 1019. IPR2018-00950 Petitioner's Reply to Patent Owner's Response (Paper 19), of Request for Ex Parte Reexamination filed by a Third-Party Requester, Nov. 3, 2021, 33 pages.

Exhibit 1020. U.S. Patent Publication No. 2005220668A1, published Oct. 6, 2005, of Request for Ex Parte Reexamination filed by a Third Party Requester, Nov. 3, 2021, 18 pages.

Exhibit 1021. U.S. Pat. No. 6,613,286, Issued Sep. 2, 2003, of Request for Ex Parte Reexamination filed by a Third Party Requester, Nov. 3, 2021, 20 pages.

Exhibit 1022. U.S. Patent Publication No. 20040189311A1, published Sep. 30, 2004, of Request for Ex Parte Reexamination filed by a Third Party Requester, Nov. 3, 2021, 91 pages.

Exhibit 1023. U.S. Patent Publication No. 20050233460A1, published Oct. 20, 2005, of Request for Ex Parte Reexamination filed by a Third Party Requester, Nov. 3, 2021, 32 pages.

Exhibit 1024. Straub et al., of Request for Ex Parte Reexamination filed by a Third Party Requester, Nov. 3, 2021, 8 pages.

Transmittal of Request for Ex Parte Reexamination of U.S. Pat. No. 11,061,038 Filed by a Third Party Requester Nov. 3, 2021, 3 pages.

Electronic Acknowledgment Receipt of Request for Ex Parte Reexamination of U.S. Pat. No. 11,061,038 Filed by a Third Party Requester Nov. 3, 2021, 7 pages.

Information Disclosure Statement accompanying Request for Ex Parte Reexamination of U.S. Pat. No. 11,061,038 Filed by a Third Party Requester Nov. 3, 2021, 2 pages.

Non Final Office Action dated Jan. 14, 2021, U.S. Appl. No. 17/343,960, filed Jun. 10, 2021 (11 pages).

Coiffic et al., "Inhibition of platelet aggregation by abciximab but not by aspirin can be detected by a new point-of-care test, the Hemostatus, " Thromb. Res. 95(2), pp. 83-91 (1999) [9 pages].

Fitch et al., "Point-of-care and standard laboratory coagulation testing during cardiovascular surgery: balancing reliability and timeliness," J. Clin. Monit. Comp., vol. 15, pp. 197-204 (1999) [8 pages].

Hoffman et al., "A cell-based model of hemostasis," Thromb. Haemost 2001; 85:958-65 (2001).

Holmes et al., "Novel, Bedside, Tissue Factor-Dependent Clotting Assay Permits Improved Assessment of Combination Antithrombotic and Antiplatelet Therapy," Circulation, vol. 102, pp. 2051-2057 (2000).

Huissoud et al., "Coagulation assessment by rotation thrombelastometry in normal pregnancy," Thromb. Haemostat., vol. 101, pp. 755-761 (2009).

Libgot-Calle et al., "High Frequency Ultrasound Device to Investigate the Acoustic Properties of Whole Blood During Coagulation," Ultrasound Med. Biol. 34.2, pp. 252-264, (2008).

Mauldin et al., "Adaptive force sonorheometry for assessment of whole blood coagulation," Clin. Chim. Acta. Int. J. Clin. Chem., 411.9-10 pp. 638-644 (2010).

Riegger et al., "Teflon-carbon black as new material for the hydrophobic patterning of polymer labs-on-a-chip," TRANSDUCERS 2009—15th International Conference on Solid-State Sensors, Actuators and Microsystems, pp. 2026-2029, DOI: 10.1109/SENSOR. 2009.5285661 (2009).

Rumbaut et al., "Chapter 4: Platelet Aggregation," Excerpt from Platelet-Vessel Wall Interactions in Hemostasis and Thrombosis, Morgan & Claypool Life Sciences (pub.), San Rafael, CA, 5 pages (2010).

Schocl et al., "Use of Rotation Thromboelastometry (ROTEM®) to Achieve Successful Treatment of Polytrauma with Fibrinogen Concentrate and Prothrombin Complex Concentrate," Anaesthesia, J. Assoc. Anaes. of Great Britain and Ireland, vol. 65, pp. 199-203 (2010).

Sinn et al., "Platelet aggregation monitoring with a newly developed quartz crystal microbalance system as an alternative to optical platelet aggregometry," Analyst, vol. 135, pp. 2930-2938 (2010).

Theusinger et al., "Rotation thromboelastometry (ROTEM) stability and reproducibility over time," Eur. J. Cardio-Thor. Surg. 37.3, pp. 677-683 (2009).

Tucci et al., "Platelet function monitoring with the Sonoclot analyzer after in vitro tirofiban heparin administration," J. Thor. Cardiovasc. Surg. 131.6, pp. 1314-1322 (2006).

Venema et al., "An assessment of clinical interchangeability of TEG and ROTEM thromboelastographic variables in cardiac surgical patients," Anesth. Analg. 111.2:339-344 (2010).

Webster, J. (ed.), [Excerpt] Medical Instrumentation: Application and Design, New York: John Wiley & Sons, 696 pages (2010). Fourth Edition.

Certificate of Correction for Patent No. 10,031,144 filed on Apr. 24, 2019, Exhibit 1003 to PGR2019-00047.

Certificate of Correction for Patent No. 9,977,039 filed on Feb. 21, 2019, Exhibit 1003 to PGR2019-00033.

Decision Denying Institution of Post-Grant Review filed on Aug. 23, 2019 for PGR2019- 00033, 26 pgs.

Decision Denying Institution of Post-Grant Review filed on Oct. 24, 2019 for PGR2019- 00047, 29 pages.

Decision Denying Petitioner's Request for Rehearing filed on Nov. 8, 2019 for U.S. Pat. No. 9,977,093 [PGR2019-00033], 13 pages.

Email from Trials@USPTO.gov Gabriel Goldman on Jun. 5, 2019, Exhibit 1015 to PGR2019- 00033, 5 pages.

Final Written Decision filed on Apr. 24, 2019, Exhibit 1028/ 1029 to PGR2019-00047.

Final Written Decision filed on Feb. 21, 2019, Exhibits 1011 and 1012 to PGR2019- 00033.

Gabriel Goldman email to the Patent Trial and Appeal Board on Jun. 3, 2019, Exhibit 1014 to PGR2019-00033, 3 pages.

Patent Owner's Notice of Appeal filed on Feb. 4, 2020 for IPR2018-00950.

Request for Rehearing and Request to Enter New Exhibits filed on Sep. 22, 2019 for PGR2019-00033, 21 pages.

Table of Prior Art Devices filed on Feb. 3, 2017 [Exhibit 1010 to IPR2017-00852].

Official Notice of Rejection in Japanese Patent Application No. 2021-210802 dated Jan. 17, 2023 (with English translation), 9 pages.

Communication pursuant to Article 94(3) EPC in Application No. 20175351.4 dated Mar. 13, 2023, 5 pages.

Communication pursuant to Article 94(3) EPC in Application No. 18193752.5 dated Mar. 1, 2023, 5 pages.

European Search Report in corresponding application No. 20175351.4 dated Sep. 21, 2020 (8 pages).

Extended European Search Report in EP Application No. 13167979. 7, dated Nov. 6, 2013, 5 pages.

Extended European Search Report in EP Application No. 13163014. 7, dated May 23, 2013, 3 pages.

Extended European Search Report in EP Application No. 12179576. 9, dated Oct. 5, 2012, 5 pages.

Extended European Search Report in EP Application No. 08172769.5 dated Jun. 4, 2009, 11 pages.

Office Action in Chinese Application No. 201680074338.9, dated Feb. 3, 2019, 4 pages (w/out English translation).

Action and Response History in U.S. Appl. No. 12/640,376 [now U.S. Pat. No. 8,448,499], 47 pages.

Action and Response History in U.S. Appl. No. 13/895,034 [now U.S. Pat. No. 9,285,377], 42 pages.

Action and Response History in U.S. Appl. No. 15/066,605 [now U.S. Pat. No. 9,739,789], 38 pages.

Action and Response History in U.S. Appl. No. 15/357,492 [now U.S. Pat. No. 9,915,671], 177 pages.

Action and Response History in U.S. Appl. No. 15/869,782, 17 pages.

Action and Response History in U.S. Appl. No. 16/146,333 [now U.S. Pat. No. 10,746,750], 165 pages.

(56)                References Cited

OTHER PUBLICATIONS

Action and Response History in U.S. Appl. No. 16/520,006 [now U.S. Pat. No. 11,131,680], 143 pages.
Action and Response History in U.S. Appl. No. 16/520,004 [now U.S. Pat. No. 10,996,230], 114 pages.
Action and Response History in U.S. Appl. No. 17/182,502 [now U.S. Pat. No. 11,061,038], 51 pages.
Action and Response History in U.S. Appl. No. 17/372,637 [now U.S. Pat. No. 11,360,106], 64 pages.
Action and Response History in U.S. Appl. No. 17/393,036, 45 pages.
Action and Response History in U.S. Appl. No. 17/831,845, 24 pages.
Action and Response History in U.S. Appl. No. 18/089,505, 12 pages.
Action and Response History in U.S. Appl. No. 14/500,248 [now U.S. Pat. No. 10,175,225], 77 pages.
Action and Response History in U.S. Appl. No. 14/958,876 [now U.S. Pat. No. 10,288,630], 65 pages.
Action and Response History in U.S. Appl. No. 14/958,878 [now U.S. Pat. No. 10,539,579], 80 pages.
Action and Response History in U.S. Appl. No. 14/958,889 [now U.S. Pat. No. 10,816,559], 137 pages.
Action and Response History in U.S. Appl. No. 14/958,890 [now U.S. Pat. No. 9,897,618], 42 pages.
Action and Response History in U.S. Appl. No. 16/201,522 [now U.S. Pat. No. 11,327,069], 108 pages.
Action and Response History in U.S. Appl. No. 16/708,334, 34 pages.
Action and Response History in U.S. Appl. No. 17/343,960, 105 pages.
Action and Response History in U.S. Appl. No. 16/572,567, 85 pages.
Action and Response History in U.S. Appl. No. 15/648,345 [now U.S. Pat. No. 10,843,185], 58 pages.
Action and Response History in U.S. Appl. No. 15/904,984 [now U.S. Pat. No. 10,481,168], 238 pages.
Action and Response History in U.S. Appl. No. 15/991,677 [now U.S. Pat. No. 10,161,944], 41 pages.
Action and Response History in U.S. Appl. No. 15/202,059 [now U.S. Pat. No. 10,031,144], 162 pages.
Action and Response History in U.S. Appl. No. 15/644,124 [now U.S. Pat. No. 9,977,039], 142 pages.
Action and Response History in U.S. Patent Reexam U.S. Appl. No. 90/019,032, 570 pages.
Action and Response History in U.S. Patent Reexam U.S. Appl. No. 90/019,098, 213 pages.
Action and Response History in U.S. Appl. No. 13/397,398 [now U.S. Pat. No. 9,272,280], 221 pages.
Japanese Notice of Rejection dated Jul. 20, 2021, Application No. 2019-215835 (8 pgs.).
Communication under Article 94(3) EPC for European patent application No. 20175351.4, issued Feb. 15, 2022, with English Summary, (4 pages).
Notification of Reasons for Refusal for Japanese Patent Application No. 2021-143317, issued Aug. 30, 2022, (with English translation) 4 pages.
Straub, Andreas, et al. "Using reagent-supported thromboelastometry (ROTEMW) to monitor haemostatic changes in congenital head surgery employing deep hypothermic circulatory arrest" European Journal of Cardio-thoracic Surgery 34 (2008) 641-647. Year: 2008).
Non-Final Office Action received in U.S. Application. No. U.S. Appl. No. 17/182,502, dated Apr. 14, 2021, (12 pages).
Examination Report No. 1 issued in Australian Application No. 2021200600, dated Mar. 17, 2021, 5 pages.
Extended European Search Report in Application No. 24157405.2 dated May 14, 2024, 10 pages.
Non-Final Office Action in Ex Parle Reexamination for U.S. Appl. No. 90/019,098, issued Dec. 19, 2022, (12 pages).

Straub, Andreas, et al., "Using reagent-supported thromboelastometry (ROTEMW) to monitor haemostatic changes in congenital heart surgery employing deep hypothemic circulatory arrest," European Journal of Cardio-thoracic Surgery 34 (2008) 641-647. (Year: 2008).
Non-Final Office Action dated Nov. 2, 2021, U.S. Appl. No. 17/372,637, filed Jul. 12, 2021 (19 pages).
Non-Final Office Action for U.S. Appl. No. 17/343,960, issued Aug. 30, 2022, 9 pages,.
Request for Ex Parte Reexamination by third Party Requestor of U.S. Pat. No. 10,175,225, filed Jul. 15, 2022, (124 pages).
Exhibit 1001: U.S. Pat. No. 10,175,225 Mccluskey et al., ("the '225 Patent") for Request for Ex Parte Reexamination of U.S. Pat. No. 10,175,225, filed Jul. 15, 2022, 35 pages.
Exhibit 1002: Prosecution History of the '225 Patent for Request for Ex Parte Reexamination of U.S. Pat. No. 10,175,225, filed Jul. 15, 2022, 1,670 pages.
Exhibit 1003: U.S. Patent Application Publication No. 2005/0220668 to Coville ("Coville") for Request for Ex Parte Reexamination of U.S. Pat. No. 10,175,225, filed Jul. 15, 2022, 17 pages.
Exhibit 1004: U.S. Publication No. 2015/0260735 to Delmenico et al. ("Delmenico") for Request for Ex Parte Reexamination of U.S. Pat. No. 10,175,225, filed Jul. 15, 2022, 11 pages.
Exhibit 1005: Lang T. and von Depka M., "Diagnostische Möglichkeiten und Grenzen der Thrombelastographie/- graphie" (Possibilities and Limitations of Thromboelastometry/-graph). Hämostaseologie, Aug. 26, 2006; (3 Supplemental 1): $20-9 ("Lang 2006") (German) for Request for Ex Parte Reexamination of U.S. Pat. No. 10,175,225, filed Jul. 15, 2022, 13 pages.
Exhibit 1006: Lang T. and von Depka M., "Possibilities and Limitations of Thrombelastrometry/-graphy,". Hämostaseologie, Aug. 26, 2006; (3 Supplemental 1): S20-9 ("Lang 2006") (Certified English Translation of German Version) for Request for Ex Parte Reexamination of U.S. Pat. No. 10,175,225, filed Jul. 15, 2022, 27 pages.
Exhibit 1007: Lang T. and von Depka M., "Possibilities and Limitations of Thrombelastrometry/-graphy,". Hämostaseologie, Aug. 26, 2006; (3 Supplemental 1): S20-9 ("Lang 2006") (Supplemental English Translation published online by Journal Hämostaseologie) for Request for Ex Parte Reexamination of U.S. Pat. No. 10,175,225, filed Jul. 15, 2022, 9 pages.
Exhibit 1008: U.S. Publication No. 2010/0154520 to Schubert et al. ("Schubert") for Request for Ex Parte Reexamination of U.S. Pat. No. 10,175,225, filed Jul. 15, 2022, 20 pages.
Exhibit 1009: Final Written Decision, Hemosonics LLC v. C.A. Casyso GMBH, Case IPR2021-00293, Paper 18, (Jun. 21, 2022) for Request for Ex Parte Reexamination of U.S. Pat. No. 10,175,225, filed Jul. 15, 2022, 32 pages.
Exhibit 1010: U.S. Publication No. 2012/0329082 to Viola et al. ("Viola") for Request for Ex Parte Reexamination of U.S. Pat. No. 10,175,225, filed Jul. 15, 2022, 28 pages.
Exhibit 1011: U.S. Publication No. 2010/0190193 to Calatziz et al. ("Calatziz") for Request for Ex Parte Reexamination of U.S. Pat. No. 10, 175,225, filed Jul. 15, 2022, 13 pages.
Exhibit 1012: Final Written Decision, Hemosonics LLC v. C.A. Casyso GMBH, Case IPR2018-00950, Paper 30 (Oct. 2, 2019) for Request for Ex Parte Reexamination of U.S. Pat. No. 10,175,225, filed Jul. 15, 2022, 49 pages.
Exhibit 1013: Decision Denying Rehearing, Hemosonics LLC v. C.A. Casyso GMBH, Case IPR2018-00950, Paper 32 (Dec. 5, 2019) for Request for Ex Parte Reexamination of U.S. Pat. No. 10,175,225, filed Jul. 15, 2022, 12 pages,.
Exhibit 1014: Judgement Affirming PTAB, C.A. Casyso GMBH v. Hemosonics LLC, Appeal No. 2020-1444 (Fed. Cir. Jun. 13, 2022) for Request for Ex Parte Reexamination of U.S. Pat. No. 10,175,225, filed Jul. 15, 2022, 2 pages.
Non-Final Office Action in Ex Parle Reexamination for U.S. Appl. No. 90/019,032, issued Sep. 29, 2022, (61 pages).
Anonymous: Rotem delta Whole Blood Haemostasis System using Thromboelastometry US Operating Manual,: [retrieved on Oct. 30, 2015]. Retrieved from the internet: <URL: http://www.sfgh-poct. org/wp-content/uploads/2013/02/ROTEM-delta-US-Operat- ing-Manual-Part-12.pdf>, Sep. 2012.

(56)        References Cited

OTHER PUBLICATIONS

Calatzis et al., "Strategies to Assess Individual Susceptibility to abciximab Therapy Using a New Functional Assay," Annals of Hematology, (Berlin, DE) vol. 76, No. Suppl 1, p. A61, XP009097526, 1998.
Chakroun et al., "The influence of fibrin polymerization and platelet-mediated contractile forces on citrated whole blood thromboelastography profile," Thromb Haemost., 95(5):822-828, May 2006.
China National Intellectual Property Administration, Office Action, CN Patent Application No. 2016800743389, dated Apr. 23, 2020, 16 pages. cited by applicant.
Chinese Office Action (OA) for App. No. 200980151858.5 dated May 21, 2013, 16 pgs.
Chinese Office Action for App. No. 200980151858.5 dated Feb. 14, 2014, 4 pgs.
European Extended search report for App No. 13167983.9, dated Nov. 6, 2013, 3 pgs.
European Office Action for App. No. 08172769.5, dated Jun. 1, 2011, 12 pgs.
European Office Action for App. No. 12179576.9, dated May 22, 2013, 10 pgs.
European Office Action for App. No. 13167979.7, dated Nov. 15, 2016, 8pgs.
European Office Action for Application No. 13163014.7, dated Mar. 24, 2014, 12 pages.
European Patent Office, Extended European Search Report and Opinion, European Patent Application No. 16871654.6, dated May 27, 2019, 7 pages.
European Search Report and Opinion for Application No. 15187347. 8, dated Jun. 1, 2016 (16 Pages).
Extended European Search Report, European Patent Office, European Patent Application No. 18193752.5, dated May 13, 2019, 13 pages.
First Office Action with concise explanation of relevance, Chinese Patent Application No. 201680074338.9, dated Feb. 3, 2019, 5 pages.
Greilich et al., "Near-site monitoring of the antiplatelet drug abciximab using the Hemodyne analyzer and modified thrombelastograph," J Cardiothorac Vase Anesth., 13(1 ):58-64, Feb. 1999.
Hartert, "Blood Coagulation Studies with Thromboelastography—A New Research Method," Klin Wochenschrift 26:577-583, Oct. 1948 [English translation].
Healthpact, "Rotational thromboelastometry (ROTEM)—targeted therapy for coagulation management in patitnets with massive bleeding," "Health Policy Advisory Committee on Technology. Retrieved from the Internet: <URL:https://www.heath.qld.gov.au/healthpact/docs/briefs/WP024.pdg>-, 30 pages, Nov. 2012".
Japan Patent Office, Notification of Reasons for Refusal, JP Patent Application No. 2019-001775, dated Jan. 31, 2020, 13 pages.
Japan Patent Office, Office Action, Japanese Patent Application No. 2018-528982, dated Jul. 2, 2019, 14 pages.
Japanese Notification for Refusal for Application No. 2011-541392, dated Jun. 14, 2013, 4 pages.
Japanese notification of refusal for Ap. No. 2014-165975, dated Jul. 17, 2015, 8 pgs.
Japanese Office Action, Japanese Application No. 2015-191180, dated Nov. 17, 2017, 9 pages.
Kawasaki et al., "The effects of vasoactive agents, platelet agonists and anticoagulation on thrombelastography," Acta Anaesthesiol Scand., 51(9):1237-1244, Oct. 2007.
Khurana et al., "Monitoring platelet glycoprotein Iib/IIIa-fibrin interaction with tissue factor-activated thromboelastography," J Lab Clin Med., 130(4):401-411, Oct. 1997.
Korean Office Action for Application No. 1020117017187, dated Mar. 28, 2016, 11 pages.
Korean Office Action for Application No. 1020167029191, dated Nov. 17, 2016, 5 pages.

Lang et al., "Evaluation of the new device ROTEM platelet" [retrieved on Oct. 28, 2015]. Retrieved from the internet: <URL: https://www.rotem.de/wp-content/uploads/2014-09-Lang-et-al-2014. pdf>, Jan. 1, 2014.
National Intellectual Property Administration of China, Office Action, Chinese Patent Application No. 2016800743389, dated Aug. 12, 2019, 15 pages.
Nield et al., "MRI-based blood oxygen saturation measurements in infants and children with congenital heart disease," Pediatr Radiol., 32(7):518-522. Epub Apr. 16, 2002.
Nielsen et al., "Evaluation of the contribution of platelets to clot strength by thromboelastography in rabbits: the role of tissue factor and cytochalasin D," Anesth Anafa., 91(1):35-39, Jul. 2000.
Noon et al., "Reduction of blood trauma in roller pumps for long-term perfusion" World J Surg., 9(1):65-71, Feb. 1985.
Notification of Reasons for Refusal for Application No. 2015-132034, dated Jul. 29, 2016, 5 pages.
Novotny et al., "Platelets secrete a coagulation inhibitor functionally and antigenically similar to the lipoprotein associated coagulation inhibitor," Blood, 72(6):2020-2025, Dec. 1988.
Partial European search report, European Patent Application No. 18193752.5, dated Feb. 12, 2019, 15 pages.
PCT International Preliminary report on patentability for PCT/EP2009/067181, dated Jun. 29, 2011, 9 pages.
PCT International search report and written opinion for Ap. No. PCT/EP2009/067181, dated Mar. 22, 2010, 12 pgs.
PCT International Search Report and Written Opinion, PCT Application No. PCT/US16/34501, dated Aug. 31, 2016, 17 pages.
PCT International Search Report and Written Opinion, PCT Application No. PCT/US16/64800, dated Feb. 16, 2017, 14 pages.
PCT International Search Report and Written Opinion, PCT Application No. PCT/US18/40120, dated Sep. 20, 2018, 13 pages.
PCT International Search Report and Written Opinion, PCT Application No. PCT/US2016/064790, dated Feb. 15, 2017, 17 pages.
PCT International Search Report and Written Opinion, PCT Application No. PCT/US2016/064797, dated Feb. 15, 2017, 16 pages.
PCT International Search Report and Written Opinion, PCT Application No. PCT/US2016/064806, dated Feb. 15, 2017, 18 pages.
PCT International Search Report and Written Opinion, PCT Application No. PCT/U.S. Pat. No. 2016064797, dated May 27, 2019, 7 pages.
PCT International Search Report and Written Opinion, PCT Application No. PCT/US2017/049505, dated Nov. 2, 2017, 17 pages.
Prisco and Paniccia, "Point-of-Care Testing of Hemostasis in Cardiac Surgery", Thromb J., 1(1):1, May 6, 2003.
Rodzynek et al., "The transfer test: a new screening procedure for thrombotic diseases," J Surg Res., 35(3):227-233, Sep. 1983.
ROTEM.RTM. "When Minutes Count to Stop the Bleeding," Pentapharm GmbH, www.rotem.de, 6 pages, Jun. 2007. [brochure].
ROTEM.RTM. delta, "Targeted therapy stops the bleeding, " 6 pages, Jan. 6, 2014, [brochure].
ROTEM.RTM. delta, "Whole Blood Haemostasis System using Thromboelastomerty Operating Manual," 164 pages, Nov. 17, 2014 [brochure].
ROTEM.RTM., "Targeted therapy for coagulation management in patients with massive bleeding," https://www.health.qld.gov.au/_data/assets/pdf_file/0023/427145/wp024.pdf- , Nov. 2012, 30 pages, [brochure].
SALOOJA and Perry, "Thrombelastography," Blood Coagul Fibrinolysis, 12(5):327-37, Jul. 2001.
Shore-Lesserson et al., "Thromboelastography-guided transfusion algorithm reduces transfusions in complex cardiac surgery," Anesth Analg., 88(2):312-319, Feb. 1999.
Soria et al., "Fibrin stabilizing factor (F XIII) and collagen polymerization," Experientia, 31(11):1355-1357, Nov. 15, 1975.
Spannagl et al., "Point-of-Care Analysis of the Homostatic System," Laboratoriumsmedizin, (Kirchheim, DE), 26(1-2):68-76, Feb. 2002.
Srinivasa et al., "Thromboelastography: Where Is It and Where Is It Heading?" Int'l Anesthesiology Clinics, 39(1 ):35-49, Winter 2001.
Tanaka et al., "Thrombin generation assay and viscoelastic coagulation monitors demonstrate differences in the mode of thrombin

(56)     References Cited

OTHER PUBLICATIONS inhibition between unfractionated heparin and bivalirudin," Anesth Analg., 105(4):933-939, Oct. 2007.

United States Office Action, U.S. Appl. No. 14/958,889, dated Sep. 13, 2019, 18 pages.

United States Office Action, U.S. Appl. No. 15/648,345, dated Jan. 22, 2020, nine pages.

Canadian Intellectual Property Office, Examiner Requisition, CA Patent Application No. 3,033,000, Apr. 15, 2020, four pages.

China National Intellectual Property Administration, Office Action, CN Patent Application No. 201880056029.8, Sep. 15, 2020, 12 pages (with concise explanation of relevance).

European Patent Office, Extended European Search Report and Opinion, European Patent Application No. 17847520.8, Feb. 27, 2020, seven pages.

Japan Patent Office, Official Notice of Rejection, JP Patent Application No. 2020-501278, Jul. 14, 2020, eight pages.

United States Office Action, U.S. Appl. No. 14/958,889, filed May 31, 2019, ten pages.

United States Office Action, U.S. Appl. No. 14/958,889, filed Feb. 1, 2019, ten pages.

United States Office Action, U.S. Appl. No. 14/958,889, filed Jul. 5, 2018, ten pages.

United States Office Action, U.S. Appl. No. 14/500,248, filed Mar. 15, 2018, 12 pages.

United States Office Action, U.S. Appl. No. 14/500,248, filed Aug. 23, 2017, ten pages.

Office Action received for European Patent Application No. 13167983.9, mailed on Jan. 7, 2019, 3 pages.

Office Action received for European Patent Application No. 13167983.9, mailed on Jan. 16, 2017, 3 pages.

Office Action received for European Patent Application No. 20175351.4, mailed on Aug. 24, 2023, 4 pages.

Office Action received for European Patent Application No. 20175351.4, mailed on Feb. 15, 2022, 4 pages.

Office Action received for European Patent Application No. 20175351.4, mailed on Mar. 13, 2023, 5 pages.

Office Action received for Japanese Patent Application No. 2017-204523, mailed on Nov. 2, 2018, 6 pages (3 pages of English Translation and 3 pages of Original Document).

Office Action received for Japanese Patent Application No. 2019-135338, mailed on Aug. 14, 2020, 8 pages (4 pages of English Translation and 4 pages of Original Document).

Office Action received for Japanese Patent Application No. 2019-135338, mailed on Mar. 12, 2021, 4 pages (2 pages of English Translation and 2 pages of Original Document).

Office Action received for Japanese Patent Application No. 2021-143317, mailed on Dec. 9, 2022, 4 pages (2 pages of English Translation and 2 pages of Original Document).

Office Action received for Japanese Patent Application No. 2021-143317, mailed on Sep. 2, 2022, 4 pages (2 pages of English Translation and 2 pages of Original Document).

Office Action received for Japanese Patent Application No. 2023-082050, mailed on Mar. 22, 2024, 6 pages (3 pages of English Translation and 3 pages of Original Document).

Office Action received for Japanese Patent Application No. 2023-132583, mailed on Nov. 19, 2024, 3 pages (2 pages of Original OA and 1 page of English Translation).

Patent Owner's Mandatory Notices For Inter Partes Review of U.S. Pat. No. 9,410,971, dated Dec. 13, 2017, 5 pages.

Pertinent Materials Reviewed and Considered by James P. Landers, Ph. D filed on Jul. 29, 2019, Exhibit 2003 to PGR2019-00047.

Provisional Application for Patent Cover Sheet filed on Apr. 24, 2019, Exhibit 1004 to PGR2019-00047.

Scheduling Order for IPR2021-00293 [Paper 10] of U.S. Pat. No. 10,746,750, issued Jul. 1, 2021, 11 pages.

Third Party Observation filed in European Patent Application No. 12865280.7, dated Nov. 23, 2016, 4 pages.

Transmittal of Request for Ex Parte Reexamination of U.S. Pat. No. 11,061,038 filed by a Third Party Requester Jul. 13, 2021, 3 pages.

U.S. Pat. No. 6,613,286, issued Sep. 2, 2003, of Request for Ex Parte Reexamination filed by a Third Party Requester, Nov. 3, 2021, 20 pages.

U.S. Publication No. 20050220668AI to Coville ("Coville"), published Oct. 6, 2005, of Request for Ex Parte Reexamination filed by a Third Party Requester, Nov. 3, 2021, 18 pages.

Action and Response History in U.S. Appl. No. 17/831,845 [now U.S. Pat. No. 11,768,211], downloaded Oct. 31, 2023, 54 pages.

Advisory Action in Reexamination U.S. Appl. No. 90/019,032 dated Apr. 12, 2023 (5 pages).

Corrected Citations for the Petition as filed For Inter Partes Review of U.S. Pat. No. 9,272,280 B2, dated Jul. 26, 2017 [IPR2017-00852], 4 pages [Exhibit 1012].

Corrected Citations for the Petition as filed For Inter Partes Review of U.S. Pat. No. 9,410,972 [sic, 9,410,971] dated Jul. 26, 2017, 6 pages.

Decision to Grant received for European Patent Application No. 12179576.9, mailed on Jun. 20, 2014, 2 pages.

Decision to Grant received for European Patent Application No. 13163014.7, mailed on Jul. 16, 2015, 2 pages.

Decision to Grant received for European Patent Application No. 13167979.7, mailed on Jul. 5, 2018, 2 pages.

Decision to Grant received for European Patent Application No. 13167983.9, mailed on Apr. 23, 2020, 2 pages.

Decision to Grant received for Japanese Patent Application No. 2016-132792, mailed on Feb. 16, 2018, 5 pages (2 pages of English Translation and 3 pages of Original Document).

Decision to Grant received for Japanese Patent Application No. 2017-204523, mailed on Jun. 28, 2019, 5 pages (2 pages of English Translation and 3 pages of Original Document).

Decision to Grant received for Japanese Patent Application No. 2019-135338, mailed on Aug. 26, 2021, 5 pages (2 pages of English Translation and 3 pages of Original Document).

Decision to Grant received for Japanese Patent Application No. 2021-143317, mailed on Apr. 21, 2023, 5 pages (2 pages of English Translation and 3 pages of Original Document).

Decision to Grant received for Japanese patent application No. 2023-082050, Mailed on Aug. 16, 2024, 5 Pages.

European Search Report for EP Application No. 07121222 dated Apr. 9, 2008.

European Search Report for EP Application No. 09150740 dated Jun. 30, 2009.

European Search Report in EP Application No. 15174565.0 dated Nov. 17, 2015, 9 pgs.

Examiner Interview Summary in Reexamination U.S. Appl. No. 90/019,032 dated Mar. 2, 2023 (9 pages).

Examiner Interview Summary in Reexamination U.S. Appl. No. 90/019,098 dated Feb. 7, 2023 (3 pages).

Extended European Search Report and Search Opinion received for European Application No. 13163014.7, mailed on May 23, 2013, 6 pages.

Extended European Search Report and Search Opinion received for European Application No. 20175351.4, mailed on Sep. 21, 2020, 9 pages.

Extended European Search Report issued in European Patent Application No. 11766842.6, dated Oct. 21, 2015, 9 pages.

File History for Application Serial No. 15/644, 124 (downloaded Apr. 22, 2025).

File History of U.S. Appl. No. 13/397,398 as filed For Inter Partes Review of U.S. Pat. No. 9,272,280 dated Dec. 1, 2017, 873 pages.

Final Rejection in Reexamination U.S. Appl. No. 90/019,032 dated Jan. 27, 2023 (27 pages).

Final Rejection in Reexamination U.S. Appl. No. 90/019,098 dated Apr. 18, 2023 (16 pages).

Intention to Grant received for European Patent Application No. 12179576.9, mailed on Feb. 12, 2014, 5 pages.

Intention to Grant received for European Patent Application No. 13163014.7, mailed on Apr. 10, 2015, 5 pages.

Intention to Grant received for European Patent Application No. 13167979.7, mailed on Mar. 2, 2018, 5 pages.

Intention to Grant received for European Patent Application No. 13167983.9, mailed on Dec. 17, 2019, 5 pages.

(56) References Cited

OTHER PUBLICATIONS

Intention to Grant received for European Patent Application No. 20175351.4, mailed on Nov. 13, 2024, 6 pages.
International Preliminary Report and Written Opinion for PCT/ EP2010/050454 dated Jul. 19, 2011, 4 pages.
International Preliminary Report and Written Opinion for PCT/ EP2011/051803 dated Sep. 25, 2012.
International Search Report & Written Opinion for International Application No. PCT/US2016/034501, dated Aug. 31, 2016, 10 pages.
International Search Report and Written Opinion for PCT/EP2010/ 050454 dated Apr. 20, 2010, 6 pages.
International Search Report and Written Opinion for PCT/EP2011/ 051803.
International Search Report and Written Opinion for PCT/IB2016/ 053860 dated Sep. 19, 2016.
Interview Agenda in Reexamination U.S. Appl. No. 90/019,032 dated Nov. 10, 2022 (20 pages).
Interview Summary and Amendment in Reply to Action of Apr. 26, 2022 and Declaration of Dr. Robert Hillman in Reexamination U.S. Appl. No. 90/019,032, filed Jul. 26, 2022 (65 pages).
Interview Summary and Amendment in Reply to Action of Dec. 19, 2022 and Declaration of Dr. Gerald G. Fuller in Reexamination U.S. Appl. No. 90/019,098, filed Feb. 21, 2023 (199 pages).
Interview Summary and Amendment in Reply to Action of Jan. 27, 2023 and Declaration of Dr. Gerald G. Fuller in Reexamination U.S. Appl. No. 90/019,032, filed Mar. 27, 2023 (148 pages).
Interview Summary and Amendment in Reply to Action of Sep. 29, 2022 and Declaration of Dr. Gerald G. Fuller in Reexamination U.S. Appl. No. 90/019,032, filed Nov. 29, 2022 (218 pages).
Non-Final Office Action far U.S. Appl. No. 16/572,567, dated Oct. 27, 2022, (16 pages).
Non-Final Office Action far U.S. Appl. No. 17/372,637, dated Nov. 2, 2021, (20 pages).
Non-Final Office Action for U.S. Reexamination U.S. Appl. No. 90/019,098 dated Apr. 18, 2023, (68 pages).
Notice of Allowance in U.S. Appl. No. 16/708,334 dated May 9, 2023.
Office Action received for Australian Patent Application No. 2024201495, mailed on Apr. 3, 2025, 3 pages.
Office Action received for Chinese Patent Application No. 202111383415.8, mailed on Apr. 8, 2025, 16 pages.
Office Action received for Canadian Patent Application No. 3178189, mailed on Apr. 11, 2025, 7 pages.
Advisory Action received in co-pending U.S. Appl. No. 15/202,059, dated Sep. 21, 2017.
Amukele, et al., "Comparison of plasma with whole blood prothrombin time and fibrinogen on the same instrument," American Journal of Clinical Pathology, vol. 133, No. 4, Apr. 2010, pp. 550-556.
Anderson, "Multi—Dimensional Velocity Estimation with Ultrasound Using Spatial Quadrature," IEEE Transactions on Ultrasonics Ferroelectrics & Frequency Control, vol. 45, No. 3, 1998, pp. 852-861.
Anderson, "Preventing Deep Vein Thrombosis and Pulmonary Embolism," Center for Outcomes Research, UMass Med Center, 1998, 23 pages.
Azar et al., "Abciximab in Primary Coronary Angioplasty for Acute Myocardial Infarction Improves Short-and Medium- Term Outcomes", J. Am. Coll. Cardiol., Dec. 1998; 32 (7): 1996-2002. PubMed P.M.I.D.: 9857884.
Becker, R., "Cell-based models of coagulation: a paradigm in evolution," Journal of Thrombosis and Thrombolysis, vol. 20, No. 1, Aug. 2005, pp. 65-68.
Beer: Center for Reproductive Immunology & Genetics, "Thrombophilia: Inherited and Acquired," 6 pages, http://repro-med. net/papers/thromb.php. Mar. 30, 2005.
Bell, et al., "Thrombelastographic evaluation of coagulation in transurethral prostatectomy," British Journal of Urology, vol. 78, No. 5, 1996, pp. 737-741.

Bercoff et al., "In vivo breast tumor detection using transient elastography," Ultrasound in Medicine & Biology, vol. 29, No. 10, 2003, pp. 1387-1396.
Bercoff, et al., "Supersonic Shear Imaging: A New Technique for Soft Tissue Elasticity Mapping," IEEE Transactions on Ultrasonics Ferroelectrics & Frequency Control , vol. 51 , No. 4, 2004, pp. 396-409.
Bilgen, et al., "Error analysis in acoustic elastography. II. Strain estimation and SNR analysis", Journal of the Acoustical Society of America, vol. 101, 1997, pp. 1147-1154.
Bohs, et al., "A Real Time System for Quantifying and Displaying Two-Dimensional Velocities using Ultrasound," Ultrasound in Medicine & Biology, vol. 19, No. 9, Jul. 1993, pp. 751-761.
Bombeli, et al., "Updates in perioperative coagulation: physiology and management of thromboembolism and haemorrhage" British Journal of Anesthesia; vol. 93, No. 2, Aug. 2004, pp. 275-287.
Bonnefous, et al., "Time Domain Formulation of Pulse—Doppler Ultrasound and Blood Velocity Estimation by Cross Correlation," Ultrasonic Imaging 8, 1986, pp. 73-85.
Born, G.V., "Aggregation of Blood Platelets by Adenosine Diphosphate and its Reversal". Nature, Jun. 9, 1962; 194: 927-9. PubMed P.M. I.D.: 13871375.
Brock, et al., "Assessing Thrombin Generation at the Point of Care," Clinical Chemistry, vol. 55, No. 3, Mar. 2009, pp. 398-399.
Calle et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36 (2): 295-305. PubMed P.M. I.D.: 20045589.
Carr, M., "In vitro assessment of platelet function," Transfusion of Medicine Reviews, vol. 11, No. 2, Apr. 1997, pp. 106-115.
Carroll, et al., "Measurement of functional fibrinogen levels using the Thrombelastograph" Journal of Clinical Anesthesia, vol. 20, No. 3, May 2008, pp. 186-190.
Carter, G., "Coherence and time delay estimation," Proc IEEE, vol. 75, No. 2, 1987, pp. 236-255.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.
Chavez, J., "A novel thrombelastograph tissue factor / kaolin assay of activated clotting times for monitoring heparin anticoagulation during cardiopulmonary bypass," Anesthesia and Analgesia; vol. 99, No. Nov. 5, 2004, pp. 1290-1294.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Communication pursuant to Article 94(3) EPC dated Apr. 3, 2018 in co-pending application EP 12865280.7.
Communication Pursuant to Article 94(3) EPC issued for European Application No. 12865280.7, dated Mar. 18, 2019, 7 pages.
Communication Pursuant to Article 94(3) EPC, issue for European Application No. 12865280.7, dated Oct. 8, 2018, 17 pages.
Communication pursuant to Rule 114(2) EPC issued in European Patent Application No. 12865280.7, dated Dec. 13, 2016, 5 pages.
Communication pursuant to Rule 94(3) EPC issued in European Patent Application No. 12865280.7, dated Jul. 3, 2017, 3 pages.
Corrected Notice of Allowance issued for U.S. Appl. No. 15/202,059, dated Jun. 22, 2018.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Curry, et al., "Convention and near-patient tests of coagulation," British Journal of Anesthesia, vol. 7, No. 2, Apr. 2007, pp. 45-50.

(56) References Cited

OTHER PUBLICATIONS

Dahlback, B., "Blood Coagulation," Lancet, vol. 355, No. 9215, May 2000, pp. 1627-1632.

Decision Denying Patent Owner's Request for Rehearing of Final Decision filed on Dec. 5, 2019. Exhibit 1014 to IPR2018-00050.

Declaration of Keith B. Neeves, Ph.D. filed on Dec. 14, 2020. Exhibit 1002 to IPR2021-00293.

Declaration of U.S. Pat. No. 9,272,280, 67 pages.

Declaration of U.S. Pat. No. 9,410,971, 124 pages.

Definition of "Cavity". Merriam-Webster's Collegiate Dictionary. 2020. Exhibit 1018 to IPR2021-00293.

Delhaye et al., Temperature corrected thromboelastometry in hypothermic trauma patients: 6AP24. European Journal of Anaesthesiology, May / Jun. 2008, 25:84.

Deposition of Frank Michael LaDuca, Ph.D. on Feb. 13, 2019. Exhibit 1026 to IPR2021-00293.

Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.

Dorn-Beineke et al., "Evaluation of the Automated Coagulation Analyzer Sysmex CA—7000". Thromb. Res., 2005; 116 (2): 171-9. PubMed P.M.I.D.: 15907533.

Eikelboom et al., "Monitoring Unfractionated Heparin with the aPTT: Time for a Fresh Look". Thromb. Haemost. Nov. 2006; 96 (5): 547-52. Review. PubMed P.M.I.D.: 17080209.

Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.

Emelianov et al., "Ultrasound Elasticity Imaging of Deep Venous Thrombosis," Proc. IEEE Ultrasonics Symp., 2000, pp. 1791-1794.

EP Extended Search Report, dated Oct. 24, 2016, in co-pending International Application No. PCT/US2012/025270.

Euroanaesthesia 2004: Joint Meeting of the European Society of Anaesthesiologists and European Academy of Anaesthesiology Lisbon, Portugal, Jun. 5-8, 2004. (2004). European Journal of Anaesthesiology, 21(S32), 1-221. doi:10.1017/S0265021504000419.

Evans PA, Hawkins K, Lawrence M, Williams RL, Barrow MS, Thirumalai N, Williams PR. Rheometry and associated techniques for blood coagulation studies. Med Eng Phys. Jul. 2008;30(6):671-9. doi: 10.1016/j.medengphy.2007.08.005. Epub Sep. 27, 2007. PMID: 17900965.

Examination Report issued for Australian Application No. 2017248548, dated Jul. 9, 2018.

Examination Report issued in Australian Application No. 2012364908, dated Jul. 23, 2016, 4 pages.

Examination Report issued in Australian Application No. 2012364908, dated Jun. 27, 2017, 5 pages.

Examination Report issued in European Application No. 12865280.7, dated Apr. 3, 2018, 3 pages.

Examination Report issued in European Application No. 12865280.7, dated Mar. 7, 2017, 3 pages.

Extended European Search Report issued in European Patent Application No. 11766842.6, dated Oct. 21, 2015, 10 pages.

Extended Search Report issued in European U.S. Appl. No. 12/865,280, dated Oct. 24, 2016, 5 pages.

Fatemi et al., "C-Scan Imaging by Radiation Force Stimulated Acoustic Emission Method," Proc. IEEE Ultrasonics Symp., 1996, pp. 1459-1462.

Fatemi, et al., "Application of radiation force in noncontact measurement of the elastic parameters," Ultrasonic Imaging, vol. 21, No. 2, Apr. 1999 pp. 147-154.

Fatemi, et al., "Ultrasound-Stimulated Vibro-Acoustic Spectography," Science Magazine, vol. 280, No. 5360, 1998, pp. 82-85.

Fayed, Nirmeen et al. "Preoperative Thromboelastometry as a Predictor of Transfusion Requirements during Adult Living Donor Liver Transplantation." Transfusion medicine and hemotherapy :

offizielles Organ der Deutschen Gesellschaft fur Transfusionsmedizin und Immunhamatologie vol. 42,2 (2015): 99-108. doi:10.1159/000381733.

Ferraris, et al., "2011 Update to The Society of Thoracic Surgeons and the Society of Cardiovascular Anesthesiologists Blood Conservation Clinical Practice Guidelines," Annals of Thoracic Surgery, vol. 91, 2011, pp. 944-982.

Fertner, et al., "Comparison of Various Time Delay Estimation Methods by Computer Simulation," IEEE Transactions on Acoustics, Speech, and Signal Processing, vol. 34, No. 5, 1986, pp. 1329-1330.

File History of U.S. Appl. No. 16/146,333, dated Jul. 29, 2020, (156 pages). Exhibit 1013 to IPR2021-00293.

Final Written Decision filed on Oct. 2, 2019. Exhibit 1011 to IPR2018-00950.

Flanders et al., "Evaluation and Performance Characteristics of the STA-R Coagulation Analyzer". Clin Chem., Sep. 2002; 48 (9): 1622-1624. PubMed P.M.I.D.: 12194955.

Flax, et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, Nov. 1988, pp. 758-767.

Freedman, et al., "A Meta-Analysis of Thromboembolic Prophylaxis Following Elective Total Hip Arthroplasty," Journal of Bone and Joint Surgery, vol. 82—A, 2000, pp. 929-938.

Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2: 763-8.

Gaetano, G. de, et al., "Effect of Platelets on Clot Structuration, a Thrombelastographic Study," Thrombosis Research, vol. 3, No. 4, pp. 425-435, 1973.

Gallippi, et al., "Adaptive clutter filtering via blind source," Ultrasonic Imaging, vol. 24, No. 4, 2002, pp. 193-214.

Gallippi, et al., "BSS-based filtering of physiological and ARFI induced tissue and blood motion," Ultrasound in Medicine and Biology, vol. 29, No. 11, 2003, pp. 1583-1592.

Gallippi, et al., "Complex blind source separation for acoustic radiation force impulse imaging in the peripheral vasculature, in vivo," IEEE Ultrasonics Symposium, vol. 1, 2004, pp. 596-601.

Ganter et al., "Kaolin-Based Activated Coagulation Time Measured by Sonoclot in Patients Undergoing Cardiopulmonary Bypass." J. Cardiothorac. Vasc. Anesth, Aug. 2007; 21 (4): 524-8. PubMed P.M.I.D.: 17678778.

Ganter, et al., "Active, personalized, and balanced coagulation management saves lives in patients with massive bleeding," Anesthesiology, vol. 133, No. 5, Nov. 2010, pp. 1016-1018.

Gauss, et al., "Adaptive Imagining in the Thyroid Using Fundamental and Harmonic Echo Data," presented at IEEE Ultrasonics Symposium, 1999, pp. 1515-1519.

Gauss, et al., "Wavefront Estimation in the Human Breast," presented at SPIE Medical Imaging, vol. 4325, 2001, pp. 172-180.

Giunta, et al., "Estimation of Global Motion Parameters by Complex Linear Regression," IEEE Transactions on Image Processing, vol. 8, No. 11, 1999, pp. 1652-1657.

Glidden, Paul F., et al., "Thromboelastograph Assay for Measuring the Mechanical Strength of Fibrin Sealant Clots," Clinical and Applied Thombosis / Hemostasis, vol. 6, No. 4, Oct. 2000, pp. 226-233.

Gorlinger et al., "Recommendations for using the ROTEM® in the management of perioperative bleeding in Cardiac Surgery" Recommendations from the ROTEM® Expert Meeting Working Group, Munich 2007, 10 pages.

Gosselin et al., "Monitoring Oral Anticoagulant Therapy with Point-of-Care Devices: Correlations and Caveats". Clin. Chem., Sep. 1997; 43 (9): 1785-6. PubMed P.M.I.D.: 9299978.

Greilich, Philip E., et al., "A Modified Thromboelastographic Method for Monitoring c7E3 Fab in Heparinized Patients," Anesth Analg, vol. 84, 1997, pp. 31-38.

Gurbel, et al., "Platelet function monitoring in patients with coronary artery disease," Journal of the American College of Cardiology, vol. 50, No. 19, Nov. 2007, pp. 1822-1834.

(56)        References Cited

OTHER PUBLICATIONS

Hardisty R. M. et al., "Fibrinogen as a Co- factor in the Reaction of Platelets with Kaolin," May 7, 1966, Nature Publishing Group, Edition 210, vol. 644 (http://www.nature.com/nature/journal/v210/n5036/abs/210644a0.html).

Harrison, P. Platelet Function Analysis. Blood Rev. Mar. 2005; 19 (2): 111-23. Review. PubMed P.M.I.D.: 15603914.

Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.

Hartley, et al., "Doppler Measurement of Acoustic Streaming," IEEE Ultrasonics Symposium Proceedings, 1995, pp. 1537-1540.

Hemostasis and Thrombosis: Basic Principles and Clinical Practice Third edition. Edited by Robert W. Colman et al., 1827 pp. 1-25, illustrated. Philadelphia, Lippincott Company, 1994.

Hett, et al., "Sonoclot Analysis," British Journal of Anaesthesia, vol. 75, No. 6, Dec. 1995, pp. 771-776. Review. PubMed P.M.I.D.: 8672329.

Hirsh et al., "Oral anticoagulants. Mechanism of Action, Clinical Effectiveness, and Optimal Therapeutic Range". Chest. Oct. 1992; 102 (4 Suppl.): 312S-326S. Review. PubMed P.M.I.D.: 1345417.

Hirsh, et al., "How we diagnose and treat deep vein thrombosis," Blood, vol. 99, 2002, pp. 3102-3110.

Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.

Huang, et al., "Detection of blood coagulation and clot formation using quantitative ultrasonic parameters," Ultrasound in Medicine and Biology, vol. 31, No. 11, Nov. 2005, pp. 1567-1573.

Huang, et al.," Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.

*Instrumentation Laboratory Co.* v. *HemoSonics LLP*, IPR201700852, Paper No. 47 (PTAB Feb. 13, 2019) ("852 FWD"), 25 pages.

*Instrumentation Laboratory Co.* v. *HemoSonics LLP*, IPR201700855, Paper No. 55 (PTAB Feb. 13, 2019) ("971 FWD"), 55 pages.

International Preliminary Report on Patentability & Written Opinion, dated Aug. 27, 2013, in connection with International Application No. PCT/US2012/025278.

International Preliminary Report on Patentability & Written Opinion, dated Mar. 20, 2012, in connection with International Application No. PCT/US2010/049342.

International Preliminary Report on Patentability & Written Opinion, dated Nov. 19, 2013, in connection with International Application No. PCT/US2012/038553.

International Preliminary Report on Patentability & Written Opinion, dated Oct. 8, 2013, in connection with International Application No. PCT/US2012/025270.

International Preliminary Report on Patentability & Written Opinion, dated Oct. 9, 2012, in connection with International Application No. PCT/US2011/031832.

International Search Report & Written Opinion of the International Searching Authority, received in corresponding application No. PCT/US2010/049342, dated Nov. 16, 2010.

International Search Report & Written Opinion of the International Searching Authority, received in corresponding application No. PCT/US2011/031832, dated Dec. 15, 2011.

International Search Report, dated Aug. 20, 2013, in connection with International Application No. PCT/US2012/025278.

International Search Report, dated Jan. 2, 2013, in connection with International Application No. PCT/US2012/038553.

International Search Report, dated Sep. 30, 2013, in connection with International Application No. PCT/US2012/025270.

Ivandic et al., "Determination of Clopidogrel Resistance by Whole Blood Platelet Aggregometry and Inhibitors of the P2Y12 Receptor". Clinical Chemistry, vol. 52, No. 3, Mar. 2006, pp. 383-388. PubMed P.M.I.D.: 16423907.

Jacovitti, et al., "Discrete Time Techniques for Time Delay Estimation," IEEE Transactions on Signal Processing, vol. 41, No. 2, Feb. 1993, pp. 525-533.

Janus TJ, Lewis SD, Lorand L, Shafer JA. Promotion of thrombin-catalyzed activation of factor XIII by fibrinogen. Biochemistry. Dec. 20, 1983;22(26):6269-72. doi: 10.1021/bi00295a035. PMID: 6661434.

Japanese Office Action in International Application No. JP2015191180, dated Nov. 17, 2017, (9 pages including English Translation).

Jensen, "A New Method for Estimation of Velocity Vectors," IEEE Transactions on Ultrasonics, Ferroelectrics and Frequency Control, vol. 45, No. 3, 1998, pp. 837-851.

Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.

Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110 (1): 36-45. PubMed P.M.I.D.: 7609566.

Kadi, et al., "On the performance of regression and step-initialized IIR Clutter Filters," IEEE Transactions on Ultrasonics, Ferroelectrics, and Frequency Control, vol. 42, 1995, pp. 827-837.

Kasai, et al., "Real-time Two-Dimensional Blood Flow Imaging Using an Autocorrelation Technique," IEEE Ultrasonics Symposium, vol. 32, No. 3, 1985, pp. 458-464.

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keith B. Neeves, Curriculum Vitæ, Sep. 1, 2020, (25 pages). Exhibit 1003 to IPR2021-00293.

Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention". Am. J. Cardiol., Aug. 15, 1999; 84 (4): 391-5 .PubMed P.M.I.D.: 10468074.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab-Modified Thrombelatography in Patients Undergoing Cardiac Surgery," Anesth Analg, vol. 89, 1999, pp. 580-584.

Koepke, J., "Point-of-Care Coagulation Testing," Laboratory Medicine, vol. 31, No. 6, Jun. 2000, pp. 343-346.

Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33 (3): 153-8. PubMed P.M.I.D.: 11680728.

Kozek-Langenecker, S. Intensive Care Medicine, Annual Update 2007, Monitoring of Hemostasis in Emergency Medicine, pp. 847-860, Springer New York.

Kruse, et al., "A new high-resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.

Kuntamukkula MS, McIntire LV, Moake JL, Peterson DM, Thompson WJ. Rheological studies of the contractile force within platelet-fibrin clots: effects of prostaglandin E1, dibutyryl-cAMP and dibutyryl-cGMP. Thromb Res. Dec. 1978;13(6):957-69. doi: 10.1016/0049-3848(78)90225-6. PMID: 219559.

Lang T, von Depka M. Diagnostische Möglichkeiten und Grenzen der Thrombelastometrie/-graphie [Possibilities and limitations of thrombelastometry/-graphy]. Hamostaseologie. Aug. 2006;26(3 Suppl 1): S20-9. English Translation, with Declaration. PMID: 16953288.

Lang T, von Depka M. Diagnostische Möglichkeiten und Grenzen der Thrombelastometrie/-graphie [Possibilities and limitations of thrombelastometry/-graphy]. Hamostaseologie. Aug. 2006;26(3 Suppl 1):S20-9. German. PMID: 16953288.

Lang, T. & Depka, M.. (2006). Possibilities and limitations of thromboelastometry/thromboelastography. Hamostaseologie. 26. S21-S29. 10.1055/s-0037-1617078.

(56)           References Cited

OTHER PUBLICATIONS

Ledoux, et al., "Reduction of the clutter component in Doppler ultrasound signals based on singular value decomposition: a simulation study," vol. 19, No. 1, 1997, pp. 1-18.

Lerner, et al., "Sono-elasticity: medical elasticity images derived from ultrasound signals in mechanically vibrated targets," Ultrasound in Medicine & Biology, vol. 16, 1998, pp. 317-327.

Li et al., "The Xylum Clot Signature Analyzer: A Dynamic Flow System that Simulates Vascular Injury". Thromb. Res., Dec. 15, 1998; 92 (6 Suppl. 2): S67-77. PubMed P.M.I.D.: 9886913.

Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Machado et al., "Evaluation of an Ultrasonic Method Applied to the Measurement of Blood Coagulation Time". Physiol. Meas., May 1997; 18 (2): 129-43. PubMed P.M.I.D .: 9183807.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.

McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.

Moake J Overview of Hemostasis. Merck Manuals 2016 http://www.merckmanuals.com/professional/hematology-and-oncology/hemostasis/overview-of-hemostasis.

Motovska et al., "Benefits and Risks of Clopidogrel Use in Patients with Coronary Artery Disease: Evidence from Randomized Studies and Registries". Clin. Ther., 2008; 30 Pt. 2: 2191-202. J. Clinthera., 2008.12.001. Review. PubMed P.M.I.D.: 19281914.

Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15 (6): 652-9. PubMed P.M.I.D.: 18805846.

Nam et al., "Evaluation of the Roche CoaguChek XS Handheld Coagulation Analyzer in a Cardiac Outpatient Clinic". Ann. Clin. Lab. Sci., 2008 Winter; 38 (1): 37-40. PubMed P.M.I.D.: 18316780.

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

Nielson, et al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.

Notice of Allowance issued for U.S. Appl. No. 15/202,059, dated May 23, 2018.

Notice of Allowance issued for U.S. Appl. No. 15/991,677, dated Nov. 2, 2018.

O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.

O'Donnell, et al., "Role of the Thrombelastograph as an adjunctive test in thrombophilia screening," Blood Coagulation and Fibrinolysis, vol. 15, No. 3, Apr. 2004, pp. 207-211.

Oberhardt, et al., "Dry reagent technology for rapid, convenient measurements of blood coagulation and fibrinolysis," Clinical Chemistry, vol. 37, No. 4, Apr. 1991, pp. 520-526.

Office Action issued for Canadian Application No. 2,823,729, dated Mar. 9, 2018.

Office Action issued for Canadian Application No. 2823729, dated Nov. 14, 2018, 4 pages.

Office Action issued for Chinese Application No. 2017101635956, dated Jul. 17, 2018.

Office Action issued for U.S. Appl. No. 15/904,984, dated Jul. 12, 2018.

Office Action received in co-pending U.S. Appl. No. 15/202,059, dated Jan. 12, 2018.

Office Action received in co-pending U.S. Appl. No. 15/202,059, dated Jul. 13, 2017.

Office Action received in co-pending U.S. Appl. No. 15/202,059, dated Oct. 4, 2016.

Office Action received in co-pending U.S. Appl. No. 15/644, 124, dated Feb. 6, 2018.

Office Action received in co-pending U.S. Appl. No. 15/644, 124, dated Nov. 29, 2017.

Office Action received in co-pending U.S. Appl. No. 15/644,124, dated Sep. 7, 2017.

Office Action received in U.S. Appl. No. 15/357,492, dated Jun. 22, 2017.

Ophir, et al., "Elastography: A Quantitative Method for Imaging the Elasticity of Biological Tissues," Ultrasonic Imaging, vol. 13, No. 2, 1991, pp. 111-134.

Packham, M., "Role of platelets in thrombosis and hemostasis," Canadian Journal of Physiology and Pharmacology, vol. 72, No. 3, Mar. 1994, pp. 278-284.

Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.

Parsons, et al., "Age Determiniation of Experimental Venous Thrombi by Ultrasonic Tissue Characterization," Journal of Vascular Surgery, vol. 17, 1993, 470-478.

Patent Owner's Response For Inter Partes Review of U.S. Pat. No. 9,915,671, dated Jan. 4, 2019, 37 pages.

Patent Owner's Response to the Decision to Institute Inter Partes Review of U.S. Pat. No. 9,272,280, dated Dec. 1, 2017, 39 pages.

Patent Owner's Response to the Decision to Institute Inter Partes Review of U.S. Pat. No. 9,410,971, entered Dec. 1, 2017, 59 pages.

Patil, et al., "3D prostate elastography: algorithm, simulations and experiments," Physics in Medicine & Biology, vol. 52, No. 12, 2007, pp. 3643-3663.

Peeters et al., "Ultrasonic Measurements of Coagulation and Fibrinolysis". J. Clin. Pathol., May 1964; 17: 320-3. PubMed P.M.I.D.: 14159472; PubMed Central P.M.C.I.D.: PMC480759.

Perry, et al., "Point-of-care testing in haemostasis," British Journal of Haematology, vol. 150, No. 5, Sep. 2010, pp. 501-514.

Pertinent Materials Reviewed and Considered by Keith Neeves, Ph.D. filed on Dec. 14, 2020. Exhibit 1019 to IPR2021-00293.

Petition for Inter Partes Review of U.S. Pat. No. 10,746,750 dated Dec. 14, 2020, 79 pages.

Petitioner's Reply to Patent Owner's Response of U.S. Pat. No. 9,272,280 dated Mar. 1, 2018, 17 pages.

Petitioner's Reply to Patent Owner's Response of U.S. Pat. No. 9,410,971 dated Mar. 1, 2018, 25 pages.

Pivalizza, et al., "Perioperative thromboelastography and sonoclot analysis in morbidly obese patients," Canadian Journal of Anaesthesia, vol. 44, No. 9, Sep. 1997, pp. 942-945.

Plotkin AJ, Wade CE, Jenkins DH, Smith KA, Noe JC, Park MS, Perkins JG, Holcomb JB. A reduction in clot formation rate and

(56) References Cited

OTHER PUBLICATIONS strength assessed by thrombelastography is indicative of transfusion requirements in patients with penetrating injuries. J Trauma. Feb. 2008;64(2 Suppl):S64-8. doi: 10.1097/TA.0b013e318160772d. PMID: 18376174.

Price et al., "Prognostic Significance of Post-Clopidogrel Platelet Reactivity Assessed by a Point-of-Care Assay on Thrombotic Events after Drug-Eluting Stent Implantation". Eur. Heart Apr. 2008; 29 (8): 992-1000. PubMed P.M.I.D.: 18263931.

Rao, G., "Need for a point-of-care assay for monitoring antiplatelet and antithrombotic therapies," Stroke, vol. 40, No. 6, Jun. 2009, pp. 2271-2272.

Riou, Chonavel et al., "Fast adaptive eigenvalue decomposition: a maximum likelihood approach," Signal Processing, 83, 2003, pp. 307-324.

Rotem Delta Targeted Therapy Stop the Bleeding. 2013. Exhibit 1027 to IPR2021-00293.

Rubin, et al., "Clinical application of sonographic elasticity imaging for aging of deep venous thrombosis: preliminary findings," Journal of Ultrasound in Medicine, vol. 22, 2003, pp. 443-448.

Ruzicka, K., et al. Evaluation of Bedside Prothrombin Time and Activated Partial Thromboplastin Time Measurement by Coagulation Analyzer Coagucheck Plus in Various Clinical Settings. Throm. Res., 87 (5) 1997 pp. 431-440. See also, Hillman, R., 1988 U.S. Pat. No. 4,756,884. Capillary Fill Device.

Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.

Sarvazyan, et al., "Shear Wave Elasticity Imagining—A New Ultrasonic Technology of Medical Diagnostics," Ultrasound in Medicine and Biology, vol. 24, 1998, pp. 1419-1436.

Scharbert et al., "Evaluation of the Platelet Mapping Assay on Rotational Thromboelastometry ROTEM". Platelets. Mar. 2009; 20 (2): 125-30. PubMed P.M.I.D. 19235055.

Schmitt, C., et al., "Characterization of blood clot viscoelasticity by dynamic ultrasound elastography and modeling of the rheological behavior," Journal of Biomechanics, vol. 44, No. 4, 2011, pp. 622-629.

Shi, et al., "Color Doppler Detection of Acoustic Streaming in a Hematoma Model," Ultrasound in Medicine and Biology, vol. 27, No. 9, 2001, pp. 1255-1264.

Shi, et al., "Color Doppler imaging of acoustic streaming in blood and clot," IEEE Ultrasonics Symposium, vol. 2, 1999, pp. 1315-1318.

Shi, et al., "Experimental Investigation and Finite Element Simulation of Streaming in Blood in Cylindrical Models," IEEE Ultrasonics Symposium, vol. 2, 2000, pp. 1509-1512.

Shi, Quantitative Investigation of Acoustic Streaming in Blood, J. Acoust. Soc. Am. 111, Feb. 2002, pp. 1110-1121.

Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.

Shore-Lesseron., Evidence Based Coagulation Monitors: Heparin Monitoring, Thromboelastography, and Platelet Function. Sem. Cardiothoracic Vasc. Anesthesia., Mar. 2005; 9 (1): 42-52.

Shung, et al., "Ultrasonic characterization of blood during coagulation," Journal of Clinical Ultrasound, vol. 12, No. 3, 1984, pp. 147-153.

Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.

Spiel, A. O. et al.,, "Validation of rotation thrombelastography in a model of systemic activation of fibrinolysis and coagulation in humans", Journal of Thrombosis and Haemostasis, 2006; 4: 411-416.

Srinivasan, et al., "Elastographic imaging using staggered strain estimates," Ultrasonic Imaging, vol. 24, 2002, pp. 229-245.

Strobach, P., "Low-rank adaptive filters," IEEE Trans Signal Process, vol. 44, No. 12, 1996, pp. 2932-2947.

Sugimoto, et al., "Tissue Hardness Measurement Using the Radiation Force of Focused Ultrasound," Proc. IEEE Ultrason. Symp., 1990, pp. 1377-1380.

Sumino, et al., "Measurements of ultrasonic pulse arrival time differences produced by abdominal wall specimens," Journal of the Acoustical Society of America, vol. 90, No. 6, 1991, pp. 2924-2930.

Taborski et al., "Analytical Performance of the New Coagulation Monitoring System INRatio for the Determination of INR Compared with the Coagulation Monitor Coaguchek S and an Established Laboratory Method" J. Thromb. Thrombolysis. Oct. 2004; 18 (2): 103-7. PubMed P.M.I.D.: 15789176.

Third party observation filed in European Patent Application No. 11766842.6, dated Mar. 6, 2016, 10 pages.

Third party observation filed in U.S. Appl. No. 15/202,059 , filed Nov. 30, 2016 , 40 pages .

Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.

Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6 (1): 1-12.

Toner, et al., "Blood-on-a-chip," Annual Review of Biomedical Engineering, vol. 7, 2005, pp. 77-103.

Torr, "The Acoustic Radiation Force," Am. J. Phys., vol. 52, 1984, pp. 402-408.

Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.

Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993: 71: 9-15.

Trial Board Order For Inter Partes Review Of U.S. Pat. No. 9,272,280 B2, 13 pages.

Trial Board Order for Inter Partes Review of U.S. Pat. No. 9,410,971 B2, 27 pages.

Trial Paper For Inter Partes Review of U.S. Pat. No. 9,272,280 B2 dated Jul. 11, 2018, 10 pages.

Trial Paper For Inter Partes Review of U.S. Pat. No. 9,410,971 dated Aug. 28, 2018, 3 pages.

Trial Paper For Inter Partes Review of U.S. Pat. No. 9,410,971 dated Dec. 1, 2017, 4 pages.

Trial Paper For Inter Partes Review of U.S. Pat. No. 9,410,971 dated Jul. 11, 2018, 10 pages.

Trial Paper For Inter Partes Review of U.S. Pat. No. 9,410,971 dated Oct. 2, 2017, 11 pages.

Tripodi et al., "International Sensitivity Index Calibration of the Near-Patient Testing Prothrombin Time Monitor, Pro Time". Am. J. Clin. Pathol., Feb. 2003; 119 (2): 241-5. PubMed P.M.I.D.: 12579994.

Versteeg et al., "New Fundamentals in Hemostasis", Physiol. Rev. Jan. 2013; 93 (1): 327-58. Review. PubMed P.M.I.D.: 23303912.

Vig, et al., "Thromboelastography: a reliable test ?" Blood Coagulation and Fibrinolysis, vol. 12, No. 7, Oct. 2001, 555-561.

Viola, et al., "A Comparison between spline-based and phase domain time-delay estimators," IEEE Transactions on Ultrasonics, Ferroelectrics, and Frequency Control, vol. 53, No. 3, 2006, pp. 515-517.

Viola, et al., "A comparison of the performance of time-delay estimators in medical ultrasound," IEEE Transactions on Ultrasonics Ferroelectrics & Frequency Control., vol. 50, 2003, pp. 392-401.

Viola, et al., "A Spline Based Algorithm for Continuous Time Delay Estimation Using Sampled Data," IEEE Transactions on Ultrasonics Ferroelectrics & Frequency Control, in press, 2005, pp. 80-93.

Viola, et al., "Analysis of Clot Formation with Acoustic Radiation Force," SPIE Proceedings, vol. 4689, 2002, pp. 235-242 and pp. 1-2.

(56)                    References Cited

OTHER PUBLICATIONS

Viola, et al., "Comparison of Time Delay Estimators in Medical Ultrasound," IEEE Ultrasonics Symposium, vol. 2, 2001, pp. 1485-1488.

Viola, et al., "Efficient and Accurate Spline-Based Time Delay Estimation," IEEE Ultrasonics Symposium, vol. 2, 2004, pp. 870-873.

Viola, et al., "Imaging Viscoelastic Properties of the Vitreous," Ultrasonics Symposium, vol. 2, 2001, pp. 1623-1626.

Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.

Viola, et al., "Ultrasound echo decorrelation due to acoustic radiation force," IEEE Ultrasonics Symposium Proceedings, vol. 2, 2002, pp. 1903-1906.

Voleiis, A., et al., "Ultrasonic method for the whole blood coagulation analysis," Ultrasonics, vol. 40, May 2002, pp. 101-107.

Walker, et al., "A Fundamental Limit on Delay Estimation Using Partially Correlated Speckle Signals," IEEE Transactions on Ultrasonics , Ferroelectrics and Frequency Control, vol. 42, 1995, pp. 301-308.

Walker, et al., "A Fundamental Limit on the Accuracy of Speckle Signal Alignment," IEEE Ultrasonics Symposium Proceedings, vol. 3, 1994, pp. 1787-1791.

Walker, et al., "A Method of Imagining Viscoelastic Parameters with Acoustic Radiation Force," Physics in Medicine and Biology, vol. 45, No. 6, 2000, pp. 1437-1447.

Walker, et al., "Application of Acoustic Radiation Force in Ophthalmic Ultrasound," Proc. IEEE Ultrason. Symp., vol. 2, 1997, pp. 1291-1295.

Walker, et al., "Real-Time Imaging of Tissue Vibration Using a Two-Dimensional Speckle Tracking System," IEEE Ultrason. Symp., 1993, pp. 873-877.

Walker, et al., "The Significance of Correlation in Ultrasound Signal Processing," SPIE Proceedings, vol. 4325, 2001, pp. 159-171.

Webster, Medical Instrumentation: Application and Design, New York: John Wiley & Sons, 1998, 6 pages.

Weisel JW. The mechanical properties of fibrin for basic scientists and clinicians. Biophys Chem. Dec. 20, 2004;112 (2-3):267-76. doi: 10.1016/j.bpc.2004.07.029. PMID: 15572258.

Weiss, H J et al. "The effect of salicylates on the hemostatic properties of platelets in man." The Journal of clinical investigation vol. 47,9 (1968): 2169-80. doi:10.1172/JCI105903.

Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.

Whitten, et al., "Thromboelastography: past, present, and future," Anesthesiology, vol. 92, No. 5, May 2000, pp. 1223-1225.

Wolberg AS. Plasma and cellular contributions to fibrin network formation, structure and stability. Haemophilia. May 2010; 16 Suppl 3:7-12. doi: 10.1111/j.1365-2516.2010.02253.x. PMID: 20586795.

Wolff et al., "Aspirin for the Primary Prevention of Cardiovascular Events: an Update of the Evidence for the U.S. Preventive Services Task Force". Ann. Intern. Med., Mar. 17, 2009; 150 (6): 405-10. Review. PubMed P.M.I.D.: 19293073.

Yu, et al., "Single-Ensemble-Based Eigen-Processing Methods for Color Flow Imaging," IEEE Transactions on Ultrasonics, Ferroelectrics, and Frequency Controls, vol. 55, No. 3, 2008, pp. 573-587.

Final Office Action received in U.S. Appl. No. 16/201,522, dated Jan. 22, 2021, (20 pages).

Harris, et al., "Evaluation of recurrent thrombosis and hypercoagulability," American Family Physician, vol. 56, No. 6, Oct. 1997, pp. 1591-1596, pp. 1601-1602.

Ickx, Brigitte, "Point-of-Care Monitoring of Haemostasis in the OR and the ICU," European Society of Anaesthesiologists. Jun. 5, 2004, pp. 79-83.

Jensen, Estimation of Blood Velocities Using Ultrasound, 1996, pp. 195-225.

Jolliffe, IT., "Principal Component Analysis," Springer Series in Statistics, 2nd edition, Springer, NY, 2002.

Khurana, Sandeep, et al., "Thromboelastography Can Rapidly Bioassay Fibrinogen," Anesthesiology, vol. 85, No. 3A, Sep. 1996, p. A457.

Pallister CJ, Watson MS (2010). Haematology. Scion Publishing. pp. 336-347. ISBN 1-904842-39-9.

Alsberg E, Feinstein E, Joy MP, Prentiss M, Ingber DE. Magnetically-guided self-assembly of fibrin matrices with ordered nano-scale structure for tissue engineering. Tissue Eng. Nov. 2006;12(11):3247-56. doi: 10.1089/ten.2006.12.3247. PMID: 17518638.

Berney, Helen & Riordan, J. (2008). Impedance measurement monitors blood coagulation. Analog Dialogue. 42, (3 pages).

Crochemore T, Piza FMT, Rodrigues RDR, Guerra JCC, Ferraz LJR, Corrêa Td. A new era of thromboelastometry. Einstein (Sao Paulo). Jul.-Sep. 2017;15(3):380-385. doi: 10.1590/S1679-45082017MD3130. Epub Jun. 12, 2017. PMID: 28614427; PMCID: PMC5823059.

Cuisset T, Frere C, Poyet R, et al. Clopidogrel response: Head-to-head comparison of different platelet assays to identify clopidogrel non-responder patients after coronary stenting. Archives of Cardiovascular Diseases. 2010; 103(1): 39-45.

Douning et al., "Temperature Corrected Thrombelastography in Hypothermic Patients". Anesthesia & Analgesia, Oct. 1995; 81 (3): 608-611.

Evans, et al., "Rheometry and associated techniques for blood coagulation studies," Medical Engineering and Physics, vol. 30, No. 6, Jul. 2008, pp. 671-679.

Examiner Requisition for Canadian Patent Application No. 3,033,000, dated Apr. 15, 2020, 4 pages.

Extended European Search Report for European Patent Application No. 17847520.8, dated Feb. 27, 2020, 7 pages.

Faulds, D et al., "Abciximab (c7E3 Fab). A review of its pharmacology and therapeutic potential in ischaemic heart disease; Drugs 583-98 (1994)" PubMed P.M.I.D.: 7528131 ("Faulds 1994").

Final Office Action for U.S. Appl. No. 14/500,248, dated Mar. 15, 2018, 12 pages.

Final Office Action for U.S. Appl. No. 14/958,889, dated Feb. 1, 2019, 10 pages.

Final Office Action for U.S. Appl. No. 14/958,889, dated Sep. 13, 2019, 18 pages.

Ganter, et al., "Coagulation monitoring: current techniques and clinical use of viscoelastic point-of-care coagulation devices," Anesthesia and Analgesia, vol. 106, No. 5, May 2008, pp. 1366-1375.

Gorlinger, K., et al., "Perioperative Coagulation Management and Control of Platelet Transfusion by Point-of-Care Platelet Function Analysis," Transfus Med Hemother 34: 396-411 (2007).

Hanecke, P and Klouche, M, Thrombelastography Today: Practicability and Analytical Power, Transfusion Medicine and Hemotherapy. 34. 421-428 (2007) ("Hanecke").

Harrison P. Assessment of platelet function in the laboratory. Hamostaseologie. Jan. 2009;29(1):25-31. PMID: 19151842, (7 pages).

Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18 . 1994.

International Search Report & Written Opinion for International Application No. PCT/US2016/034501, dated Aug. 31, 2016, 17 pages.

International Search Report & Written Opinion for International Application No. PCT/US2017/049505, dated Nov. 2, 2017, 17 pages.

International Search Report & Written Opinion for International Application No. PCT/US2018/040120, dated Sep. 20, 2018, 13 pages.

Janmey PA, Erdile L, Bale MD, Ferry JD. Kinetics of fibrinoligomer formation observed by electron microscopy. Biochemistry. 1983; 22 (18): 4336-40.

Kuntamukkula MS, McIntire LV, Moake JL, Peterson DM, Thompson WJ. Rheological studies of the contractile force within platelet

(56) References Cited

OTHER PUBLICATIONS fibrin clots: effects of prostaglandin E1, dibutyryl—CAMP and dibutyryl CGMP. Thrombosis research. 1978; 13 (6): 957-69.
Liptak (CRC Press). Process Measurement and Analysis vol. 1, Chapter 8 Analytical Instrumentation. 8.53 Rheometers, 1628-1636, 2003.
Multiplate® Analyzer Product Guide.
Neil Harris, et al., ""Coagulation Test a Primer on Hemostasis for Clinical Chemists"," Clinical Laboratory News, Jan. 1, 2012, retrieved from: https://www.aacc.org/cln/articles/2012/january/coagulation-tests, (4 pages).
Nielson V, A Comparison of the Thromblelastograph and ROTEM, Blood Coagulation and Fibrinolysis 18: 3, 247-252, 2007.
Non-Final Office Action for U.S. Appl. No. 14/500,248, dated Aug. 23, 2017, 10 pages.
Non-Final Office Action for U.S. Appl. No. 14/958,889, dated Jul. 5, 2018, 10 pages.
Non-Final Office Action for U.S. Appl. No. 14/958,889, dated May 31, 2019, 10 pages.
Office Action for Chinese Application No. 2016800743389, dated Apr. 23, 2020, 16 pages, (with English translation).
Office Action in Australian Application. No. 2016364931, dated Mar. 4, 2019, 4 pages.
Office Action in Chinese Application No. 201880056029.8, dated Sep. 15, 2020, 12 pages (with concise explanation of relevance).
Official Notice of Rejection for Japanese Patent Application No. 2020-501278, dated Jul. 14, 2020, 8 pages.
Plotkin, et al., The Journal of Trauma: Injury, Infection, and Critical Care. 2008.
Search Report for Chinese Application No. 201680074338.9, dated Jan. 25, 2019, 3 pages.
Second Office Action for Chinese Application No. 201680074338.9, dated Aug. 12, 2019, 13 pages (with English translation).
The 510(k) Substantial Equivalence Determination Decision Summary for ROTEM delta, FDA clearance No. K083842 (the "Decision Summary for ROTEM delta"), 11 pages.
The 510(k) Summary for ROTEM delta, FDA clearance No. K083842 ("the 510 (k) Summary for ROTEM delta"), 14 pages.
Thurston GB. Viscoelasticity of Human Blood. Biophysical Journal. 1972; 12: 1205-1217.
VerifyNow® Product Guide.
Werner Blättler, P.Werner Straub, Andreas Peyer, Effect of in vivo produced fibrinogenfibrin intermediates on viscosity of human blood, Thrombosis Research, vol. 4, Issue 6, 1974, pp. 787-801.
Americas Styrenics Styron® 666D Polystyrene; Dow Chemical, 2008. http://www.matweb.com/search/datasheet_print.aspx?matguid=dfc83225fec64437a9a3e9c7262badbe, (accessed Feb. 22, 2019).
Celanese CoolPoly® E1201 Thermally Conductive Polypropylene; Cool Polymers, Inc., 2014. http://www.matweb.com/search/datasheet_print.aspx?matguid=fb2b886d487d4d15b0abc3d619930ed3, (accessed Feb. 22, 2019).
Conduct of Proceeding For Inter Partes Review of U.S. Pat . No. 9,272,280 B2 dated Apr. 26, 2018, 3 pages.
Conduct of Proceeding For Inter Partes Review of U.S. Pat. No. 9,410,971 dated Apr. 26, 2018, 3 pages.
Conduct of Proceeding For Inter Partes Review of U.S. Pat. No. 9,410,971 dated Jul. 7, 2017, 7 pages.
Conduct of Proceeding For Inter Partes Review of U.S. Pat. No. 9,410,971 dated Mar. 9, 2018, 6 pages.
Conduct of Proceeding For Inter Partes Review of U.S. Pat. No. 9,410,971 dated May 24, 2018, 5 pages.
Conduct of Proceeding For Inter Partes Review of U.S. Pat. No. 9,410,971 dated May 5, 2017, 3 pages.
Decision Denying Petitioner's Request for Rehearing for Inter Partes Review of U.S. Pat. No. 9,410,971, entered Nov. 3, 2017, 7 pages.
Decision to Institute for Inter Partes Review of U.S. Pat. No. 9,915,671, dated Oct. 5, 2018, 27 pages.
Declaration of Patrick D. Mize, Ph.D., for Inter Partes Review of U.S. Pat. No. 9,272,280 dated Feb. 3, 2017, 83 pages.

Declaration of Patrick D. Mize, Ph.D., for Inter Partes Review of U.S. Pat. No. 9,410,971 dated Feb. 3, 2017, 124 pages.
Final Written Decision for Inter Partes Review of U.S. Pat. No. 9,272,280, dated Feb. 13, 2019, 25 pages.
Final Written Decision for Inter Partes Review of U.S. Pat. No. 9,410,9710, dated Feb. 13, 2019, 55 pages.
Fundamentals of biomechanics Equiolobrium, Motion, and Deformation. 2nd Edition. Eds. Nihat Özkaya and Margareta Nordin. (Springer Science + Business Media, Inc., New York, NY). Chapter 9 "Mechanical Properties of Biological Tissues." pp. 196-218. 1999.
Fundamentals of biomechanics Equiolobrium, Motion, and Deformation. 3rd Edition. Eds. Nihat Özkaya and Margareta Nordin. (Springer Science + Business Media, Inc., New York, NY). Chapter 15 "Mechanical Properties of Biological Tissues." pp. 221-236. 2012.
Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.
Janus TJ, Lewis SD, Lorand L, Shafer JA. Promotion of thrombin catalyzed activation of factor XIII by fibrinogen. Biochemistry. 1983; 22 (26): 6269-72.
Lang et al., "Evaluation of the new device ROTEM platelet" [retrieved on Dec. 28, 2015]. Retrieved from the Internet : <URL :https://www.rotem.de/wp-content/uploads/2014/09/Lang-et-al-2014.pdf>, Jan. 1, 2014.
Lang et al., "Multi-centre investigation on reference ranges of ROTEM thromboelastometry," Blood Coagulation and Fibrinolysis, 2005, 16: 301-310.
Lang et al., "Possibilities and limitations of thromboeleastometry/thromboelastography," Downloaded from www.haemostaseologieonline.com on Mar. 6, 2018 / IP: 24.163.60.123.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Libby G. Puckett et al. Monitoring blood coagulation with magnetoelastic sensors, Biosensors and Bioelectronics, vol. 18, Issues 5-6, 2003, pp. 675-681, ISSN 0956-5663.
Liu C, Mo YY, Chen ZG, Li X, Li OL, Zhou X. Dual fluorescence/contactless conductivity detection for microfluidic chip. Anal Chim Acta. Jul. 28, 2008;621(2):171-7. doi: 10.1016/j.aca.2008.05.040. Epub May 24, 2008. PMID: 18573381, (7 pages).
Niewiarowski S, Stewart GJ, Nath N, Sha AT, Lieberman Ge. Adp, thrombin, and Bothropsatrox thrombinlike enzyme in platelet dependent fibrin retraction. The American Journal of physiology. 1975; 229 (3): 737-45.
Patent Owner's Preliminary Response for Inter Partes Review for U.S. Pat. No. 9,272,280 dated Jun. 6, 2017, 34 pages.
Patent Owner's Preliminary Response for Inter Partes Review for U.S. Pat. No. 9,410,971 dated Jun. 7, 2017, 60 pages.
Patent Owner's Preliminary Response for Inter Partes Review for U.S. Pat. No. 9,915,671 dated Jul. 20, 2018, 14 pages.
Patent Owner's Preliminary Response to Petition Requesting Inter Partes Review of U.S. Pat. No. 9,410,971, dated Feb. 14, 2018, 33 pages.
Petition for Inter Partes Review For U.S. Pat. No. 9,915,671 dated Apr. 20, 2018, 76 pages.
Petition For Inter Partes Review of U.S. Pat. No. 9,272,280 B2, dated Feb. 27, 2018, 28 pages.
Petition For Inter Partes Review of U.S. Pat. No. 9,410,971 B2, dated Feb. 3, 2017, 51 Pages.
Petition For Inter Partes Review of U.S. Pat. No. 9,410,971 B2, dated Nov. 30, 2017, 74 pages.
Petition for Post-Grant Review of U.S. Pat. No. 10,031,144, dated Apr. 24, 2019, 104 pages.
Petition for Post-Grant Review of U.S. Pat. No. 9,977,039, dated Feb. 21, 2019, 95 pages.
Petitioner's Supplemental Reply For Inter Partes Review of U.S. Pat. No. 9,272,280 B2 dated May 18, 2018, 10 pages.
Rahe-Meyer, N. et al., Multicentric comparison of single portion reagents and liquid reagents for thromboelastometry. Blood Coagul Fibrinolysis Apr. 2009; 20 (3): 218-22. PubMed P.M.I.D.: 19657320.

(56)         References Cited

OTHER PUBLICATIONS

Ronalee Lo, Ellis Meng, Integrated and reusable in-plane microfluidic interconnects, Sensors and Actuators B: Chemical, vol. 132, Issue 2, 2008, pp. 531-539, ISSN 0925-4005.

ROTEM® delta, "Targeted therapy stops the bleeding," 6 pages, Jan. 6, 2014, [brochure].

Rugeri et al., "Diagnosis of early coagulation abnormalities in trauma patients by rotation thrombelastography," J Thromb Haemost., 5 (2): 289-295, Epub Nov. 16, 2006.

Stony Brook Portable Field Viscometer (For a quick 'Pass' or 'Fail' decision).

Tonal, B. Gutiérrez; de la Fuente Tornero, E.; Martínez, I. Garutti; Martínez, M. Villanueva; Huerta, A. Rodríguez Comparison of procoagulatory markers in function of anesthesic/analgesic technique used on the surgery of traumathology prosthesis replacement, European Journal of Anaesthesiology: May 2008—vol. 25—Issue—p. 84.

Van den Berg A., Lammerink T.S.J. (1998) Micro Total Analysis Systems: Microfluidic Aspects, Integration Concept and Applications. In: Manz A., Becker H. (eds) Microsystem Technology in Chemistry and Life Science. Topics in Current Chemistry, vol. 194. Springer, Berlin, Heidelberg. https://doi.org/10.1007/3-540-69544-3_2.

Viola, et al., "Sonorheometry: A new Method for Assessing coagulation potential," IEEE Ultrasonics Symposium, vol. 1, 2007, pp. 1001-1004.

Viola, et al., "Sonorheometry: A Noncontact Method for the Dynamic Assessment of Thrombosis," The Annals of Biomedical Engineering, vol. 32, 2004, pp. 696-705.

Viola, Francesco, et al., "A Novel Ultrasound-Based Method to Evaluate Hemostatic Function of Whole Blood," Clin Chim Acta, vol. 411, Nos. 1-2, 2010, pp. 106-113.

Weisel JW. The mechanical properties of fibrin for basic scientists and clinicians. Biophysical Chemistry. 2004; 112 (2-3): 267-276.

Weiss HJ, Aledort LM, Kochwa S., The effect of salicylates on the hemostatic properties of platelets in man. J Clin Invest. Sep. 1968; 47 (9): 2169-80.

Wolberg AS. Plasma and cellular contributions to fibrin network formation , structure and stability. Haemophilia. May 16, 2010: 7-12.

Decision Denying Institution of Inter Partes Review For Inter Partes Review of U.S. Pat. No. 9,410,971, dated May 10, 2018, 15 pages.

Decision Denying Petitioner's Motion to Withdraw Grounds For Inter Partes Review of U.S. Pat. No. 9,410,971, dated Jul. 11, 2018, 9 pages.

Decision Granting Patent Owner's Motion to Submit Supplemental Information For Inter Partes Review of U.S. Pat. No. 9,410,971, dated Jul. 11, 2018, 10 pages.

Decision Institution of Inter Partes Review For Inter Partes Review of U.S. Pat. No. 9,272,280 B2 dated Sep. 1, 2017, 13 pages.

Decision Institution of Inter Partes Review For Inter Partes Review of U.S. Pat. No. 9,410,971 dated Sep. 1, 2017, 27 pages.

Declaration of Frank M. Laduca, Ph.D., For Inter Partes Review of U.S. Pat. No. 9,915,671 dated Jan. 4, 2019, 37 pages.

Declaration of Frank M. Laduca, Ph.D., For Inter Partes Review of U.S. Pat. No. 9,977,039 dated Feb. 21, 2019, 117 pages.

Declaration of James P. Landers, For Inter Partes Review of U.S. Pat. No. 10,031,144 dated Jul. 29, 2019, 56 pages.

Declaration of James P. Landers, for Inter Partes Review of U.S. Pat. No. 9,977,039 dated May 28, 2019, 51 pages.

Declaration of John Avila for Inter Partes Review of U.S. Pat. No. 9,915,671, dated Jan. 4, 2019, 38 pages.

Declaration of Scott Diamond, Ph.D., for Inter Partes Review of U.S. Pat. No. 9,272,280 dated Dec. 1, 2017, 48 pages.

Declaration of Scott Diamond, Ph.D., for Inter Partes Review of U.S. Pat. No. 9,410,971 dated Dec. 1, 2017, 70 pages.

Declaration of Scott Diamond, Ph.D., for Inter Partes Review of U.S. Pat. No. 9,915,671 dated Apr. 20, 2018, 148 pages.

Declaration of Scott Diamond, Ph.D., for Inter Partes Review of U.S. Pat. No. 9,915,671 dated Apr. 20, 2018, 8 pages.

Deposition of Frank M. Laduca, Ph.D., for Inter Partes Review of U.S. Pat. No. 9,915,671 dated Feb. 13, 2019, 271 pages.

Deposition of John Avila for Inter Partes Review of U.S. Pat. No. 9,915,671, dated Feb. 5, 2019, 75 pages.

Deposition of Patrick D. Mize, Ph.D., for Inter Partes Review of U.S. Pat. No. 9,410,971 dated Oct. 5, 2017, 81 pages.

Deposition of Scott Diamond, Ph.D., for Inter Partes Review of U.S. Pat. No. 9,272,280 dated Jan. 18, 2018, 229 pages.

Deposition of Scott Diamond, Ph.D., for Inter Partes Review of U.S. Pat. No. 9,410,971 dated Jan. 18, 2018, 229 pages.

Deposition of Scott Diamond, Ph.D., for Inter Partes Review of U.S. Pat. No. 9,915,671 dated Apr. 26, 2019, 385 pages.

Deposition of Scott Diamond, Ph.D., for Inter Partes Review of U.S. Pat. No. 9,915,671 dated Nov. 15, 2018, 330 pages.

Grant of Good Cause Extension for Inter Partes Review of U.S. Pat. No. 9,272,280 B2 dated Aug. 28, 2018, 3 pages.

Grant of Good Cause Extension for Inter Partes Review of U.S. Pat. No. 9,410,971 dated Aug. 28, 2018, 3 pages.

Motion for Leave to File for Inter Partes Review of U.S. Pat. No. 9,272,280 B2 dated Jun. 26, 2017, 72 pages.

Notice of Filing Date for Inter Partes Review of U.S. Pat. No. 9,272,280 B2 dated Mar. 6, 2017, 5 pages.

Notice of Filing Date for Inter Partes Review of U.S. Pat. No. 9,410,971 dated Dec. 12, 2017, 4 pages.

Notice of Refund for Inter Partes Review of U.S. Pat. No. 9,410,971 dated Jun. 4, 2018, 2 pages.

Order Conduct of Proceeding for Inter Partes Review of U.S. Pat. No. 9,272,280 B2 dated Jul. 10, 2017, 7 pages.

Order Extending One-Year Pendency for Good Cause for Inter Partes Review of U.S. Pat. No. 9,272,280 B2 dated Aug. 28, 2018, 4 pages.

Order Supplemental Trial Hearing for Inter Partes Review of U.S. Pat. No. 9,272,280 B2 dated Aug. 6, 2018, 6 pages.

Order Trial Hearing for Inter Partes Review of U.S. Pat. No. 9,272,280 B2 dated Jun. 4, 2018, 6 pages.

Patent Owner's Mandatory Notices for Inter Partes Review of U.S. Pat. No. 9,272,280 B2, dated Feb. 23, 2017, 4 pages.

Patent Owner's Objection to Evidence for Inter Partes Review of U.S. Pat. No. 9,410,971, dated Sep. 18, 2017, 3 pages.

Patent Owner's Objection to Petitioner's Demonstrative Exhibits for Inter Partes Review of U.S. Pat. No. 9,272,280 B2, dated Aug. 10, 2018, 4 pages.

Patent Owner's Objection to Petitioner's Demonstratives for Inter Partes Review of U.S. Pat. No. 9,410,971, dated Aug. 10, 2018, 4 pages.

Patent Owner's Objection to Petitioner's Motion to Submit Supplemental Information for Inter Partes Review of U.S. Pat. No. 9,272,280 B2, dated May 30, 2018, 10 pages.

Patent Owner's Objection to Petitioner's Motion to Submit Supplemental Information for Inter Partes Review of U.S. Pat. No. 9,410,971, dated May 30, 2018, 10 pages.

Patent Owner's Objection to Petitioner's Motion to Withdraw Grounds for Inter Partes Review of U.S. Pat. No. 9,410,971, dated Jun. 8, 2018, 11 pages.

Patent Owner's Preliminary Response to Petition for Post Grant Review for Inter Partes Review of U.S. Pat. No. 10,031,144, dated Jul. 29, 2019, 51 pages.

Patent Owner's Preliminary Response to Petition for Post Grant Review for Inter Partes Review of U.S. Pat. No. 9,977,039, dated May 28, 2019, 53 pages.

Patent Owner's Request for Oral Argument for Inter Partes Review of U.S. Pat. No. 9,272,280 B2, dated Apr. 10, 2018, 3 pages.

Patent Owner's Request for Oral Argument for Inter Partes Review of U.S. Pat. No. 9,410,971, dated Apr. 10, 2018, 3 pages.

Patent Owner's Request for Supplemental Oral Hearing for Inter Partes Review of U.S. Pat. No. 9,272,280 B2, dated Aug. 3, 2018, 3 pages.

Patent Owner's Request for Supplemental Oral Hearing for Inter Partes Review of U.S. Pat. No. 9,410,971, dated Aug. 3, 2018, 3 pages.

Patent Owner's Sur-Reply for Inter Partes Review of U.S. Pat. No. 9,915,671, dated May 6, 2019, 34 pages.

(56) References Cited

OTHER PUBLICATIONS

Patent Owner's Updated Exhibit List for Inter Partes Review of U.S. Pat. No. 9,272,280 B2, dated Dec. 1, 2017, 3 pages.
Patent Owner's Updated Exhibit List for Inter Partes Review of U.S. Pat. No. 9,272,280 B2, dated Jun. 30, 2017, 2 pages.
Patent Owner's Updated Mandatory Notices for Inter Partes Review of U.S. Pat. No. 9,272,280 B2, dated Jun. 22, 2017, 4 pages.
Patent Owner's Updated Mandatory Notices for Inter Partes Review of U.S. Pat. No. 9,272,280 B2, dated Jun. 5, 2018, 4 pages.
Patent Owner's Updated Mandatory Notices for Inter Partes Review of U.S. Pat. No. 9,272,280 B2, dated Jun. 8, 2017, 4 pages.
Petitioner's Motion to Submit Supplemental Information for Inter Partes Review of U.S. Pat. No. 9,272,280 B2, dated May 22, 2018, 11 pages.
Petitioner's Objections to Patent Owner's Demonstratives for Inter Partes Review of U.S. Pat. No. 9,272,280 B2, dated Aug. 10, 2018, 6 pages.
Petitioner's Objections to Patent Owner's Demonstratives for Inter Partes Review of U.S. Pat. No. 9,272,280 B2, dated Jun. 8, 2018, 4 pages.
Petitioner's Supplemental Request for Oral Argument for Inter Partes Review of U.S. Pat. No. 9,272,280 B2, dated Aug. 2, 2018, 3 pages.
Petitioner's Updated Exhibit List for Inter Partes Review of U.S. Pat. No. 9,272,280 B2, dated Mar. 1, 2018, 4 pages.
Petitioner's Updated Mandatory Notices for Inter Partes Review of U.S. Pat. No. 9,272,280 B2, dated Jun. 8, 2018, 3 pages.
Record of Oral Hearing for Inter Partes Review of U.S. Pat. No. 9,272,280 B2 dated Aug. 14, 2018, 34 pages.
Record of Oral Hearing for Inter Partes Review of U.S. Pat. No. 9,272,280 B2 dated Jun. 12, 2018, 46 pages.
Reply Declaration of Scott Diamond, Ph.D., for Inter Partes Review of U.S. Pat. No. 9,915,671 dated Apr. 3, 2019, 19 pages.
Scheduling Order for Inter Partes Review of U.S. Pat. No. 9,272,280 B2 dated Sep. 1, 2017, 8 pages.
Curriculum Vitae for Patrick D. Mize, Ph.D., for Inter Partes Review of U.S. Pat. No. 9,272,280 dated Sep. 26, 2017, 4 pages.
Curriculum Vitae for Scott Diamond, Ph.D., for Inter Partes Review of U.S. Pat. No. 9,272,280 dated Jan. 9, 2018, 15 pages.
Curriculum Vitae for Scott Diamond, Ph.D., for Inter Partes Review of U.S. Pat. No. 9,410,971 dated Jan. 18, 2018, 15 pages.
Curriculum Vitae for Scott Diamond, Ph.D., for Inter Partes Review of U.S. Pat. No. 9,915,671 dated Apr. 15, 2019, 15 pages.
Decision Granting Patent Owner's Motion to Seal & Enter Jointly Proposed Protective Order for Inter Partes Review of U.S. Pat. No. 9,915,671, dated May 15, 2019, 6 pages.
Decision Granting Patent Owner's Motion to Submit Supplemental Information for Inter Partes Review of U.S. Pat. No. 9,915,671, dated Jun. 12, 2019, 8 pages.
*Instrumentation Laboratory Co. v. HemoSonics LLP*, for Inter Partes Review of U.S. Pat. No. 9,410,971, (IPR201700855 Conference Call Transcript), (PTAB May 22, 2018), 50 pages.
*Instrumentation Laboratory Co. v. HemoSonics LLP*, for Inter Partes Review of U.S. Pat. No. 9,410,971, (IPR201700855 Conference Call Transcript), (PTAB May 4, 2018), 72 pages.
Joint Request for Change of Oral Argument Location for Inter Partes Review of U.S. Pat. No. 9,915,671, dated Oct. 11, 2018, 2 pages.
Jointly Proposed Protective Order for Inter Partes Review of U.S. Pat. No. 9,915,671, dated Jan. 8, 2019, 14 pages.
Notice concerning Alternative Dispute Resolution Date for Inter Partes Review of U.S. Pat. No. 10,031,144, dated Apr. 29, 2019, 2 pages.
Notice of Deposition for Patrick D. Mize, Ph.D., for Inter Partes Review of U.S. Pat. No. 9,272,280 dated Sep. 26, 2017, 3 pages.
Notice of Deposition for Scott Diamond, Ph.D., for Inter Partes Review of U.S. Pat. No. 9,272,280 dated Jan. 9, 2018, 3 pages.
Notice of Deposition for Scott Diamond, Ph.D., for Inter Partes Review of U.S. Pat. No. 9,915,671 dated Apr. 15, 2019, 3 pages.

Notice of Filing Date for Inter Partes Review of U.S. Pat. No. 10,031,144, dated Apr. 29, 2019, 3 pages.
Notice of Filing Date for Inter Partes Review of U.S. Pat. No. 9,915,671, dated May 8, 2018, 5 pages.
Notice of Filing Date for Inter Partes Review of U.S. Pat. No. 9,977,039, dated Feb. 27, 2019, 5 pages.
Order Extending One-Year Pendency for Good Cause for Inter Partes Review of U.S. Pat. No. 9,410,971, dated Aug. 28, 2018, 3 pages.
Order Trial Hearing for Inter Partes Review of U.S. Pat. No. 9,915,671, dated Jun. 5, 2019, 6 pages.
Panel Change Order Conduct of the Proceeding for Inter Partes Review of U.S. Pat. No. 9,915,671, dated Jan. 10, 2019, 3 pages.
Patent Owner's Mandatory Notices For Inter Partes Review of U.S. Pat. No. 10,031,144, dated May 28, 2019, 4 pages.
Patent Owner's Mandatory Notices for Inter Partes Review of U.S. Pat. No. 9,410,971, dated Feb. 23, 2017, 4 pages.
Patent Owner's Mandatory Notices for Inter Partes Review of U.S. Pat. No. 9,915,671, dated May 10, 2018, 3 pages.
Patent Owner's Mandatory Notices for Inter Partes Review of U.S. Pat. No. 9,977,039, dated Mar. 7, 2019, 4 pages.
Patent Owner's Motion to Seal for Inter Partes Review of U.S. Pat. No. 9,915,671, dated Jan. 4, 2019, 14 pages.
Patent Owner's Motion to Submit Supplemental Information for Inter Partes Review of U.S. Pat. No. 9,915,671, dated May 21, 2019, 35 pages.
Patent Owner's Request for Oral Argument for Inter Partes Review of U.S. Pat. No. 9,915,671, dated Jun. 3, 2019, 3 pages.
Patent Owner's Updated Exhibit List for Inter Partes Review of U.S. Pat. No. 9,410,971, dated Dec. 1, 2017, 3 pages.
Patent Owner's Updated Exhibit List for Inter Partes Review of U.S. Pat. No. 9,410,971, dated Jun. 30, 2017, 2 pages.
Patent Owner's Updated Mandatory Notices for Inter Partes Review of U.S. Pat. No. 9,410,971, dated Jun. 22, 2017, 4 pages.
Patent Owner's Updated Mandatory Notices for Inter Partes Review of U.S. Pat. No. 9,410,971, dated Jun. 8, 2017, 3 pages.
Patent Owner's Updated Mandatory Notices for Inter Partes Review of U.S. Pat. No. 9,915,671, dated Jun. 8, 2018, 3 pages.
Pertinent Materials reviewed & considered by Scott Diamond, Ph.D., for Inter Partes Review of U.S. Pat. No. 9,272,280 dated Jan. 9, 2018, 2 pages.
Pertinent Materials reviewed & considered by Scott Diamond, Ph.D., for Inter Partes Review of U.S. Pat. No. 9,410,971 dated Jan. 18, 2018, 2 pages.
Pertinent Materials reviewed & considered by Scott Diamond, Ph.D., for Inter Partes Review of U.S. Pat. No. 9,915,671 dated Apr. 15, 2019, 2 pages.
Petitioner's Motion to Submit Supplemental Information for Inter Partes Review of U.S. Pat. No. 9,410,971, dated May 22, 2018, 11 pages.
Petitioner's Motion to Withdraw Grounds for Inter Partes Review of U.S. Pat. No. 9,410,971, dated Jun. 1, 2018, 6 pages.
Petitioner's Objection to Patent Owner's Demonstratives for Inter Partes Review of U.S. Pat. No. 9,410,971, dated Aug. 10, 2018, 6 pages.
Petitioner's Opposition to Patent Owner's Motion to Submit Supplemental Information for Inter Partes Review of U.S. Pat. No. 9,915,671, dated May 28, 2019, 71 pages.
Petitioner's Reply to Patent Owner's Objection to Motion to Withdraw for Inter Partes Review of U.S. Pat. No. 9,410,971, dated Jun. 15, 2018, 8 pages.
Petitioner's Reply to Patent Owner's Response for Inter Partes Review of U.S. Pat. No. 9,410,971, dated Mar. 1, 2018, 25 pages.
Petitioner's Reply to Patent Owner's Response for Inter Partes Review of U.S. Pat. No. 9,915,671, dated Apr. 4, 2019, 32 pages.
Petitioner's Request for Oral Argument for Inter Partes Review of U.S. Pat. No. 9,410,971, dated Apr. 23, 2017, 3 pages.
Petitioner's Request for Oral Argument for Inter Partes Review of U.S. Pat. No. 9,915,671, dated May 29, 2019, 3 pages.
Petitioner's Request for Refund for Inter Partes Review of U.S. Pat. No. 9,410,971, dated May 26, 2018, 3 pages.
Petitioner's Request for Rehearing for Inter Partes Review of U.S. Pat. No. 9,410,971, dated Sep. 15, 2017, 18 pages.

(56) References Cited

OTHER PUBLICATIONS

Petitioner's Supplemental Reply in view of Apr. 26, 2018 Institution of Previously Non-Instituted Grounds For Inter Partes Review of U.S. Pat. No. 9,410,971, dated May 18, 2018, 15 pages.
Petitioner's Updated Exhibit List for Inter Partes Review of U.S. Pat. No. 9,410,971, dated Mar. 1, 2018, 3 pages.
Response to Notice of Filing for Inter Partes Review for Inter Partes Review of U.S. Pat. No. 9,410,971, dated May 5, 2017, 7 pages.
Scheduling Order for Inter Partes Review of U.S. Pat. No. 9,410,971, dated Sep. 1, 2017, 8 pages.
Scheduling Order for Inter Partes Review of U.S. Pat. No. 9,915,671, dated Oct. 5, 2018, 8 pages.
Curriculum Vitae for Frank M. Laduca, Ph.D., for Inter Partes Review of U.S. Pat. No. 9,915,671 dated Jan. 30, 2019, 4 pages.
Curriculum Vitae for James P. Landers, for Inter Partes Review of U.S. Pat. No. 10,031, 144 dated May 28, 2019, 25 pages.
Curriculum Vitae for James P. Landers, for Inter Partes Review of U.S. Pat. No. 9,977,039 dated May 28, 2019, 25 pages.
EPO Communication Pursuant to Article 94(3) EPC for European Application No. 12865280.7, 4 pages as filed Oct. 8, 2018 for Inter Partes Review of U.S. Pat. No. 9,915,671.
Exhibit 1002 as filed for Inter Partes Review of U.S. Pat. No. 10,031,144 dated Oct. 2, 2018, 130 pages.
Exhibit 1003 as filed for Inter Partes Review of U.S. Pat. No. 10,031,144 dated Oct. 2, 2018, 472 pages.
Exhibit 1003 as filed for Inter Partes Review of U.S. Pat. No. 9,410,971 dated Dec. 1, 2017, 123 pages.
Exhibit 1003 as filed for Inter Partes Review of U.S. Pat. No. 9,977,039 dated May 28, 2019, 699 pages.
Exhibit 1009 as filed for Inter Partes Review of U.S. Pat. No. 9,272,280 dated Dec. 1, 2017, 907 pages.
Exhibit 1012 as filed for Inter Partes Review of U.S. Pat. No. 9,272,280 dated Jan. 26, 2017, 4 pages.
Exhibit 1020 as filed for Inter Partes Review of U.S. Pat. No. 9,410,972 dated Jul. 26, 2019, 7 pages.
Exhibit 1069 as filed for Inter Partes Review of U.S. Pat. No. 9,915,671 dated May 28, 2019, 1 page.
Exhibit 1074 as filed for Inter Partes Review of U.S. Pat. No. 9,915,671 dated May 28, 2019, 1 page.
IPR2018-00950 Papers as filed for Inter Partes Review of U.S. Pat. No. 9,915,671 dated May 28, 2019, 70 pages.
IPR2018-00950 Preliminary Amendment as filed for Inter Partes Review of U.S. Pat. No. 9,915,671 dated May 28, 2019, 34 pages.
Notice of Deposition for Frank M. Laduca, Ph.D., for Inter Partes Review of U.S. Pat. No. 9,915,671 dated Jan. 30, 2019, 3 pages.
Notice of Deposition for John Avila for Inter Partes Review of U.S. Pat. No. 9,915,671, dated Jan. 25, 2019, 3 pages.
Pertinent Materials reviewed & considered by James P. Landers, for Inter Partes Review of U.S. Pat. No. 10,031,144 dated May 28, 2019, 2 pages.
Pertinent Materials reviewed & considered by James P. Landers, for Inter Partes Review of U.S. Pat. No. 9,977,039 dated May 28, 2019, 2 pages.
Provisional Application as filed for Inter Partes Review of U.S. Pat. No. 9,977,039 dated May 28, 2019, 46 pages.
Response to EPO Communication Pursuant to Article 94(3) EPC for European Application No. 12865280.7, 13 pages as filed Feb. 18, 2019 For Inter Partes Review of U.S. Pat. No. 9,915,671.
User Manual (2007) for TEG 5000 Thrombelastograph Hemostasis System with TEG Analytical Software (TAS) Version 4.2.3 including 8 pages. an addendum (2008) for TEG Analytical Software (TAS) Version 4.3 (the "TEG 5000 User Manual"), 278 pages.
Extended European Search Report received for European Application No. 25171590.0, mailed on Oct. 8, 2025, 7 pages.

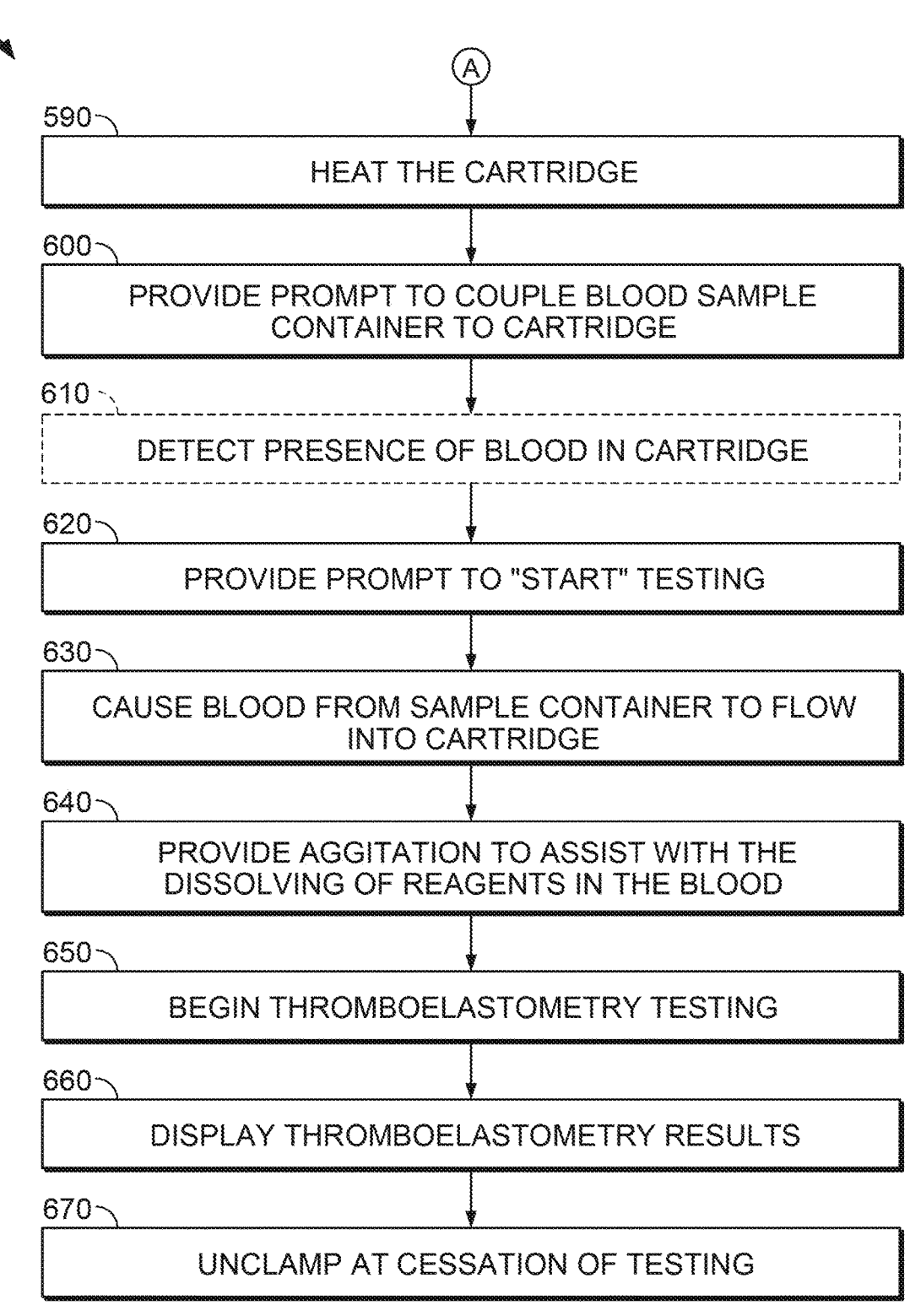

500

Ⓐ

590 — HEAT THE CARTRIDGE

600 — PROVIDE PROMPT TO COUPLE BLOOD SAMPLE CONTAINER TO CARTRIDGE

610 — DETECT PRESENCE OF BLOOD IN CARTRIDGE

620 — PROVIDE PROMPT TO "START" TESTING

630 — CAUSE BLOOD FROM SAMPLE CONTAINER TO FLOW INTO CARTRIDGE

640 — PROVIDE AGGITATION TO ASSIST WITH THE DISSOLVING OF REAGENTS IN THE BLOOD

650 — BEGIN THROMBOELASTOMETRY TESTING

660 — DISPLAY THROMBOELASTOMETRY RESULTS

670 — UNCLAMP AT CESSATION OF TESTING

FIG. 14B

BLOOD TESTING SYSTEM AND METHOD

CROSS REFERENCE TO RELATED APPLICATIONS

The present application is divisional application of Ser. No. 14/958,889, "Blood Testing System and Method," filed Dec. 3, 2015, which is a continuation in part of U.S. application Ser. No. 14/500,248, "Blood Testing System and Method," filed on Sep. 29, 2014, the entire disclosure of which are hereby incorporated by reference, in their entirety, for all purposes.

TECHNICAL FIELD

This document relates to systems and method for testing characteristics of a blood sample, such as an automated thromboelastometry system for point-of-care whole blood coagulation analysis.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of blood to form an adequate clot and to determine the blood clot's stability. Common laboratory tests such as thrombocyte counts or the determination of fibrin concentration provide information on whether the tested component is available in sufficient amount, but some of those tests might not answer the question of whether the tested component works properly under physiological conditions. Other laboratory tests work on blood plasma, which may impose additional preparation steps and additional time beyond what is preferred, for example, in the point-of-care context (e.g., in a surgical theater during a surgical operation).

Another group of tests to assess the potential of blood to form an adequate clot is known as "viscoelastic methods." In at least some viscoelastic methods, the blood clot firmness (or other parameters dependent thereon) is determined over a period of time, for example, from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction.

To isolate and test particular functions of thrombocytes, fibrinogen, and other factors in a blood sample, reagent compounds can be mixed with the blood sample to activate or inhibit certain components in the blood sample. In some commercially available point-of-care blood testing systems, liquid reagents are injected into a disposable plastic cup containing a blood sample, and the cup is then engaged by the control console of the blood testing system to evaluate characteristics of the coagulation/clotting of the blood sample. As part of the test process, the system requires manual intervention by the operator for each of the assays, for example, when pipettes are used by an operator for the dispensing and measuring of the reagents, blood, and mixed samples.

SUMMARY

Some embodiments of a system for testing characteristics of a blood sample (which, as used herein, should be understood to include blood or derivatives of blood such as plasma) can include a cartridge configured to mate with a control console and receive a blood sample for a point-of-care whole blood coagulation analysis. In particular circumstances, the cartridge is configured to interact with the control console so as to perform a number of automated transport and testing operations on portions of the blood sample so as to provide reliable and prompt results indicative of a patient's blood characteristics at the point-of-care (e.g., while the patient is in a surgical room undergoing surgery). For example, the system can serve as an automated thromboelastometry system for providing detailed and prompt results of blood coagulation characteristics in response to receiving a cartridge (and blood sample at the cartridge) and an indication from an operator to begin the automated testing process.

In some embodiments, the thromboelastometry system includes a reusable analyzer console and one or more single-use cartridge components configured to mate with the console. In one example, to operate the thromboelastometry system, a user inserts the cartridge into the analyzer console and, when prompted by the analyzer console, inserts a blood collection tube (containing a whole blood sample) into a receiver portion of the cartridge. The user is then prompted a user interface of the analyzer console to initiate a number of automated blood transfer and testing operations. Thereafter, the analyzer console automatically performs (without requiring further user interaction with the cartridge or the blood sample) the testing and displays the results on a graphical display using qualitative graphical representations and quantitative parameters. In this particular example, no manual pipetting, mixing, or handling of reagents by the user is needed. In some embodiments, four or more assays are automatically performed on the blood sample using a single cartridge device. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

Particular embodiments described herein include a cartridge for use with a blood testing console. The cartridge may include a blood sample receiver configured to receive a blood sample to be tested. The cartridge may also include one or more blood processing and testing paths. Each blood processing and testing path can receive a portion of the blood sample and may include a blood sample volume measurement chamber, a mixing chamber, and a viscoelastic blood testing chamber. The blood sample volume measurement chamber may be in fluid communication with the blood sample receiver, and the blood sample volume measurement chamber may a selected internal volume to contain a predetermined volume of blood sample from the blood sample container. The mixing chamber may be in fluid communication with the blood sample volume measurement chamber and with a reagent, and the mixing chamber may be configured to receive blood sample from the blood sample volume measurement chamber and mix the received blood with the reagent. The viscoelastic blood testing chamber may be configured to receive mixed blood and reagent from the mixing chamber for a viscoelastic test to be performed on the mixed blood and reagent while the mixed blood and reagent resides in the testing chamber.

In some embodiments described herein, a cartridge device may include a blood sample receiver, and a plurality of blood sample pathways in selective fluid communication with the blood sample receiver. Each blood sample pathway may include: a blood measurement chamber to receive a predetermined amount of a blood sample via the blood sample receiver, a reagent mixing chamber for receiving and mixing the predetermined amount of the blood sample with one or more reagents, and a blood coagulation blood testing chamber for receiving from the reagent mixing chamber the blood sample with one or more reagents mixed therewith. Optionally, the blood coagulation blood testing chamber may have a movable probe therein for measuring blood coagulation characteristics.

Various embodiments described herein include a cartridge device for a measuring system for measuring viscoelastic characteristics of a blood sample. The cartridge may include a blood sample receiver; and at least one blood sample pathway in selective fluid communication with the blood sample receiver. The blood sample pathway may include: a blood measurement chamber configured to be filled with a predetermined amount of a blood sample via the blood sample receiver, a reagent mixing chamber for receiving the predetermined amount of the blood sample from the blood measurement chamber and for and mixing the predetermined amount of the blood sample with one or more reagents, and a blood coagulation blood testing chamber for receiving from the reagent mixing chamber the blood sample with one or more reagents mixed therewith, and an overflow chamber in fluid communication with the blood sample pathway so as to collect excess blood from the blood measurement chamber beyond the predetermined amount the blood sample. Optionally, the blood coagulation blood testing chamber may have a movable probe therein for measuring blood coagulation characteristics.

Other embodiments described herein include a measuring system for measuring viscoelastic characteristics of a blood sample. The system may include a control unit housing viscoelastic measurement components. The control unit may define an exterior port. The system may also include at least one disposable cartridge comprising a blood sample input accessible along an exterior of the cartridge and a plurality of blood testing chambers positioned along an interior of the cartridge. Optionally, the control unit is configured to releasably mate with the disposable cartridge when inserted into the exterior port such that the blood sample input of the cartridge remains external to the control unit while the plurality of blood testing chambers are positioned within the control unit.

Some embodiments described herein include a method of using a system for measuring viscoelastic characteristics of a blood sample. The method may include inserting a disposable cartridge into a blood testing control console such that a blood sample input remains externally exposed. The method may also include attaching a blood sample reservoir to the blood sample input. The method may further include providing user input via a user interface of the blood testing control console so as to initiate an automated transport of blood in the blood sample reservoir to a plurality of blood testing chambers within the cartridge for measuring viscoelastic characteristics of the blood in each of the blood testing chambers.

In particular embodiments described herein, a cartridge device for a measuring system for measuring viscoelastic characteristics of a blood sample may include a blood sample receiver structure defining a cavity configured to releasably mate with a blood sample reservoir container. The cartridge device may also include a plurality of blood testing chambers spaced apart from the blood sample receiver structure and each having a movable probe therein for measuring blood coagulation characteristics. All of the blood testing chambers may be in selective fluid communication the blood sample receiver structure.

In some embodiments described herein, a cartridge device for a measuring system for measuring viscoelastic characteristics of a blood sample may include a plurality of blood testing chambers for measuring blood coagulation characteristics. Each of the blood testing chambers may be exposed to atmosphere and may have a sample input port positioned along a sidewall of the blood testing chamber. Optionally, each of the blood testing chambers is in fluid communication with an output port of a respective reagent mixing chamber that is defined in cartridge device at a height below the sample input port of the blood testing chamber.

In various embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a plurality of retaining elements extending into the reagent mixing chamber so as to maintain a predetermined vertical position of each of the reagent mixing beads within the mixing chamber. The retaining elements of at least one of the reagent mixing chambers may engage multiple reagent mixing beads to maintain the multiple reagent mixing beads spaced apart from one another.

In particular embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a movable mixing element retained with the reagent mixing chamber. The movable mixing element may comprise a material that is inert relative to the blood sample. The cartridge device may further include a plurality of retaining elements extending into the reagent mixing chamber so as to maintain the reagent mixing beads in positions that are spaced apart from the movable mixing element.

Some embodiments described herein may include a method for measuring coagulation characteristics of a blood sample. The method may include detecting a blood testing cartridge being inserted into a receiver portion of a blood testing control unit. The method may also include prompting a user for input via a user interface of the blood testing control unit to initiate automated transport of blood in the blood sample reservoir to one or more blood testing chambers within the cartridge for measuring viscoelastic characteristics of the blood in each of the blood testing chambers. The method may further include automatically transporting to each of the one or more blood testing chambers within the cartridge a predetermined amount of a blood sample from a blood sample receiver of the blood testing cartridge. Optionally, the method may also include moving a probe in each respective blood testing chamber of the cartridge for measuring blood coagulation characteristics. The method may further include displaying via the user interface measurement results of the blood coagulation characteristics.

Other embodiments described herein include a control console for measuring coagulation characteristics of a blood sample. The control console may include a control unit housing that houses at least one interface element configured to releasably receive a disposable cartridge (which, optionally, may have multiple blood testing chambers therein, and multiple measurement components configured to measure coagulation characteristics of the blood sample within the multiple blood testing chambers of the disposable cartridge). The control console may also include one or more heating elements positioned proximate to the interface element and configured to heat the cartridge to a predetermined, test-related temperature (e.g., 37 degrees C. in some embodiments). The control console may further include one or more temperature sensors positioned proximate to the interface element. The control unit may be configured to transport blood to the multiple blood testing chambers of the disposable cartridge after the temperature sensors indicate the multiple blood testing chambers of the disposable cartridge have reached a predefined temperature.

Some or all of the embodiments described herein may provide one or more of the following advantages. First, some embodiments of the thromboelastometry system are configured to be automated so that user interactions with the system are minimized. As a result, human resources—especially in a point-of-care context like a surgical theater—can be utilized with greater efficiency. The reduction of user interactions can also reduce the chances for manual operator errors, such as measuring inaccuracies, reagent mixing errors, and the like. Accordingly, more accurate thromboelastometry results may be attained in some circumstances.

Second, in some embodiments, the cartridge component includes multiple fluid channels that are each individually controllable so that multiple different assays can be performed from a single supply of a blood sample. For example, each fluid channel includes a dedicated valve and a dedicated vent that are controllable by the analyzer console so that the blood flow and testing of each fluid channel is individually controllable. This feature enables the thromboelastometry system to automatically perform sophisticated assay processes.

Third, in some embodiments, the analyzer console can be configured to perform a number of quality-control operations/confirmations so as to ensure the blood test results are not compromised. For example, the analyzer console can be configured to verify the blood testing cartridge is heated to a target temperature (e.g., about 37° C.) prior to the blood sample being distributed to testing chambers of the cartridge. Because temperature of the blood sample can affect the coagulation characteristics in some circumstances, the accuracy of the thromboelastometry results may be enhanced as a result of such temperature-control operations/confirmations.

Forth, in particular embodiments of the cartridge device, the geometry of the blood flow paths through the fluid channels of the cartridge are configured to reduce the potential for disturbing the blood (e.g., causing bubble formation, etc.), and/or damaging the blood, in a manner that may negatively impact the accuracy of the blood test results.

Fifth, in some embodiments, the blood testing cartridge (and, optionally, the blood collection reservoir) can be equipped with one or more computer-readable components so as to promptly transfer relevant information of the analyzer console for each blood sample testing cycle. For example, each cartridge can be labeled with a barcode, near-field communication tag, and RFID tag, or the like that includes information such as, but not limited to, the types of assays to be performed by the cartridge, the type of reagents container within the cartridge, manufacturer information, an expiration date, or the like. In such embodiments, the analyzer console can include a barcode reader (or a reader for a near-field communication tag, a RFID tag, or the like) that scans the barcode upon insertion of the cartridge into the analyzer console. The analyzer console automatically performs appropriate actions in response to the data read from the barcode. In another example, each blood collection reservoir that is to be used with a corresponding cartridge can be labeled with a barcode, near-field communication tag, and RFID tag, or the like that includes information such as, but not limited to, patient information, clinician information, calibration information, or the like (e.g., which is readable by a corresponding reader device of the analyzer console).

Sixth, each fluid pathway of the cartridge can include a mixing chamber with one or more reagents and a mixing element located therein. In some embodiments, the reagents comprise dissolvable reagent beads. The mixing chambers of the cartridge can be configured to separate the one or more reagent beads from each other and to inhibit the mixing element from direct contact with the reagent beads. Further advantages associated with the thromboelastometry systems provided herein are also envisioned, as will be evident from the following disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 14A and 14B are a flowchart of a method for controlling a thromboelastometry system, in accordance with some embodiments.

Like reference symbols in the various drawings indicate like elements.

DETAILED DESCRIPTION OF ILLUSTRATIVE EMBODIMENTS

Figures 1A, 1B:
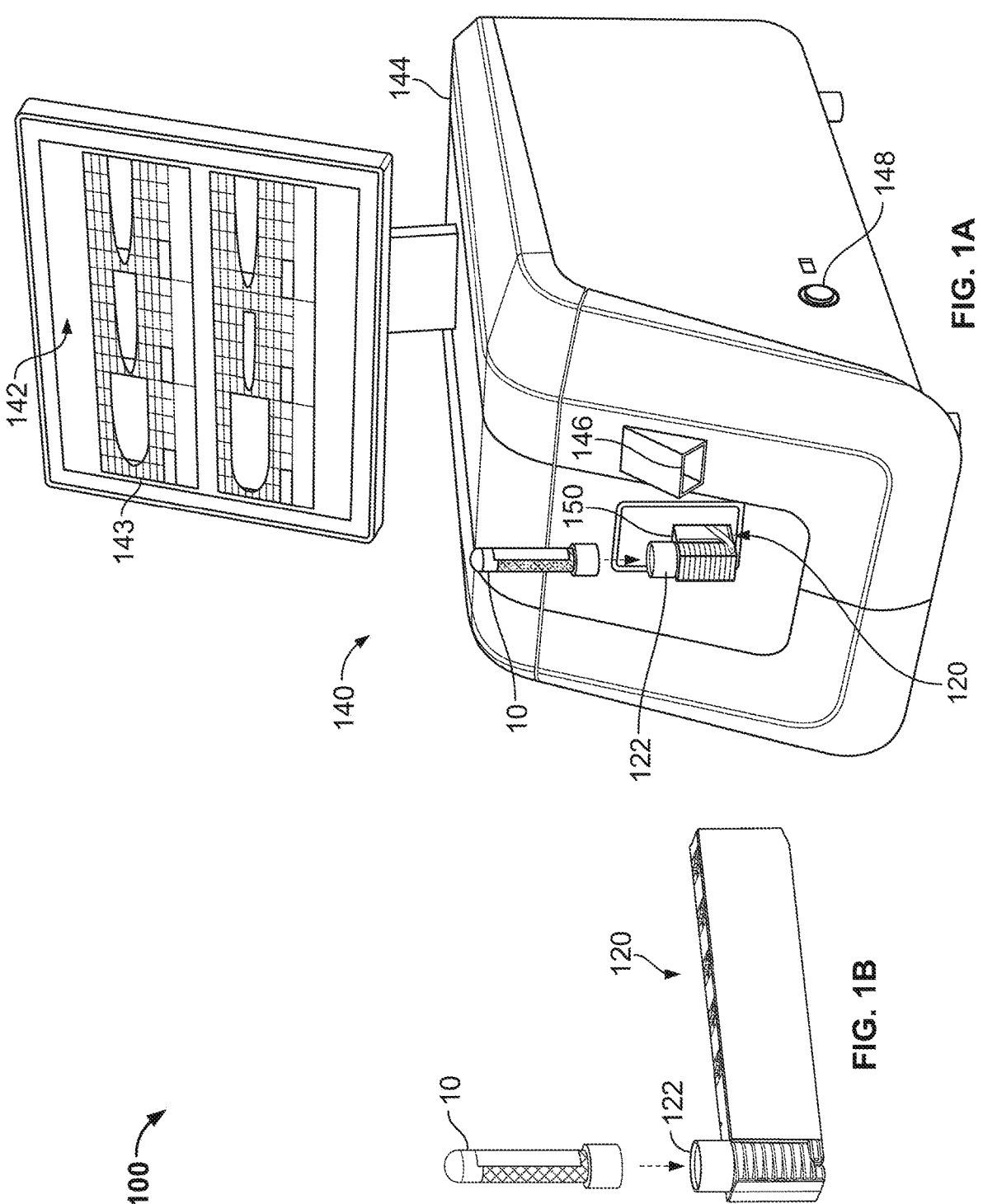
FIGS. 1A, 1B, 2, and 3 are perspective illustrations depicting the components and use of an example thromboelastometry system, in accordance with some embodiments.

Referring to FIGS. 1A-3, some embodiments of a blood testing system 100 include an analyzer console 140 and one or more cartridges 120 configured to releasably mate with analyzer console 140. In this embodiment, the blood testing system 100 is a thromboelastometry system that is configured to determine a number of blood coagulation characteristics of a blood sample input into the cartridge 120. For example, the cartridge 120 can be configured as a single-use cartridge that includes a blood sample receiver 122 for mating with a blood sample reservoir 10 (e.g., a vacutainer sample tube supplied by Becton, Dickinson & Company of Franklin Lakes, N.J., or another blood reservoir structure). In some cases, an adapter may be used to couple other types of blood sample reservoirs 10 with the cartridge 120 (e.g., tubing may be used through which blood can be injected into the cartridge 120, and the like). The thromboelastometry system 10 can be used as a whole blood coagulation analysis system that is particularly advantageous at a point-of-care site (e.g., in a surgical theater while a patient is undergoing or preparing for surgery, or the like). Additionally, thromboelastometry system 100 can be used as a whole blood coagulation analysis system in a laboratory setting.

The analyzer console 140 includes a user interface 142 (with touchscreen display in this embodiment) and a main chassis 144. The user interface display 142 can be configured to output one or more graphical results 143 from the blood testing assays performed via the cartridge 120 and console 140 (e.g., one or more plots, such as those sometimes refer to as a TEMogram, numeric data or measurements, or a combination thereof). In some embodiments, the user interface display 142 is rigidly attached to the analyzer console 140. In particular embodiments, the user interface display 142 is pivotable and/or is otherwise positionally adjustable in relation to the main chassis 144. A main power switch 148 can be located at a convenient but protected location on the main chassis 144.

In the depicted embodiment, the touchscreen display 142 is configured to receive user input and to display output information to the user. For example, the user can enter information to the thromboelastometry system 100 by making selections of various soft-buttons that may be displayed on the touchscreen display 142 at times during the beginning, middle, and end of the testing process. In some embodiments, other selections such as, but not limited to, soft keyboard entries can be provided via touchscreen display 142. In some embodiments, data entry can be performed additionally or alternatively by voice entry. In other embodiments, the user interface may include other peripheral devices can be included (e.g., a mouse, a keyboard, an additional display device, and the like) as part of the thromboelastometry system 100. In some embodiments, a computer data network (e.g., intranet, internet, LAN, etc.) may be used to allow for remote devices to receive and/or input information from the system 100. For example, in some embodiments one or more remote displays can be utilized via network connections. In the depicted embodiment, the thromboelastometry system 100 also includes an external barcode reader 146. The external barcode reader 146 can facilitate convenient one-dimensional or two-dimensional barcode entry of data such as, but not limited to, blood sample data, user identification, patient identification, normal values, and the like. Alternatively or additionally, the thromboelastometry system 100 can be equipped with a reader configured to read near-field communication tags, RFID tags, or the like.

In the depicted embodiment, the main chassis 144 houses various internal sub-systems (as described further below), includes various electronic connection receptacles (not shown), and includes a cartridge port 150. The various electronic connection receptacles can include network and device connectors such as, but not limited to, one or more USB ports, Ethernet ports (e.g., RJ45), VGA connectors, Sub-D9 connectors (RS232), and the like. Such connection receptacles can be located on the rear of the main chassis 144, or at other convenient locations on the main chassis 144. For example, in some embodiments one or more USB ports may be located on or near the front of the main chassis 144. A USB port, so located, may provide user convenience for recording data onto a memory stick, for example. In some embodiments, the thromboelastometry system 100 is configured to operate using wireless communication modalities such as, but not limited to, Wi-Fi, Bluetooth, NFC, RF, IR, and the like.

Still referring to FIGS. 1A-3, the cartridge port 150 can be located at a readily accessible location on the main chassis 144. In the depicted embodiment, the cartridge port 150 is located on the front of the main chassis 144 so that it is conveniently accessible by a user in a point-of-care site. The cartridge port 150 defines an opening and internal space that is shaped complementarily to the outer dimensions of the single-use cartridge 120. To insert the single-use cartridge 120 into the cartridge port 150, the user can grasp the end of the cartridge 120 that includes the blood sample receiver 122 and slidingly insert the opposite end (leading end) into the cartridge port 150. The sliding insertion can continue until a hard-stop is reached that defines the fully inserted position. In the fully inserted position, a trailing end portion (including the blood sample receiver 122 in this embodiment) of the single-use cartridge 120 remains exterior to the main chassis 144. The portion of the cartridge 120 that is received into the cartridge port 150 can include outer surface features (such as a tapered angle a rear end portion shown in FIG. 1B) that mate with at least one internal interface element inside the console 140 to ensure correct positioning of the cartridge 120. As such, at least the blood sample receiver 122 remains exterior to the main chassis 144 throughout the duration of the blood sample testing. In this configuration, the blood sample receiver 122 serves as a blood sample well that is accessible so that the blood sample reservoir 10 can be inserted into the receiver 122 while the single-use cartridge 120 is mated with the console 140 in the fully inserted position. In some embodiments, the cartridge port 150 and the main chassis 144 are configured so that the exposed portion of the cartridge 120 is protected from inadvertent contact. As described further below, an internal sensor (e.g., a microswitch, an optical sensor, etc.) can detect when the single-use cartridge 120 has been fully inserted into the main chassis 144.

When the analyzer console 140 has detected that the cartridge 120 has been fully inserted, in some embodiments the analyzer console 140 initiates one or more of the following actions. An internal cartridge clamping mechanism that includes positioning pins can be activated to accurately position and releasably retain the single-use cartridge 120 in the fully inserted position. One or more cartridge heating elements can be nalactivated to warm the cartridge 120. The temperature of the cartridge 120 can be monitored. A barcode on the leading end of the cartridge 120 can be read and the barcode data can be stored in memory of the analyzer console 140. One or more blood detection sensors can inspect the cartridge 120 for the presence of blood (which should not be present at this time). The rotational thromboelastometry measuring sub-system can be engaged with the cartridge 120 and, optionally, rotation of the rotary thromboelastometry measuring sub-system can begin (without the presence of blood). The cartridge 120 can be leak tested using vacuum or air pressure delivered by the analyzer console 140. For example, a pressure/vacuum decay test can be performed. In some embodiments, other actions can be additionally or alternatively activated when the analyzer console 140 has detected that the cartridge 120 has been fully inserted. After the completion of such actions, in some embodiments an indication of the results of the actions may be displayed on the touchscreen display 142 (e.g., pass or fail). If the analyzer console 140 determines that the actions were completed successfully, a prompt can be provided on the touchscreen display 142 that informs the user that the thromboelastometry system 100 is ready to receive the blood sample reservoir 10.

Briefly, in some embodiments a user can operate the depicted thromboelastometry system 100 embodiment as follows. First, the user can insert the single-use cartridge 120 into the cartridge port 150 so that the cartridge 120 is placed into the fully inserted position. Completion of that step will automatically initiate a series of operations by the thromboelastometry system 100 as described below. Upon successful completion of such operations, a notification that the blood collection tube 10 can be inserted into the sample well 122 will be displayed on the touchscreen display 142. After the user has mated the blood collection tube 10 into the sample well 122, the user initiates testing by pressing a "start" button (or the like) on the touchscreen display 142. At least the blood measuring, reagent mixing, and thromboelastometry testing is performed automatically by the system 100 thereafter (e.g., without requiring manual intervention from the user in this embodiment). When the testing is completed, the results are displayed on the touchscreen display 142 in the form of qualitative graphical representations and quantitative parameters (e.g., as depicted in FIG. 1A). Also, when the testing is completed, the cartridge 120 can be removed from the console 140 and discarded (e.g., the cartridge 120 in such embodiments is not reusable in that the reagent beads (described below) are no longer present in the cartridge and the measurement chambers contain the clotted blood sample portions).

Alternately, in some embodiments the blood collection tube 10 can be inserted into the sample well 122 of the cartridge 120 prior to insertion of the cartridge 120 into the cartridge port 150. In such circumstances, the blood from the collection tube 10 may not advance to the measurement chambers (described below) of the blood cartridge 120 until after the console 140 acts upon the cartridge 120 (again, as described below). With the blood collection tube 10 being pre-coupled with the cartridge 120, the combination of the blood collection tube 10 and the cartridge 120 can then be inserted into the cartridge port 150.

Figures 4, 5:
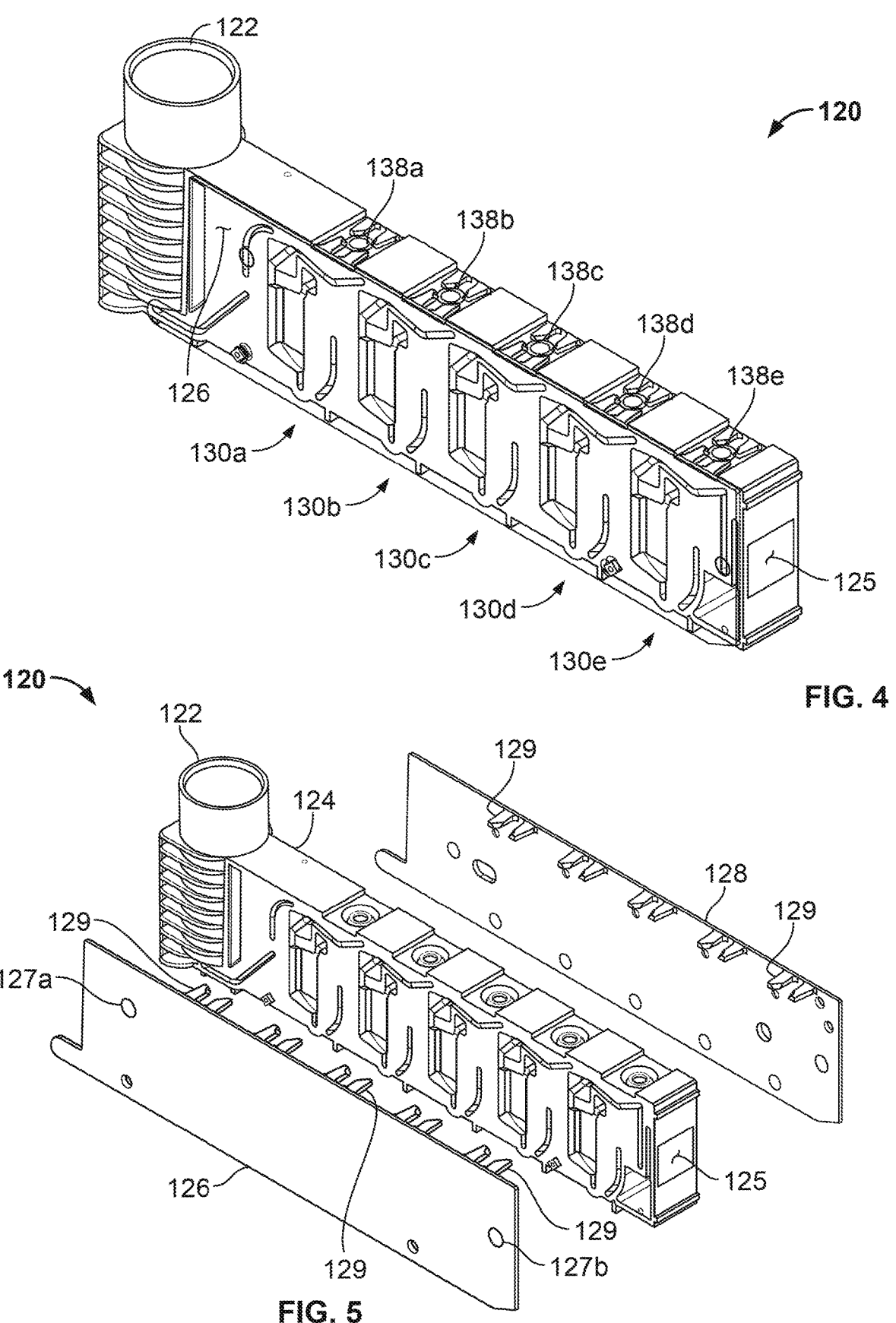
FIG. 4 is a perspective view of the example cartridge component of the thromboelastometry system of FIGS. 1A, 1B, 2, and 3.
FIG. 5 is an exploded view of the cartridge component of FIG. 4.

Referring now to FIGS. 4 and 5, the depicted embodiment of the single-use cartridge 120 includes a main body 124, a right cover 126, a left cover 128, and five pins 138*a*, 138*b*,

138*c*, 138*d*, and 138*e*. The right cover 126 is affixed to right side of the main body 124, and the left cover 128 is affixed to the left side of the main body 124. As such, the right and left covers 126 and 128 enclose cavities and flow channels of the main body 124 to define blood flow paths as described further below. The aforementioned sample well 122 is part of the main body 124. However, other constructions of the single use cartridge 120 are also envisioned.

In some embodiments, the main body 124, right cover 126, left cover 128, and the pins 138*a*, 138*b*, 138*c*, 138*d*, and 138*e* are made by injection molding. After molding, the right and left covers 126 and 128 can be affixed to the main body 124 using various techniques including, but not limited to, ultrasonic welding, laser welding, solvent bonding, adhesive bonding, UV curable adhesive bonding, and the like. Various polymeric materials can be used to construct the main body 124, right cover 126, left cover 128, and pins 138*a-e*. For example, such polymeric materials can include, but are not limited to acrylic, polycarbonate, polyvinyl chloride (PVC), polyethylene, polypropylene, polymethyl methacrylate, polystyrene, acrylonitrile butadiene styrene (ABS), polyethylene, polypropylene, and the like, and combinations thereof. In some embodiments, the materials are used to construct the main body 124, right cover 126, left cover 128, and pins 138*a-e* comprise an acrylic-based multi-polymer compound. In some embodiments, the main body 124, right cover 126, and left cover 128 are essentially transparent, or at least translucent. Therefore, in FIG. 4, features of the main body 124 are visible even though the right cover 126 is attached thereto.

Figure 7:
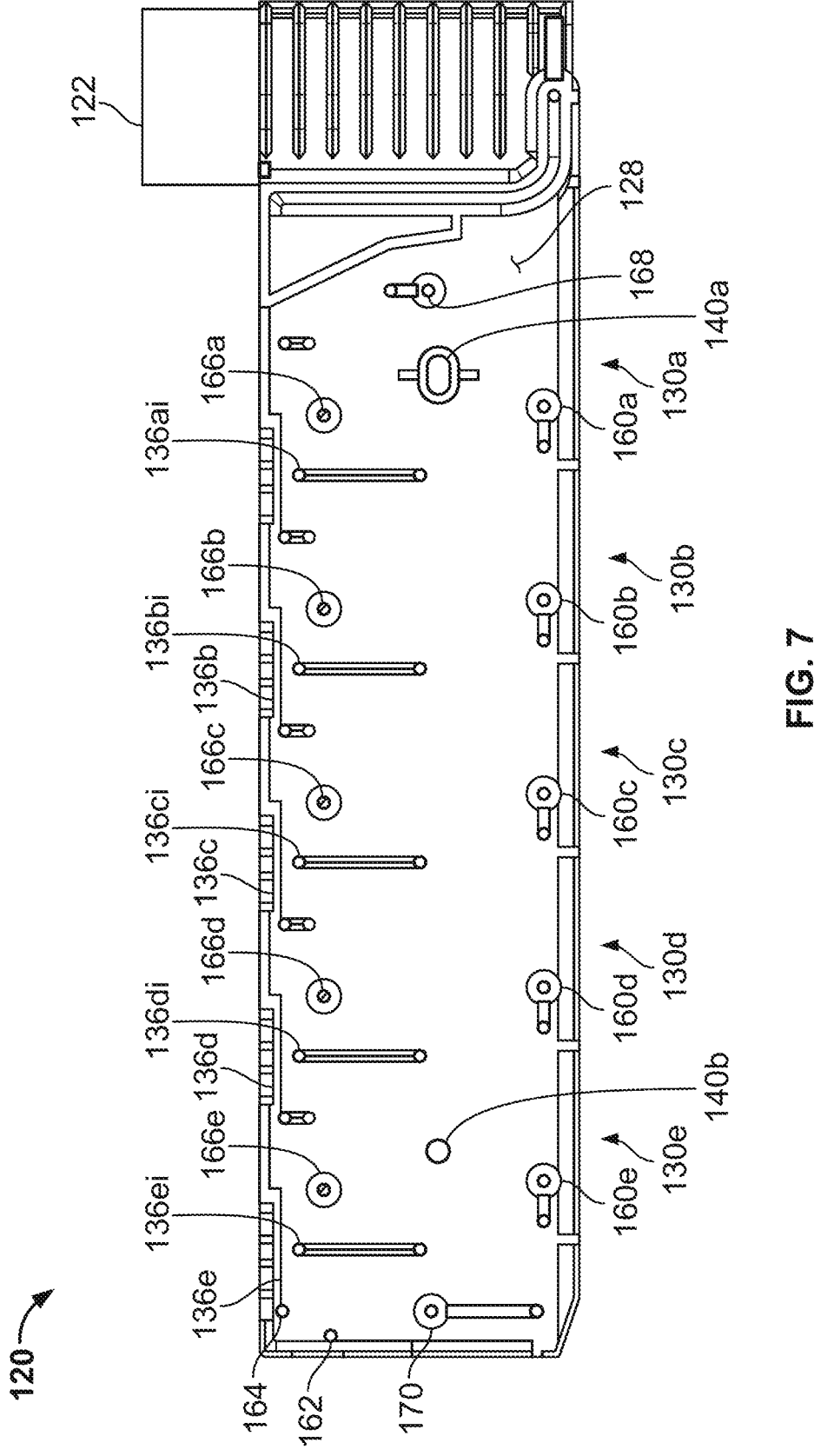
FIG. 7 is a left side view of the cartridge component of FIG. 4.

In some embodiments, overmolding, such as by insert molding or multi-shot molding techniques, may be used to construct some aspects of the main body 124, right cover 126, and/or left cover 128 (i.e., a device component). For example, elastomeric valve elements (as described further below) may be overmolded in the left cover 128. To generate valves by overmolding, a first mask is used to generate a device component without valves. The mask is an inverse of the shape of the device component, the device component including open spaces for later insertion of valves. A polymer is poured into the first mask to form a hard plastic device component. Then a second mask having the inverse of the shape of the device component with the valves is provided. The hardened plastic device component is placed in the mask, and an elastomeric material is injected into the open spaces formed in the device component by the first mask, thereby forming elastomeric valves in the device component. In some embodiments, the device component is the main body 124, right cover 126, and/or left cover 128. Exemplary valves 160*a-e*, 168, and 170 in a left cover 128 formed by overmolding are shown in FIG. 7. In some embodiments, the valves comprise an elastomeric material, deformable upon application of pressure. Deformation of the valves by application of external pressure pushes the elastomeric material into the duct, thereby fluidically sealing the duct to prevent flow of a sample liquid through the duct.

Further, in some embodiments secondary operations may be performed to the cartridge 120. For example, one or more needles 123*a-b* (refer to FIG. 6) for piercing a blood collection tube may be installed within the sample well 122 using secondary operations.

The single-use cartridge 120 also includes the five pins 138*a*, 138*b*, 138*c*, 138*d*, and 138*e*. The pins 138*a-e* are individual component parts (e.g., refer to FIG. 10B) that are retained within openings of the main body 124 (e.g., within testing chambers 136*a-e* (sometimes referred to as "cups") as described further below in connection with FIGS.

Figure 10A:
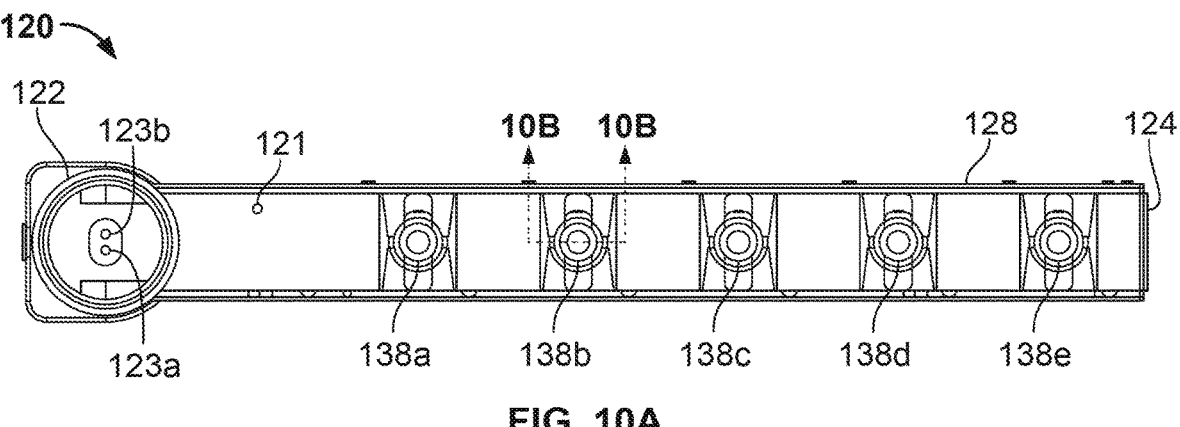
FIG. 10A is a top view of the cartridge component of FIG. 4.
Figure 10B:
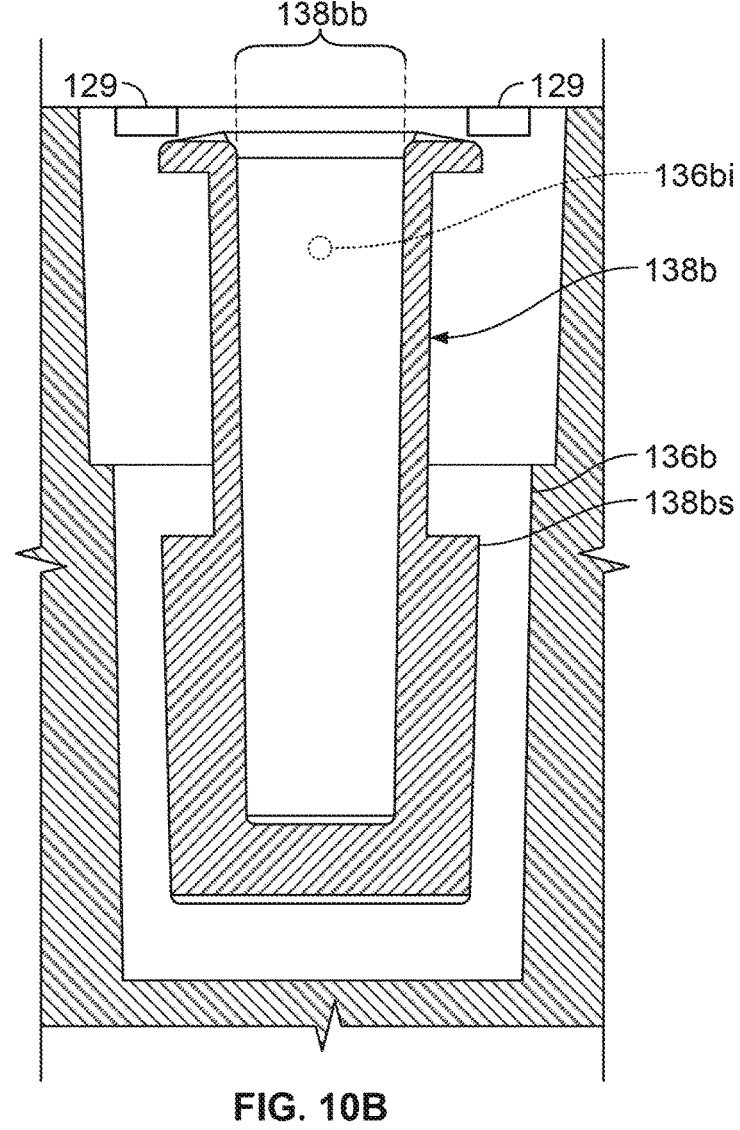
FIG. 10B is a partial cross-sectional view of the cartridge component of FIG. 10A.
Figure 10C:
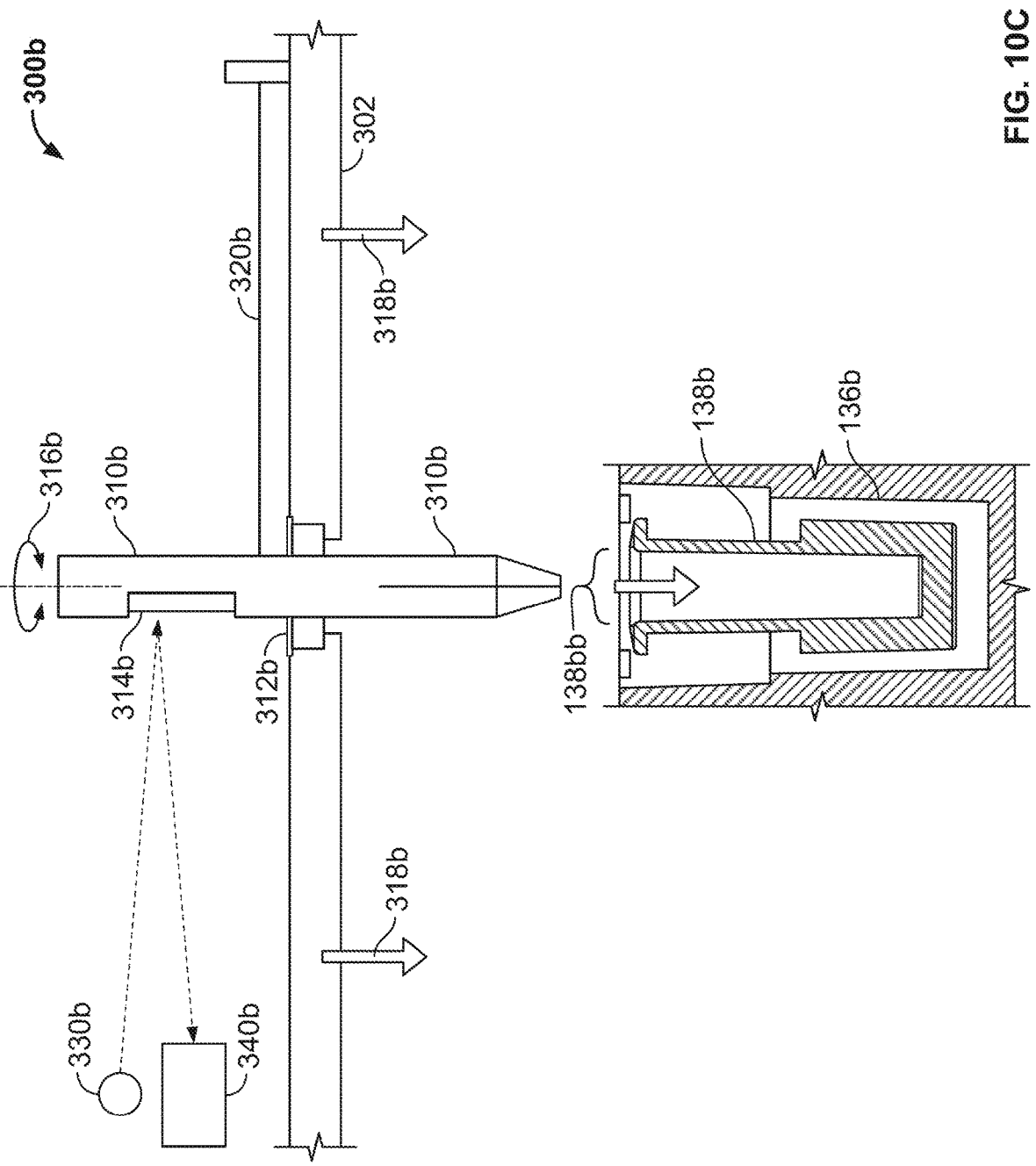
FIG. 10C is a schematic diagram depicting the partial cross-sectional view of the cartridge component of FIG. 10B in conjunction with associated components of an analyzer console of the thromboelastometry system of FIGS. 1A, 1B, 2, and 3.

8A-10B). Tabs 129, located on the right and left covers 126 and 128, mechanically retain the pins 138*a-e* in the main body 124. However, the pins 138*a-e* are free to move within the confines of the main body 124 to a limited extent. For example, the pins 139*a-e* are free to rotate uninhibitedly within the main body 124 and to translate vertically by few millimeters. This configuration of the pins 138*a-e* in relation to the other components of the cartridge 120 can be created as follows. Prior to affixing the right and left covers 126 and 128 to the main body 124, the pins 138*a-e* can be placed within their respective locations in the main body 124 as shown in FIG. 5. With the pins 138*a-e* positioned in the main body 124, the right and left covers 126 and 128 can then be affixed to the main body 124. With the right and left covers 126 and 128 affixed to the main body and the pins 138*a-e* positioned in the main body 124, the pins are secured in place vertically by the tabs 129 over the top of the pin 138*a-e* such that they cannot fall out or be removed from the cup 136*a-e* without removal of the right and left covers 126 and 128 from the main body 124. The tabs 129 allow free rotational movement of the pin 138*a-e*, as well as sufficient vertical motion to allow the pin 138*a-e* to interact with a fluid sample to perform a measurement of viscoelastic characteristics of a fluid sample in the cup 136*a-e*, e.g., rotational thromboelastometry. In addition, the tabs 129 provide an opening for a shaft 310*b* to couple with a pin 138*b*, as shown in FIG. 10C. In one example, the right and left covers 126 and 128 are affixed to the main body 124 and thereafter the pins 138*a-e* are pushed into the main body 122 past the tabs 129. The tabs 129 of the right and left covers 126 and 128 will block the pins 138*a-e* from falling out of the main body 122, even if the cartridge 120 is turned upside down. In some embodiments, the pin and tabs are positioned to prevent escape of semi-coagulated fluid sample in the testing chamber from escaping the testing chamber, even if the cartridge 120 is turned upside down.

Figures 2, 3:
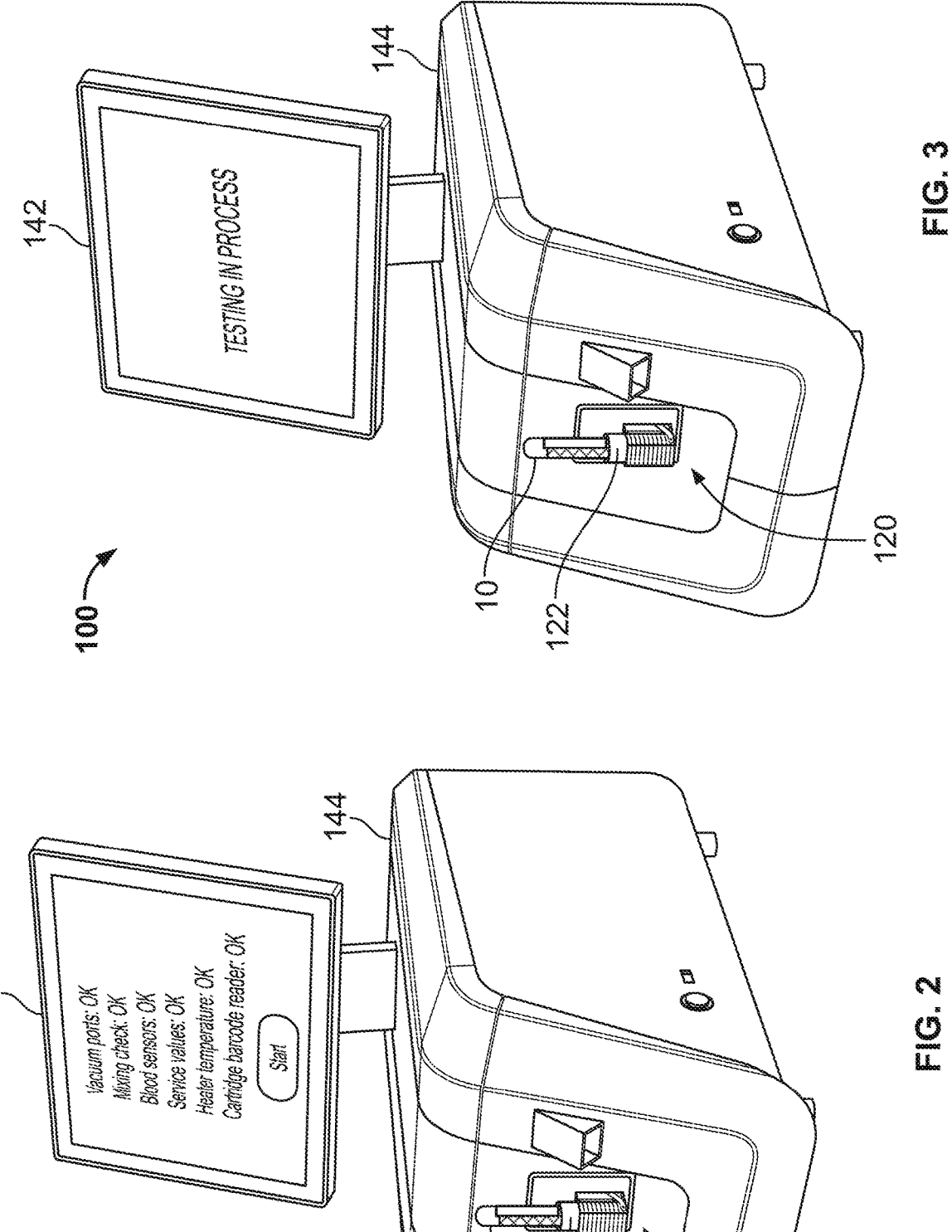

In some embodiments, the main body 124 includes a barcode location 125. The barcode location 125 can be used as a location at which to adhere a barcode label, or to print a barcode. The barcode location 125 is on the leading end of the cartridge 120 (in relation to the direction of insertion of the cartridge 120 into the analyzer console 140 as shown in FIGS. 1-3).

In the depicted embodiment, the right cover 126 includes blood detection locations 127*a* and 127*b*. As will be described further below, the blood detection locations 127*a* and 127*b* are designated locations on the cartridge 120 at which sensors of the analyzer console 140 interface with the cartridge 120. The sensors inspect for the presence of blood within the cartridge 120 at the blood detection locations 127*a* and 127*b*. In some embodiments, the sensors are optical sensors (e.g., infrared sensors) and the blood detection locations 127*a* and 127*b* are polished areas that have enhanced transparency and optical clarity. As such, the right cover 126 is configured so that the optical sensors of the analyzer console 140 can readily detect the presence or absence of blood at the blood detection locations 127*a* and 127*b*.

Figure 6:
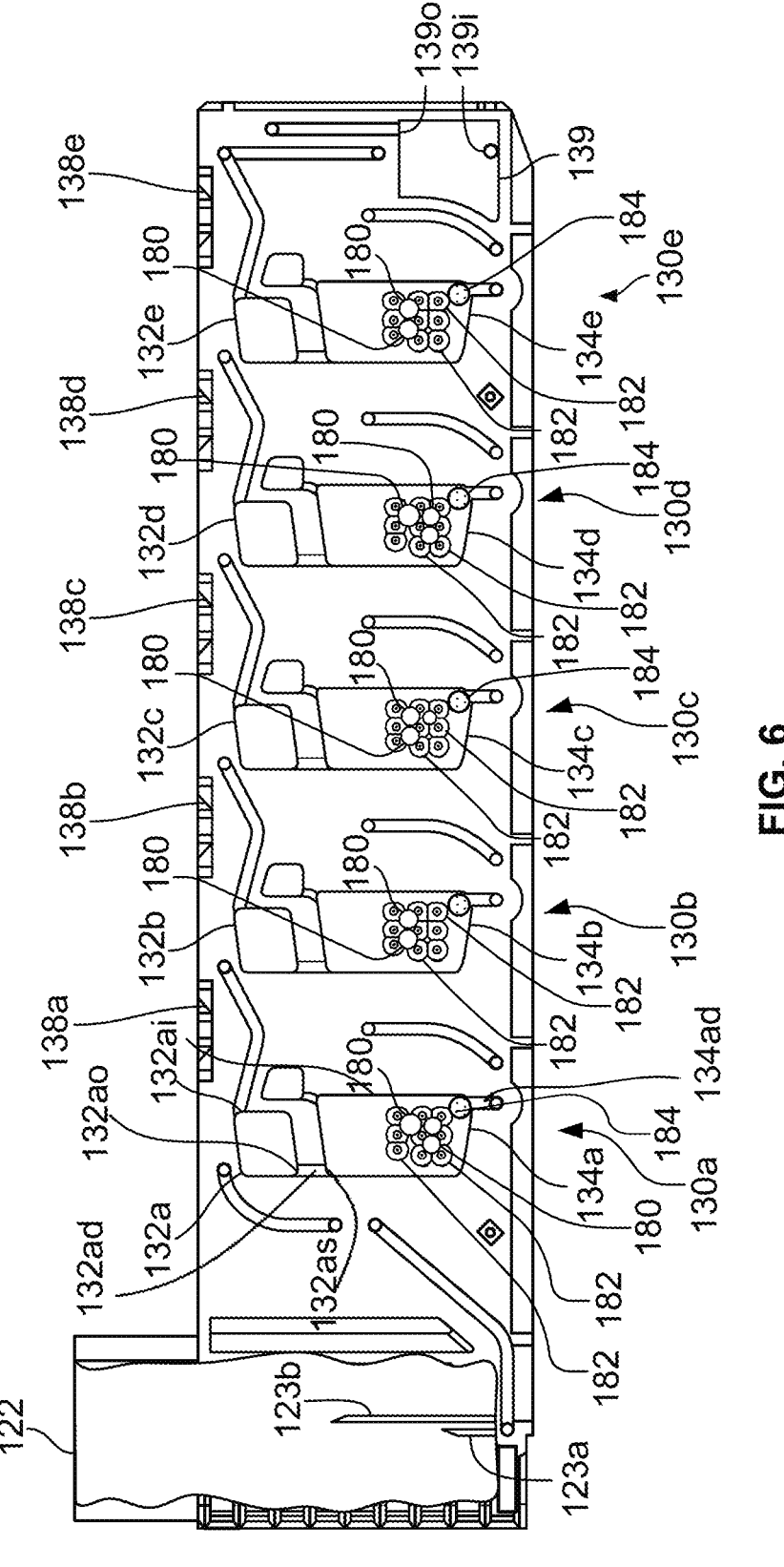
FIG. 6 is a right side partial cutaway view of the cartridge component of FIG. 4.

Referring now to FIGS. 4, 5, and 6, broadly speaking the single-use cartridge 120 is configured to: (i) extract blood from a blood collection tube (e.g., blood collection tube 10 of FIGS. 1-3) and measure a precise volume of the extracted blood, (ii) mix a precise amount of blood with reagents, and (iii) deliver the mixture to multiple cup and pin locations of the cartridge 120 where thromboelastometry testing is performed. These steps will be described in more detail below.

In the depicted embodiment, the single-use cartridge 120 includes five individual blood flow channels 130*a*, 130*b*, 130*c*, 130*d*, and 130*e*. Alternately, in some embodiments the cartridge includes a single individual blood flow channel, or two individual blood flow channels, or three individual blood flow channels, or four individual blood flow channels, or six individual blood flow channels, or more than six individual blood flow channels. Each channel 130*a-e* includes: (i) a measuring chamber, (ii) a mixing chamber containing reagent(s) and a mixing element, and (iii) a blood coagulation testing chamber (e.g., in this embodiment a cup having a movable probe/pin therein). For example, the channel 130*a* includes a measuring chamber 132*a*, a mixing chamber 134*a*, and a testing chamber 136*a* (refer to the example of the testing chamber being depicted in detail in FIGS. 10A-B). Similarly, the channel 130*b* includes a measuring chamber 132*b*, a mixing chamber 134*b*, and a testing chamber 136*b*; the channel 130*c* includes a measuring chamber 132*c*, a mixing chamber 134*c*, and a testing chamber 136*a*; the channel 130*d* includes a measuring chamber 132*d*, a mixing chamber 134*d*, and a testing chamber 136*d*; and the channel 130*e* includes a measuring chamber 132*e*, a mixing chamber 134*e*, and a testing chamber 136*e*.

In some embodiments, the sample well 122 includes needles 123*a* and 123*b* that are configured to pierce a septum of a blood collection tube when the blood collection tube is inserted into the sample well 122. The needle 123*a* is in fluid communication with the channels 130*a-e*, while the needle 123*b* is a vent that facilitates the ready flow of blood out of the blood collection tube.

In the depicted embodiment, the fluid flow paths from the needle 123*a* to the channels 130*a-e* are as follows. The needle 123*a* is confluent with the measuring chamber 132*a*. The measuring chamber 132*a* is confluent with the measuring chamber 132*b*. The measuring chamber 132*b* is confluent with the measuring chamber 132*c*. The measuring chamber 132*c* is confluent with the measuring chamber 132*d*. The measuring chamber 132*d* is confluent with the measuring chamber 132*e*. Accordingly, blood can flow out of the blood collection tube through the needle 123*a* to the measuring chamber 132*a*; from the measuring chamber 132*a* to the measuring chamber 132*b*; from the measuring chamber 132*b* to the measuring chamber 132*c*; from the measuring chamber 132*c* to the measuring chamber 132*d*; and from the measuring chamber 132*d* to the measuring chamber 132*e*. The measuring chambers 132*a-e* may also be referred to as metering chambers 132*a-e*. Each measuring chamber 132*a-e* has an inlet port and an outlet port. The inlet ports are located near the top of the measuring chambers 132*a-e*. For example, measuring chamber inlet port 132*ai* is located near the top of the measuring chamber 132*a*. This configuration can be advantageous if the blood contains gaseous bubbles, because such gas may be allowed to escape from the blood as the blood enters the measuring chambers 132*a-e*. In addition, this configuration may advantageously minimize fluid flow turbulence as the blood flows into the measuring chambers 132*a-e*, thereby reducing the likelihood of damaging the blood cells.

The outlet ports 134*ao-eo* for transferring blood from the measuring chambers 132*a-e* to the mixing chambers 134*a-e* are located at the bottom of the measuring chambers. For example, measuring chamber outlet port 132*ao* is located at the bottom of the measuring chamber 132*a*. In some embodiments, the bottom of the measuring chamber 132*a* is angled downward towards the outlet port 132*ao*. In some embodiments, the bottom of the measuring chamber 132*a* is at an angle of 2°-15° from a plane parallel to the bottom or top of the cartridge 120. In some embodiments, the bottom of the measuring chamber 132a is at an angle of 2°-15° from a plane orthogonal to the direction of force applied to move the blood sample through the outlet port 132ao. In one embodiment, the angles described above are approximately 2°, 3°, 4°, 5°, 6°, 7°, 8°, 9°, 10°, 11°, 12°, 13°, 14°, or 15°. In a preferred embodiment, the angles described above are 5°, although other angles will also be effective. This configuration can help facilitate the complete filling of the measuring chambers 132a-e with blood. It can also minimize transfer of bubbles into the outlet port 132ao as more blood is transferred to the outlet port 132ao before the surface of the volume of blood (which may contain bubbles) contained in the measuring chamber 132a contacts the outlet port 132ao. As such, a precise volume of blood is contained within the measuring chambers 132a-e.

In some embodiments, the top of the measuring chamber 132a is angled to cause air to escape the measuring chamber 132a from a transfer port located at the top of the measuring chamber opposite to the inlet port 132ai. The transfer port is used to transfer air and fluid out of the measuring chamber 132a and into another measuring chamber (e.g., 132b) or into an overflow chamber 139. In this embodiment, the top of the measuring chamber 132a is angled upward from a low point above an inlet port 132ai to a higher point above the transfer port. The angle of the top of the measuring chamber is between 2°-15° when compared to the a plane parallel to the bottom or top of the device, or as compared to a plane orthogonal to the major field of gravitational force applied to the blood sample while in the measuring chamber 132a. In one embodiment, the angle described above is approximately 2°, 3°, 4°, 5°, 6°, 7°, 8°, 9°, 10°, 11°, 12°, 13°, 14°, or 15°. In a preferred embodiment, the angle described above is 5°, although other angles will also be effective. In a device comprising the angled top of the measuring chamber 132a, air and bubbles are transferred out of the measuring chamber 132a before blood, providing a measured blood sample with decreased amount of air that may impact the accuracy of the measurement of the blood, as well as interfere with other downstream applications. In some embodiments, both the top and bottom of the measuring chamber 132a are angled as described above.

From the foregoing description of the fluid flow paths from the needle 123a to the measuring chambers 132a-e, and from the foregoing description of the location of the measuring chamber outlet ports, it should be understood that the measuring chambers 132a-e will be filled with blood in a sequential manner. That is, first measuring chamber 132a will be filled with blood; then blood from measuring chamber 132a will flow to measuring chamber 132b; then measuring chamber 132b will be filled with blood; then blood from measuring chamber 132b will flow to measuring chamber 132c; then measuring chamber 132c will be filled with blood; then blood from measuring chamber 132c will flow to measuring chamber 132d; then measuring chamber 132d will be filled with blood; then blood from measuring chamber 132d will flow to measuring chamber 132e; then measuring chamber 132e will be filled with blood.

After the measuring chamber 132e is filled with blood, then blood from measuring chamber 132e will flow to an overflow chamber 139. The blood flowing from measuring chamber 132e will enter the overflow chamber 139 at an overflow chamber inlet port 139i. As will be described further below, the overflow chamber 139 serves to ensure that the measuring chamber 132e becomes completely full, while preventing blood from exiting the cartridge 120 and flowing into a vacuum source that is used to draw the blood into the measuring chambers 132a-e as described above. The vacuum source is fluidly connected to the overflow chamber 139 at an overflow chamber outlet port 139o. When a negative pressure (with respect to ambient pressure) from the vacuum source is applied at the overflow chamber outlet port 139o, blood from a blood collection tube that is coupled with needle 123a will flow into the cartridge 120 to fill all the measuring chambers 132a-e. Some blood will also exit the measuring chamber 132e and flow towards the overflow chamber 139.

As described further below, various valves and vents are interspersed within the fluid flow paths so that the blood flow can be controlled by the analyzer console according to predefined schemes. In addition, the aforementioned blood detection locations 127a and 127b (refer to FIG. 5) are designated locations on the cartridge 120 at which sensors of the analyzer console 140 interface with the cartridge 120. The sensors inspect for the presence of blood within the cartridge 120 at the blood detection locations 127a and 127b. The blood sensor location 127a is on the fluid flow path between the needle 123a and the measuring chamber 132a. When the analyzer console detects blood at blood sensor location 127a, the analyzer console 140 determines that blood has been drawn into the cartridge 120. The blood sensor location 127b is on the fluid flow path between the measuring chamber 132e and the overflow chamber 139. When the analyzer console detects blood at blood sensor location 127b, the analyzer console 140 determines that blood has been drawn into and filled all the measuring chambers 132a-e. Further, when the analyzer console 140 detects blood at blood sensor location 127b, the analyzer console 140 may cease further application of negative pressure at the overflow chamber outlet port 139o. In other words, by detecting blood at blood sensor location 127b, the analyzer console 140 can determine that the application of vacuum has successfully filled all the measuring chambers 132a-e and that the application of vacuum can be ceased. Optionally, the cartridge 120 may be equipped with a blood temperature sensor at or near the location of blood sensor location 127b so as to verify the blood sample is at a predetermined target temperature.

As described above, each individual channel 130a-e has a measuring chamber 132a-e respectively. In some embodiments, the fluid flow paths within the individual channels 130a-e are as follows. From the measuring chambers 132a-e, the blood can flow to the respective mixing chambers 134a-e. For example, the blood from measuring chamber 132a can flow to the mixing chamber 134a. Similarly, the blood from measuring chamber 132b can flow to the mixing chamber 134b; the blood from measuring chamber 132c can flow to the mixing chamber 134c; the blood from measuring chamber 132d can flow to the mixing chamber 134d; and the blood from measuring chamber 132e can flow to the mixing chamber 134e. From the mixing chambers 132a-e (after completion of the mixing), the blood can flow to the respective testing chambers 136a-e (having a corresponding probe/pin 138a-e therein, refer below to FIG. 10A-b). For example, the blood from mixing chamber 134a can flow to the testing chamber 136a. Similarly, the blood from mixing chamber 134b can flow to the testing chamber 136b; the blood from mixing chamber 134c can flow to the testing chamber 136c; the blood from mixing chamber 134d can flow to the testing chamber 136d; and the blood from mixing chamber 134e can flow to the testing chamber 136e. Various valves and vents that are controllable by the analyzer console 140 are interspersed within the fluid flow paths of the individual channels 130a-e. Using such valves and vents, the blood flow within the individual channels 130*a-e* can be controlled by the analyzer console 140 in accordance with predefined schemes.

Referring now to FIGS. 6 and 7, additional features of the cartridge 120 will now be described. In FIG. 6, a side view of particular chambers of the cartridge 120 (measuring chambers 132*a-e*, reagent mixing chambers 134*a-e*, and blood coagulation testing chambers 136*a-e*) is provided. In FIG. 7, a left side view of cartridge 120 and individual channels 130*a-e* is provided. In this view there is visibility of testing chamber inlet ports 136*ai*, 136*bi*, 136*ci*, 136*di*, and 136*ei* for testing chambers 136*a-e* respectively. The inlet ports 136*ai-ei* are located near the top of the testing chambers 136*a-e*, for example, along a side wall of the chamber 136*a-e* and at a height above the distal head of the pin 138*a-e* that interacts with the blood sample but below the proximal end of the pin 138*a-e* (refer to FIG. 10B). This configuration can be advantageous if the blood contains gaseous bubbles, because such gas may be allowed to escape from the blood as the blood enters the cups 136*a-e*. In viscous solutions, bubbles may be retained at the bottom of the cup 136*a-e* if the solution enters through the bottom, adversely impacting thromboelastometric measurements by the pin 138*a-e* in the cup 136*a-e*. In addition, this configuration may advantageously minimize fluid flow turbulence as the blood flows into the testing chambers 136*a-e*. Fluid flow turbulence and bubble mixing is also minimized by having a small diameter or blood flow area of the sample inlet port 136*bi* into the cup 136*a-e*. Bubbles present in blood from the mixing chamber 134*a-e* separate from the fluid and remain at the top surface of the blood in the cup 136*a-e* by using a smaller diameter of a sample inlet port 136*bi* in combination with the location of the inlet port 136*bi* along the side wall of the chamber 136*a-e*. In some embodiments, the diameter of the sample inlet port 136*bi* is 1 mm. In some embodiments, the diameter of the sample inlet port 136*bi* is approximately 0.5, 0.6, 0.7, 0.8, 0.9, 1.0, 1.1, 1.2, 1.3, 1.4, or 1.5 mm.

In the depicted embodiment, the cartridge 120 includes two locator pin receptacles 140*a* and 140*b*. The locator pin receptacles 140*a* and 140*b* are used to mate with locator pins of the analyzer console 140 (as described further below). In this manner, the cartridge 120 can be accurately positioned in relation to the analyzer console 140.

The cartridge 120 also includes a vacuum application port 162. When a source of vacuum is applied at the vacuum application port 162, and when the vents and valves of the cartridge 120 are in the proper configuration, blood can be drawn into the measuring chambers 132*a-e* as described above, and as described further below.

The cartridge 120 also includes a pressure application port 164. When a source of pressure is applied at the pressure application port 164, and when the vents and valves of the cartridge 120 are in the proper configuration, blood can be forced to flow from the measuring chambers 132*a-e* into the mixing chambers 134*a-e*, and subsequently from the mixing chambers 134*a-e* into the testing chambers 136*a-e* as described above, and as described further below.

In the depicted embodiment, the cartridge 120 also includes vents 166*a*, 166*b*, 166*c*, 166*d*, and 166*e*. Other cartridge embodiments may include fewer or more vents. The vents 166*a-e* are confluent with the mixing chambers 134*a-e* respectively. Accordingly, when the vents 166*a-e* are open to allow airflow therethrough, air from the mixing chambers 134*a-e* can be readily displaced from the mixing chambers 134*a-e* as blood flows into the mixing chambers 134*a-e*. Conversely, when the vents 166*a-e* are closed to prevent airflow therethrough, blood is inhibited from flowing into the mixing chambers 134*a-e* because the air within the mixing chambers 134*a-e* is not allowed to be displaced therefrom. The vents 166*a-e* can be individually opened and closed by the analyzer console 140 in accordance with predefined schemes as described further below. Accordingly, blood flow into the mixing chambers 134*a-e* can be controlled as desired.

In the depicted embodiment, the cartridge 120 also includes valves 168, 170, 160*a*, 160*b*, 160*c*, 160*d*, and 160*e*. Other cartridge embodiments may include fewer or more valves. The valves 168, 170, and 160*a-e* are located within fluid flow paths of the cartridge 120. Accordingly, the valves 168, 170, and 160*a-e* can be actuated (opened or closed) by the analyzer console 140 to allow or to prevent fluid flow through the fluid flow paths in which the valves 168, 170, and 160*a-e* are respectively located. For example, the valve 168 is located in the fluid flow path between the needle 123*a* and the measuring chamber 132*a*. Accordingly, when the valve 168 is open blood can flow from the needle 123*a* to the measuring chamber 132*a*, and when the valve 168 is closed blood cannot flow from the needle 123*a* to the measuring chamber 132*a*.

The valve 170 is located in the fluid flow path between the measuring chamber 132*e* and the overflow chamber 139. Accordingly, when the valve 170 is open blood can flow from the measuring chamber 132*e* to the overflow chamber 139, and when the valve 170 is closed blood cannot flow from the measuring chamber 132*e* to the overflow chamber 139.

The valves 160*a-e* are located in the fluid flow paths between the mixing chambers 134*a-e* and the testing chambers 136*a-e* respectively. Accordingly, when the valves 160*a-e* are open blood can flow from the mixing chambers 134*a-e* to the testing chambers 136*a-e* respectively, and when the valves 160*a-e* are closed blood cannot flow from the mixing chambers 134*a-e* to the testing chambers 136*a-e*.

As will be described further below, in some embodiments the valves 160*a-e* can be individually actuated by pins that are translated towards and away from the valves 160*a-e*. To close the valves 160*a-e*, the pins can engage with and distend elastomer members of the valves 160*a-e* so that the elastomer member makes contact with a valve seat of the valves 160*a-e*. When such pins are retracted away from the elastomer members of the valves 160*a-e*, the elastomer members will rebound such that the elastomer member is no longer distended and then the valve is opened. The pins can be translated by solenoids in some embodiments.

Other mechanisms to regulate fluid flow in the cartridge 120 may also be present. For example, stop junctions may be placed between the measuring chamber 132*a-e* and the mixing chamber 134*a-e* to control the flow of blood from the measuring chamber 132*a-e* to the mixing chamber 134*a-e*. In some embodiments, the stop junctions are a barrier that can be opened upon application of a sufficient amount of pressure to the barrier. In some embodiments, the stop junction comprises a narrow area for flow of the sample fluid such that surface tension of the sample fluid prevents flow through the stop junction unless sufficient pressure is applied. Once sufficient pressure is applied, the flow of sample fluid through the stop junction may continue due to capillary forces.

Referring to FIG. 6 in more detail, some embodiments of the mixing chambers 134*a-e* contain: (i) one or more dissolvable reagent beads 180, (ii) multiple retaining elements 182, and (iii) a mixing element 184. The one or more reagent beads 180 are disposed within and retained within the confines of the multiple retaining elements 182. The mixing elements 184 are disposed in the bottom portions of the mixing chambers 134*a-e*, and are free to move horizontally across the bottom portions of the mixing chambers 134*a-e*. The multiple retaining elements 182 separate the reagent beads 180 from the mixing element 184, and prevent the mixing element 184 from migrating upward away from the bottom portions of the mixing chambers 134*a-e*. Thus, the multiple retaining elements 182 prevent direct contact of the mixing element 184 with reagent beads 180 in the mixing chambers 134*a-e*. Preferably, the retaining elements 182 extend into each mixing chamber 134*a-e* so as to maintain a predetermined vertical position of each of the reagent beads 180 within the mixing chamber (e.g., a vertical position below the height of the blood portion passed into the mixing chamber 134*a-e*), thereby ensuring that each of the beads 180 will be submerged when the predetermined amount of blood is directed into the respective mixing chamber 134*a-e*. In an embodiment, the height of the liquid that fills the mixing chamber 134*a-e* from the measuring chamber 132*a-e* (i.e., the fill level) is above the retaining elements 182 in the mixing chamber. In some embodiments, the retaining elements 182 are above the height of the fill level of the mixing chamber. In these embodiments, the retaining elements are configured to position the reagent in the path of the fluid such that the reagent is dissolved by the liquid upon entry of the liquid into the mixing chamber. In some embodiments, the flow path is defined as the path the liquid travels to go from one chamber to another, including within the chamber itself after entering from an inlet or duct.

Also, in some embodiments, the multiple retaining elements 182 in each mixing chamber 134*a-e* maintain each of the reagent beads 180 in the respective mixing chamber 134*a-e* separate from one another. In such embodiments, each of the reagent beads 180 is not contacted by other beads 180 in the respective mixing chamber 134*a-e*, is not contacted by the mixing element 184 in the respective mixing chamber 134*a-e*, and is maintained at a vertical height within the respective mixing chamber 134*a-e* below the height of the blood portion transported into the respective mixing chamber 134*a-e*.

The retaining elements 182 may take the form of several unique configurations that result in control over the location of the reagent beads 180. In some embodiments, the retaining elements 182 also prevent contact between different reagent beads 180, contact of reagent beads 180 with the mixing element 184, and/or contact of the reagent beads 180 with other surfaces or components in the mixing chamber 134*a-e*. In some embodiments, the retaining element 182 is configured to limit movement of the reagent bead 180 within the mixing chamber 134*a-e* and configured to allow the sample liquid or blood sample to dissolve the reagent bead 180. In some embodiments, the retaining element 182 comprises a barrier. The retaining element 182 can also comprise an inward protrusion or an outward protrusion in the wall of the mixing chamber 134*a-e* or on the surface of a right cover 126 or left cover 128, or on other surfaces of the device. In some embodiments, the retaining element 182 comprises a channel, a post, or a divot. The retaining element 182 may comprise an array of posts or an array of divots. In some embodiments, the array of posts comprises posts of different diameters to hold reagent beads of different diameters. In some embodiments, the retaining element 182 comprises a compartment or a series of compartments for holding a reagent bead. The retaining element 182 can also be configured to both limit the movement of a reagent bead in the mixing chamber 134*a-e*, and to allow blood to flow in a way that it contacts and dissolves the reagent bead 180. In some embodiments, the retaining element 182 is configured to allow flow of a blood sample through the mixing chamber 134*a-e*.

The retaining element 182 can further secure the reagent bead 180 below a predetermined blood sample fill level in the mixing chamber 134*a-e*. This fill level is determined by the volume of blood provided by the measuring chamber 132*a-e*, and by the dimensions of the mixing chamber 134*a-e* and volume of components or reagents within the mixing chamber 134*a-e* at the time of filling. This fill level can be predetermined based on the above factors. Therefore, the retaining elements 182 are specifically designed to maintain the position of the reagent beads 180 below this predetermined fill level.

Additionally, the retaining elements 182 can limit the movement of a mixing element 184 within the mixing chamber 134*a-e*. In some embodiments, the resting element 182 used to restrict movement of a mixing element 184 within the mixing chamber 134*a-e* comprise an array of posts or a compartment that allows a sample fluid or blood sample in the mixing chamber 134*a-e* to contact the mixing element 184 such that the sample fluid or blood sample is agitated to facilitate dissolving reagents within the mixing chamber 134*a-e*.

In the depicted embodiment, the one or more dissolvable reagent beads 180 are spherical and are of two different sizes (e.g., about 2 mm diameter and about 3 mm diameter). However, the use of other shapes and/or sizes of reagent beads 180 is also envisioned. In some embodiments, the reagent beads 180 are lyophilized materials, but other forms of materials are also envisioned. The reagent beads 180 can comprise materials such as, but not limited to, $CaCl_2$, ellagic acid/phospholipids, tissue factor, heparinase, polybrene, cytochalasin D, tranexamic acid, and the like, and combinations thereof. The reagent beads 180 are dissolvable in blood. For example, in this particular embodiment, each of the five mixing chambers 134*a-e* is configured to mix a predetermined volume of blood (as defined by the respective measurement chamber 132*a-e*) with a different reagent composition (from the one or more reagent beads 180 therein) for purposes of performing five different assays. In this example, the first mixing chamber 134*e* may include multiple reagent beads 180 the provide $CaCl_2$ and ellagic acid/phospholipids for mixing with the predetermined volume of blood (from the corresponding measuring chamber 132*e*) so that the first sample portion can be used in a first type of assay. Also in this example, the second mixing chamber 134*d* may include multiple reagent beads 180 the provide $CaCl_2$, ellagic acid/phospholipids, and heparinase for mixing with the predetermined volume of blood (from the corresponding measuring chamber 132*d*) so that the second sample portion can be used in a second type of assay. Further, in this example, the third mixing chamber 134*c* may include multiple reagent beads 180 the provide $CaCl_2$, tissue factor, and polybrene for mixing with the predetermined volume of blood (from the corresponding measuring chamber 132*c*) so that the third sample portion can be used in a third type of assay. Also in this example, the fourth mixing chamber 134*b* may include multiple reagent beads 180 the provide $CaCl_2$, tissue factor, polybrene, and cytochalasin D for mixing with the predetermined volume of blood (from the corresponding measuring chamber 132*b*) so that the fourth sample portion can be used in a fourth type of assay. Lastly, in this example, the fifth mixing chamber 134*a* may include multiple reagent beads 180 the provide $CaCl_2$, tissue factor, polybrene, and tranexamic acid for mixing with the predetermined volume of blood (from the corresponding measuring chamber 132a) so that the fifth sample portion can be used in a fifth type of assay.

In some embodiments, the reagent bead 180 carrying the $CaCl_2$ reagent is separated from the rest of the beads 180 in the respective mixing chamber 134a-e so as to first allow mixing and then activation/clotting of the a citrated blood sample. Such separation of the reagent bead 180 carrying the $CaCl_2$ reagent may be achieved using the retaining elements 182 (as described above). Alternatively, such separation can be achieved by retaining the reagent bead 180 carrying the $CaCl_2$ reagent in a separate channel or separate mixing chamber that is separated from other beads 180 in the respective chamber 134a-e (such that the blood portion reaches the $CaCl_2$ reagent after the blood portion mixes with other beads 180 within the respective mixing chamber 134a-e). Alternatively, such separation can be achieved by positioning a $CaCl_2$ reagent liquid or a dried-film $CaCl_2$ reagent in a separate channel so that the blood portion reaches the $CaCl_2$ reagent after the blood portion mixes with other beads 180 in the respective mixing chamber 134a-e. Alternatively, the reagent bead 180 carrying the $CaCl_2$ reagent can be coated with an extra layer (and then retained by the retained by the retaining elements 182 as described above) so that the blood portion begins to dissolve the reagent bead 180 carrying the $CaCl_2$ reagent after the blood portion previously mixes with other beads 180 within the respective mixing chamber 134a-e.

Other configurations for providing a reagent to the blood sample may also be used. In some embodiments, a reagent is coated on the wall of a mixing chamber 134a-e. In some embodiments, a reagent is coated on the right cover 126 or the left cover 128. The coated reagent on the right cover 126 or the left cover 128 can be coated in a way that it will at least partially or entirely be contained within the mixing chamber 134a-e. In some embodiments, the reagent is coated so that it remains under the fill level of the mixing chamber 134a-e (the fill level pertaining to the height of blood in the mixing chamber as determined in part by the predetermined volume of blood as measured in the measuring chamber). In some embodiments, the coated reagent is a film layer, i.e., a reagent film. A reagent film is a layer of reagent coated on or near a surface. The reagent film may be liquid or may be dried. A liquid reagent may be retained as a film layer by a dissolvable layer of material placed over the liquid reagent. A liquid reagent layer may also be applied and then dried on the surface. A pre-dried or solid film reagent may also be applied to a surface to form a film layer. In some embodiments, the film layer is in the form of a dissolvable film strip. In some embodiments, certain reagents are preferred to be delivered in a reagent film as opposed to a reagent bead 180. For example, certain reagents that are difficult to lyophilize in a reagent bead 180 may instead be applied on or near a surface in the device as a film layer.

In some embodiments, the coated reagent is in the form of reagent beads 180. Reagent beads may be secured to the wall of a chamber or to a cover using retaining elements 182. The retaining elements 182 may comprise a series of compartments, posts, divots, inward or outward protrusions, or an array of any of the above. Other shapes or configurations of reagent that can be coated or secured to the cover, a wall of a chamber, or within a fluidic passage between chambers, are also envisioned. In some embodiments, both reagent beads 180 and reagent film are coated on one or more surfaces of the device, e.g., in the mixing chamber 134a-e.

A reagent film may also be provided to dissolve in a blood sample in the mixing chamber 134a-e. The reagent film is dissolvable in blood. The reagent film is adhered to a surface in the mixing chamber 134a-e. In some embodiments, a reagent film is deposited on the walls of the mixing chamber 134a-e. In some embodiments, a reagent film is deposited on the right cover 126 or the left cover 128 at a region that at least partially covers or forms a wall of the mixing chamber 134a-e. The reagent film may be used alone, or in addition to one or more reagent beads 180 placed in the mixing chamber 134a-e. Thus, the use of one or more reagent films in a mixing chamber 134a-e provides additional mechanisms of introducing a reagent into a mixing chamber 134a-e to dissolve in the blood.

In some embodiments, the reagent film comprises a lyophilized material, but other forms of materials are also envisioned. The reagent film can comprise materials such as, but not limited to $CaCl_2$, ellagic acid/phospholipids, tissue factor, heparinase, polybrene, cytochalasin D, tranexamic acid, and the like, and combinations thereof. In one particular example, each of the five mixing chambers 134a-e is configured to mix a predetermined volume of blood (as defined by the respective measurement chamber 132a-e) with a different reagent composition (from one or more reagent beads 180 and/or one or more reagent films therein). In this example, the first mixing chamber 134e may include multiple reagent beads 180 and at least one reagent film to provide $CaCl_2$ and ellagic acid/phospholipids for mixing with the predetermined volume of blood (from the corresponding measuring chamber 132e) so that the first sample portion can be used in a first type of assay. Also in this example, the second mixing chamber 134d may include multiple reagent beads 180 and at least one reagent film to provide $CaCl_2$, ellagic acid/phospholipids, and heparinase for mixing with the predetermined volume of blood (from the corresponding measuring chamber 132d) so that the second sample portion can be used in a second type of assay. Further, in this example, the third mixing chamber 134c may include multiple reagent beads 180 and at least one reagent film to provide $CaCl_2$, tissue factor, and polybrene for mixing with the predetermined volume of blood (from the corresponding measuring chamber 132c) so that the third sample portion can be used in a third type of assay. Also in this example, the fourth mixing chamber 134b may include multiple reagent beads 180 and at least one reagent film to provide $CaCl_2$, tissue factor, polybrene, and cytochalasin D for mixing with the predetermined volume of blood (from the corresponding measuring chamber 132b) so that the fourth sample portion can be used in a fourth type of assay. Lastly, in this example, the fifth mixing chamber 134a may include multiple reagent beads 180 and at least one reagent film to provide $CaCl_2$, tissue factor, polybrene, and tranexamic acid for mixing with the predetermined volume of blood (from the corresponding measuring chamber 132a) so that the fifth sample portion can be used in a fifth type of assay.

Further, a reagent film may be deposited on surfaces upstream or downstream from the mixing chamber to mix with the blood sample before or after the mixing chamber. In some embodiments, a reagent film carrying the $CaCl_2$ reagent is placed in a separate channel or separate mixing chamber that is separated from other reagent beads 180 or reagent film in the respective chamber 134a-e (e.g., such that the blood portion reaches the $CaCl_2$ reagent film after the blood portion mixes with other reagent beads 180 and/or reagent films within the respective mixing chamber 134a-e). Alternatively, a $CaCl_2$ reagent film may be deposited in the mixing chamber 134*a-e* and coated with an extra dissolvable film layer so that the blood portion begins to dissolve the other reagent film carrying the $CaCl_2$ reagent after the blood portion previously mixes with other reagent beads 180 or reagent films within the respective mixing chamber 134*a-3*.

In some embodiments, the reagent bead 180 or reagent film is separated from the rest of the reagent beads 180 or reagent film in the respective mixing chamber 134*a-e* so as to allow mixing with different reagents in a preferred sequence. In one embodiment, such separation of the reagent bead 180 may be achieved using the retaining elements 182 (as described above). Alternatively, such separation can be achieved by retaining the reagent bead 180 or reagent film in a separate channel or separate mixing chamber that is separated from other beads 180 or reagent films in the respective chamber 134*a-e* (such that the blood portion reaches and mixes with the loaded reagents in a preferred sequence). In one embodiment, such separation can be achieved by positioning a reagent liquid, reagent bead 180 or a dried-film reagent in a separate channel so that the blood portion reaches the reagent before or after the blood portion mixes with other reagent beads 180 or reagent films in the respective mixing chamber 134*a-e*. In some embodiments, the reagent bead 180 or reagent film is placed along a duct 134*ad* fluidically connecting the mixing chamber 134*a-e* and the testing chamber 136*a-e*. Alternatively, the reagent bead 180 or reagent film can be coated with an extra layer (and then retained by the retained by the retaining elements 182 as described above) so that the blood portion begins to dissolve the reagent in the reagent bead 180 or reagent film comprising an additional dissolvable layer after the blood portion previously mixes with other reagent beads 180 or reagent films within the respective mixing chamber 134*a-e*. In some embodiments, the coated reagent layer is a dissolvable film layer manufactured from a substrate including a polymeric composition and a reagent. The polymeric composition forms a dissolvable barrier to maintain the coating of the reagent on or near a surface in the device. Upon contact with a blood sample, the polymeric composition dissolves to allow the blood sample to mix with the reagent.

The mixing element 184, comprises a ferromagnetic material including, but not limited to, nickel, cobalt, chromium (IV) oxide, gadolinium, permalloy, and alnico (an aluminum-nickel-cobalt alloy) and the like, and combinations thereof. In the depicted embodiment, the mixing element 184 is spherical and is solid. In other embodiments, the mixing element 184 may have a shape such as, but not limited to, cubical, conical, cylindrical, fan-shaped, elongated, prismatic, and the like, as well as irregular shapes. In some embodiments, the mixing element 184 may include one or more surface features such as protrusions, indentations, or holes, and the like.

As will be described further below, the mixing elements 184 are movable within the mixing chambers 134*a-e* in response to movement of magnets with which the mixing elements 184 magnetically couple. The magnets that the mixing elements 184 magnetically couple with are contained within the analyzer console 140. The movement of the mixing elements 184 encourages the reagent beads 180 to dissolve in the blood contained within the mixing chambers 134*a-e*.

Referring now to FIGS. 8A-8H schematically depict an example fluidic control process 200 that can be used with the thromboelastometry systems provided herein. The process 200 begins with blood contained only within the blood collection tube 10, and ends with blood/reagent mixtures contained in cups 136*a-e* that are configured for rotary thromboelastometry. It should be understood that, in some embodiments, the cartridge 120 (refer to FIGS. 1-7) that is used to implement the fluidic control process 200 is heated (e.g., to about 37° C.) prior to having any blood therein.

Figure 8A:
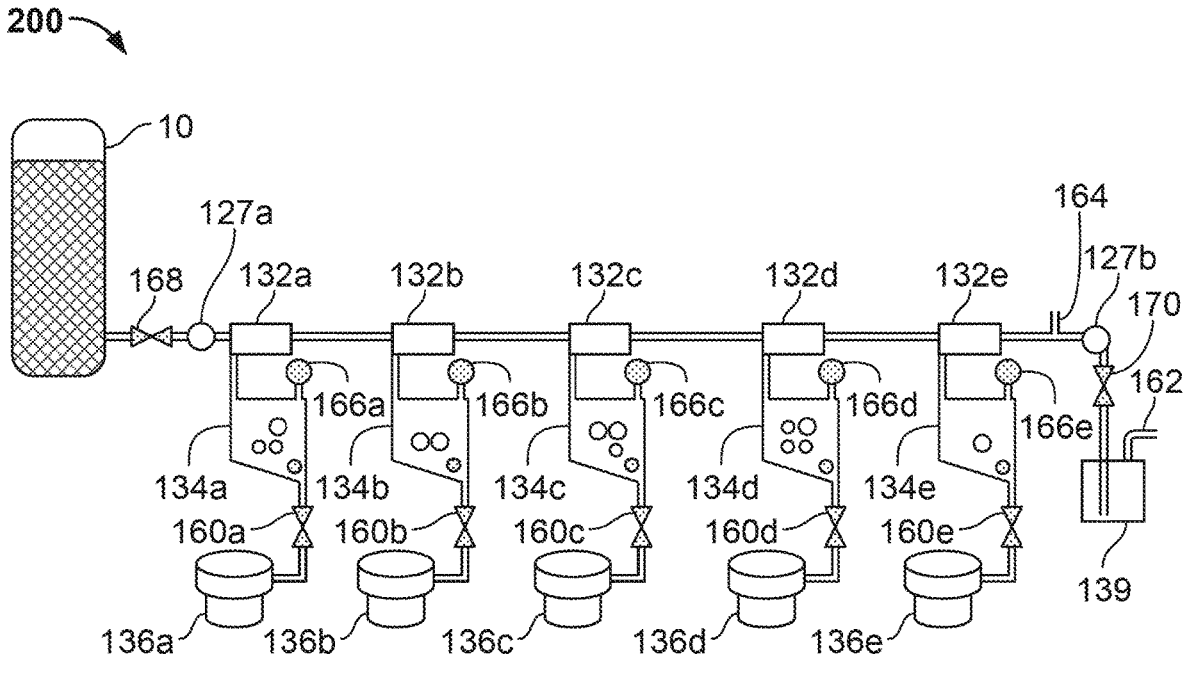
FIG. 8A-8H are a series of schematic diagrams depicting operations of the thromboelastometry system of FIGS. 1A, 1B, 2, and 3, in accordance with some embodiments.

Referring to FIG. 8A, the example fluidic control process 200 includes the blood collection tube 10, the measuring chambers 132*a-e*, the mixing chambers 134*a-e*, and cups 136*a-e*, the overflow chamber 139, the blood detection locations 127*a* and 127*b*, the vacuum application port 162, the pressure application port 164, the vents 166*a-e*, the valves 168, 170, and 160*a-e*. In the depicted configuration, valve 168 is closed, thereby retaining the blood substantially within the blood collection tube 10.

Figure 8B:
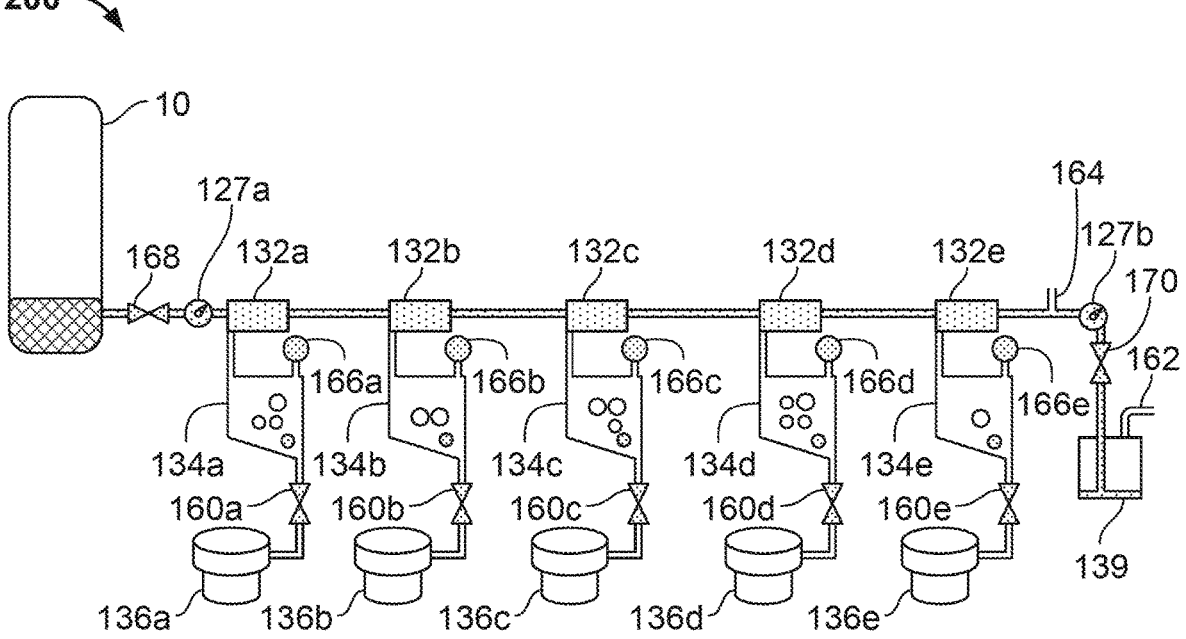

While the example fluidic control process 200 includes five blood flow channels (each comprising a measuring chamber 132*a-e*, a mixing chamber 134*a-e*, and a cup 136*a-e* respectively), it should be understood that having five blood flow channels is not required in all embodiments. For example, in some embodiments only a single blood flow channel is included. Alternately, two blood flow channels are included, or three blood flow channels are included, or four blood flow channels are included, or six blood flow channels are included, or more than six blood flow channels are included. Referring to FIG. 8B, the measuring chambers 132*a-e* are filled with blood, and a small amount of blood is contained within the overflow chamber 139. To arrive at this state, the following changes were made (in comparison to FIG. 8A) and/or the following conditions existed: (i) the valves 168 and 170 were opened, (ii) the valves 160*a-e* were closed, (iii) the vents 166*a-e* were closed, (iv) a negative pressure was applied to the vacuum application port 162, and (v) the pressure application port 164 was unpressurized. Accordingly, the blood flowed: (i) out of the blood collection tube 10, (ii) through the valve 168, (iii) through the blood detection location 127*a*, (iv) into and filling the measuring chamber 132*a*, (v) into and filling the measuring chamber 132*b*, (vi) into and filling the measuring chamber 132*c*, (vii) into and filling the measuring chamber 132*d*, (viii) into and filling the measuring chamber 132*e*, (ix) through blood detection location 127*b*, (x) through valve 170, and (xi) into the overflow chamber 139. When blood was detected in the blood detection location 127*b*, the application of the negative pressure was discontinued—thereby stopping further blood flow.

In some embodiments, the example fluidic control process 200 includes a stop junction 132*as* between one, some, or each of the measuring chambers 132*a-e* and the mixing chambers 134*a-e*. In some embodiments, blood flows through the stop junction 132*as* in the duct 132*ad* connecting the measuring chambers 132*a-e* and the mixing chambers 134*a-e* through application of a positive pressure to the measuring chamber or a negative pressure to the mixing chamber 134*a-e*. Stop junctions provide a mechanism to regulate flow without a connection to an external control device. The application of positive or negative pressure may create a pressure differential on either side of the stop junction, causing the stop junction to open, or drawing blood through the stop junction by overcoming forces due to surface tension. The desired pressure may be applied to cause blood to flow through the stop junction via pressure application port 164 and/or through opening an air pressure vent 166*a-e* to release pressure in the corresponding mixing chamber 134*a-e*.

In some embodiments, the example fluidic control process 200 includes a stop valve in lieu of or in addition to a stop junction between one, some, or each of the measuring chambers 132*a-e* and the mixing chambers 134*a-e*. In some embodiments, the stop valve is a snap acting valve, snapping open upon reaching a set pressure, or a modulating valve that opens in proportion to the pressure differential. Other cartridge embodiments may include pressure-controlled valves in other fluid paths.

In some embodiments, the stop valve may be opened and closed by the same mechanism provided by the valves shown in the reaction system 168, 162, 160*a-e* at FIGS. 8A-8H. In some embodiments, the stop valves may be opened and closed through a mechanism other than pressure application to the blood. In some embodiments, the stop valve is opened upon remote command from a control device connected to the stop valve. In some embodiments, the stop valve can be actuated by the analyzer console 140 to allow or to prevent fluid flow through the fluid path from the measuring chamber 132*a-e* to the mixing chamber 134*a-e*.

Figure 8C:
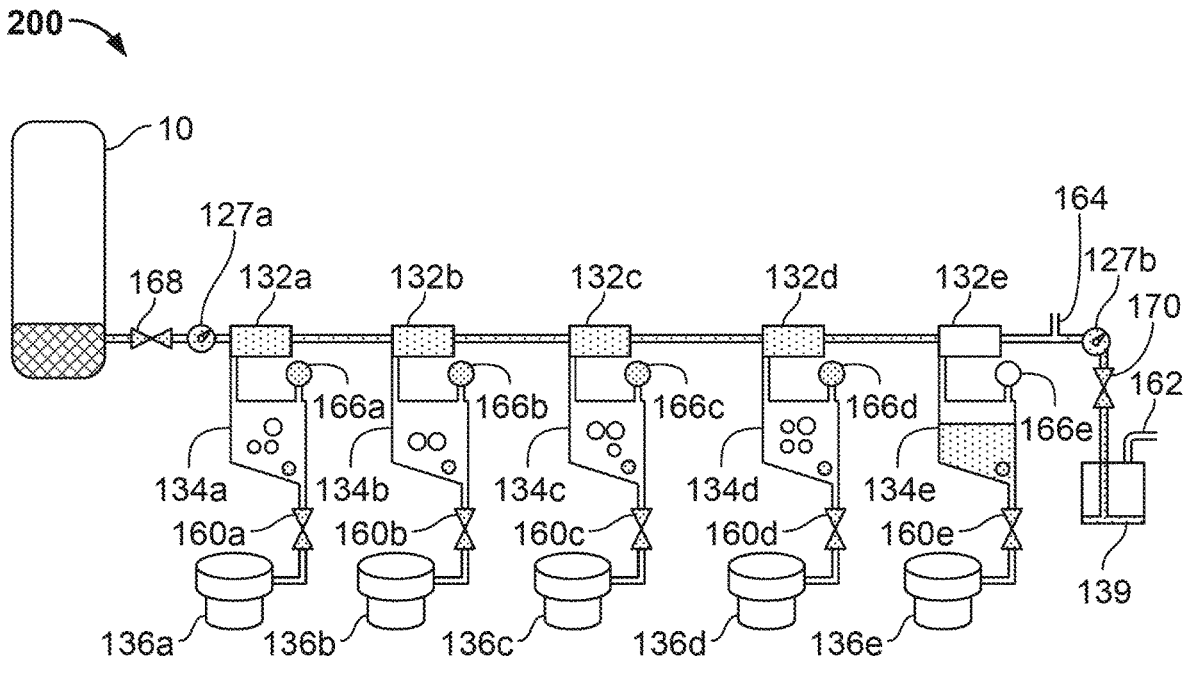

Referring to FIG. 8C, the measuring chambers 132*a-d* are still filled with blood, but the blood from the measuring chamber 132*e* has transferred to the mixing chamber 134*e*. To arrive at this state, the following changes were made (in comparison to FIG. 8B) and/or the following conditions existed: (i) the valves 168 and 170 were closed, (ii) the valves 160*a-e* remained closed, (iii) the vents 166*a-d* remained closed, (iv) the vent 166*e* was opened, and (v) a source of air pressure was applied to the pressure application port 164. Accordingly, the blood flowed: (i) out of the measuring chamber 132*e*, and (ii) into the mixing chamber 134*e*. Because the vents 166*a-d* and the valves 160*a-d* remained closed, the blood in the measuring chambers 132*a-d* did not flow into the mixing chambers 134*a-d*. With blood in the mixing chamber 134*e*, the mixing element in mixing chamber 134*e* can move and agitate the blood to facilitate the dissolving of the reagent beads therein.

In some embodiments, the fluidic control process 200 shown in FIG. 8C includes stop junctions (not shown) between the measuring chamber 132*a-e* and the mixing chamber 134*a-e* to prevent the flow of blood from the measuring chamber to the mixing chamber unless a sufficient pressure differential between the measuring chamber 132*a-e* and the mixing chamber 134*a-e* is applied. In this embodiment, the stop junction prevents leakage of blood from measuring chambers 132*a-d* into mixing chambers 166*a-d* without opening the vents 166*a-d* or applying sufficient pressure to the pressure application port 164 to cause blood to flow through the stop junction. To fill the measuring chamber 132*e* with blood from the mixing chamber 134*e*, the following changes were made (in comparison to FIG. 8B) and/or the following conditions existed: (i) the valves 168 and 170 were closed, (ii) the valves 160*a-e* remain closed, (iii) the vents 166*a-d* remain closed, (iv) the vent 166*e* was opened, and (v) a source of air pressure was applied to the pressure application port 164 to cause blood to flow through the stop junction from the measuring chamber 132*e* into the mixing chamber 134*e*, while the stop junctions between the measuring chambers 132*a-d* and the mixing chambers 134*a-d* prevent flow of blood from the measuring chambers 132*a-d* into the mixing chambers 134*a-d*. With blood in the mixing chamber 134*e*, the mixing element in mixing chamber 134*e* can move and agitate the blood to facilitate the dissolving of the reagent beads therein.

Figure 8D:
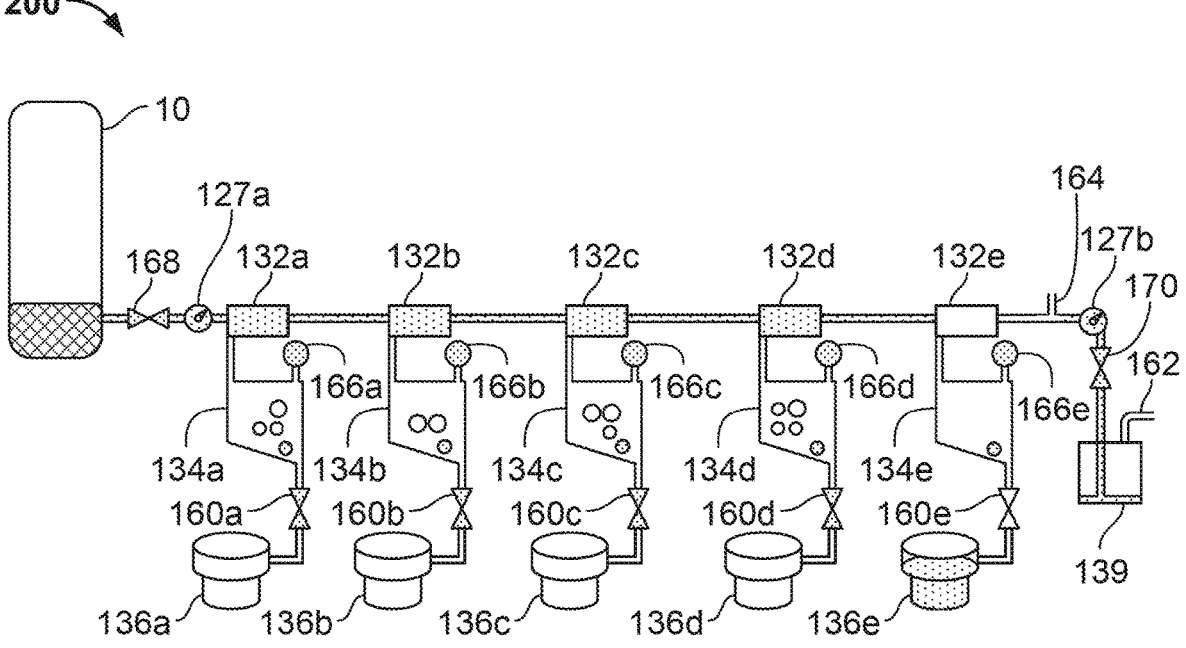

Referring to FIG. 8D, the measuring chambers 132*a-d* are still filled with blood, and the blood/reagent mixture that was in the mixing chamber 134*e* (refer to FIG. 8C) has transferred to the cup 136*e*. To arrive at this state, the following changes were made (in comparison to FIG. 8C) and/or the following conditions existed: (i) the valves 168 and 170 remained closed, (ii) the valve 160*e* was opened, (iii) the valves 160*a-d* remained closed, (iv) the vent 166*e* was closed (v) the vents 166*a-d* remained closed, and (vi) a source of air pressure was applied to the pressure application port 164. Accordingly, the blood/reagent mixture flowed: (i) out of the mixing chamber 134*e*, and (ii) into the cup 136*e*. Because the vents 166*a-d* and the valves 160*a-d* remained closed, the blood did not flow from the measuring chambers 132*a-d* towards the mixing chambers 134*a-d*. With the blood/reagent mixture located in the cup 136*e*, rotary thromboelastometry can begin in the cup 136*e*.

Figure 8E:
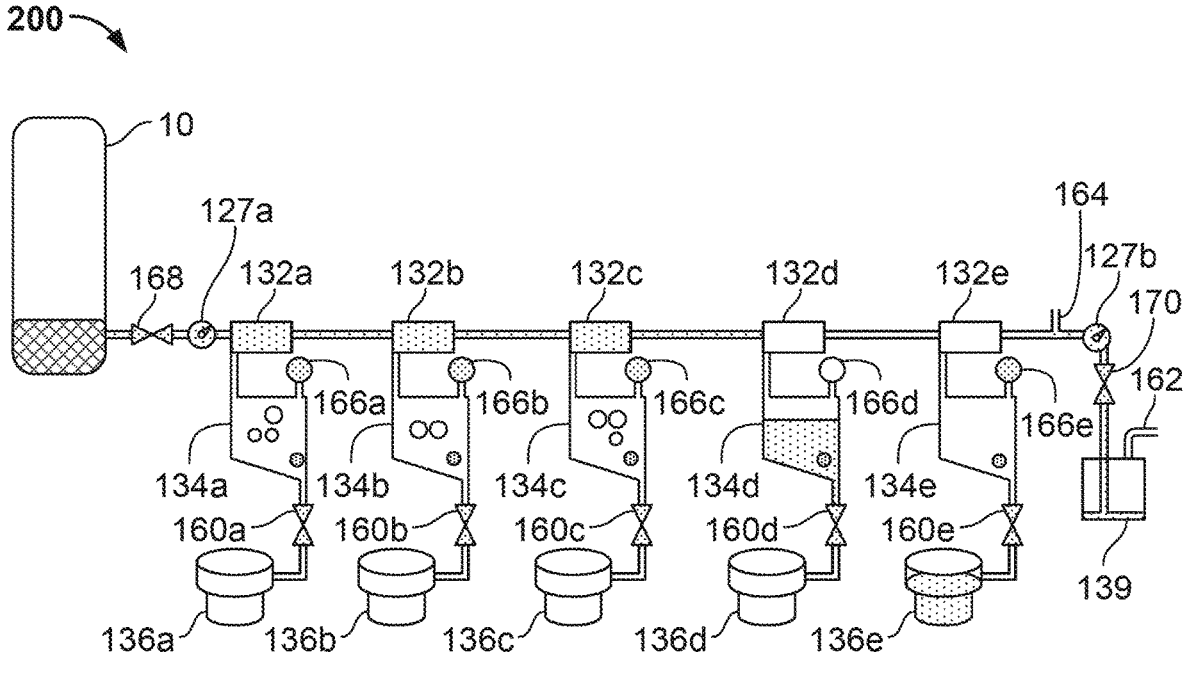

Referring to FIG. 8E, the measuring chambers 132*a-c* are still filled with blood, the cup 136*e* is still filled with blood/reagent mixture, and the blood that was in the measuring chamber 132*d* (refer to FIG. 8D) has transferred to the mixing chamber 134*d*. To arrive at this state, the following changes were made (in comparison to FIG. 8D) and/or the following conditions existed: (i) the valves 168 and 170 remained closed, (ii) the valve 160*e* was closed, (iii) the valves 160*a-d* remained closed, (iv) the vent 166*d* was opened (v) the vents 166*a-c* and 166*e* remained closed, and (vi) a source of air pressure was applied to the pressure application port 164. In embodiments comprising a stop junction between the measuring chamber 132*d* and the mixing chamber 134*d*, the, blood travels through the stop junction by application of pressure differential between the measuring chamber 132*d* and the mixing chamber 134*d*, while the stop junctions between the measuring chambers 132*a-c* and the mixing chambers 134*a-c* prevent flow. Accordingly, the blood flowed: (i) out of the measuring chamber 132*d*, and (ii) into the mixing chamber 134*d*. Because the vents 166*a-c* and because the valves 160*a-c* remained closed, the blood did not flow from the measuring chambers 132*a-c* towards the mixing chambers 134*a-c*. With blood in the mixing chamber 134*d*, the mixing element in mixing chamber 134*d* can agitate the blood to facilitate the dissolving of the reagent beads therein.

Figure 8F:
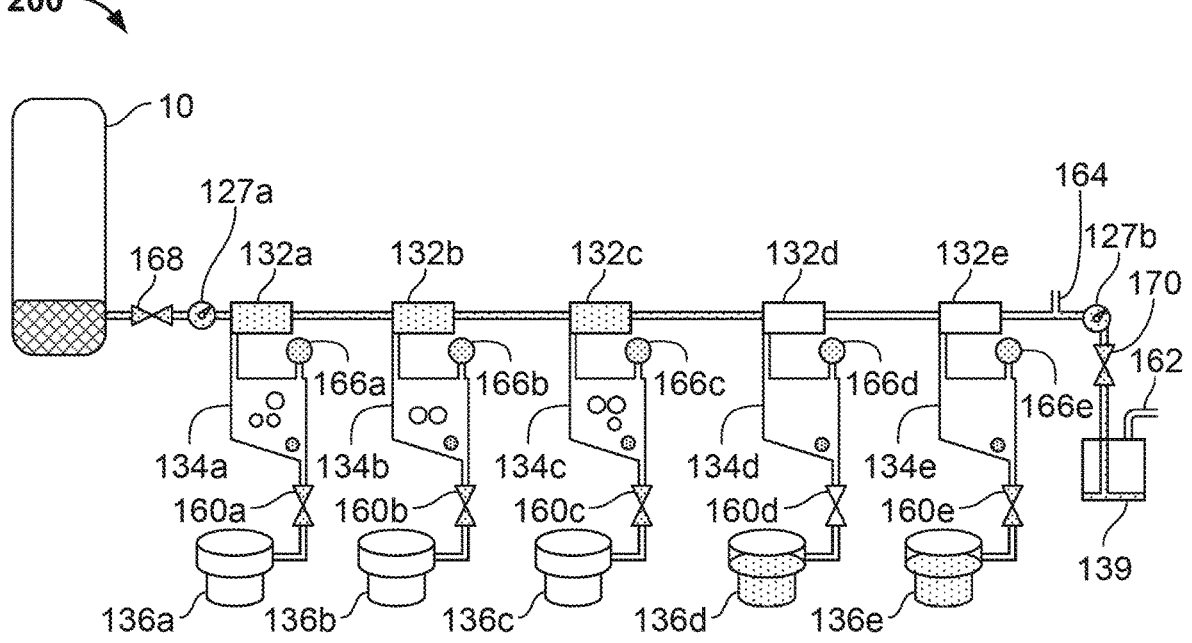

Referring to FIG. 8F, the measuring chambers 132*a-c* are still filled with blood, the cup 136*e* is still filled with blood/reagent mixture, and the blood/reagent mixture that was in the mixing chamber 134*d* (refer to FIG. 8E) has transferred to the cup 136*d*. To arrive at this state, the following changes were made (in comparison to FIG. 8E) and/or the following conditions existed: (i) the valves 168 and 170 remained closed, (ii) the valve 160*d* was opened, (iii) the valves 160*a-c* and 160*e* remained closed, (iv) the vent 166*d* was closed (v) the vents 166*a-c* and 166*e* remained closed, and (vi) a source of air pressure was applied to the pressure application port 164. Accordingly, the blood/reagent mixture flowed: (i) out of the mixing chamber 134*d*, and (ii) into the cup 136*d*. Because the vents 166*a-c* and the valves 160*a-c* remained closed, the blood did not flow from the measuring chambers 132*a-c* towards the mixing chambers 134*a-c*. With the blood/reagent mixture located in the cup 136*d*, rotary thromboelastometry can begin in cup 136*d*.

Figure 8G:
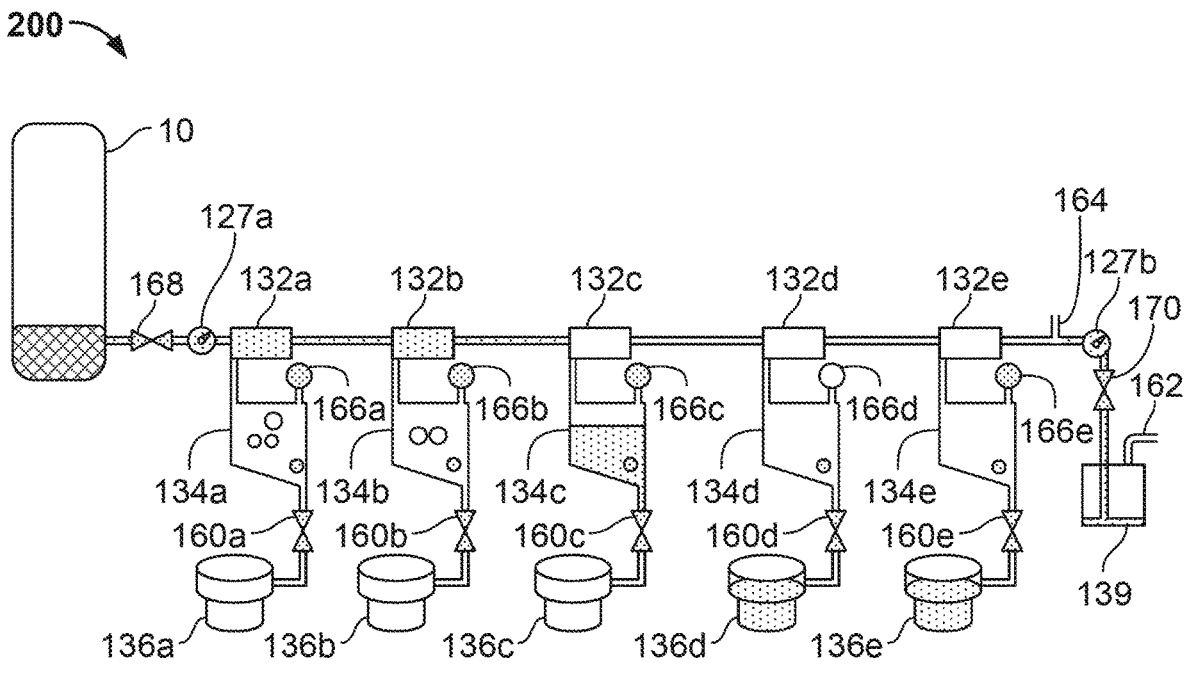

Referring to FIG. 8G, the measuring chambers 132*a-b* are still filled with blood, the cups 136*d-e* are still filled with blood/reagent mixture, and the blood that was in the measuring chamber 132*c* (refer to FIG. 8F) has transferred to the mixing chamber 134*c*. To arrive at this state, the following changes were made (in comparison to FIG. 8F) and/or the following conditions existed: (i) the valves 168 and 170 remained closed, (ii) the valve 160*d* was closed, (iii) the valves 160*a-c* and 160*e* remained closed, (iv) the vent 166*c* was opened (iv) the vents 166*a-b* and 166*d-e* remained closed, and (v) a source of air pressure was applied to the pressure application port 164. In embodiments comprising a stop junction between the measuring chamber 132*c* and the mixing chamber 134*c*, the, blood travels through the stop junction by application of pressure differential between the measuring chamber 132*c* and the mixing chamber 134*c*, while the stop junctions between the measuring chambers 132*a-b* and the mixing chambers 134*a-b* prevent flow. Accordingly, the blood flowed: (i) out of the measuring chamber 132*c*, and (ii) into the mixing chamber 134*c*. Because the vents 166*a-b* and because the valves 160*a-b* remained closed, the blood did not flow from the measuring chambers 132*a-b* towards the mixing chambers 134*a-b*. With blood in the mixing chamber 134*c*, the mixing element in mixing chamber 134*c* can agitate the blood to facilitate the dissolving of the reagent beads therein.

Figure 8H:
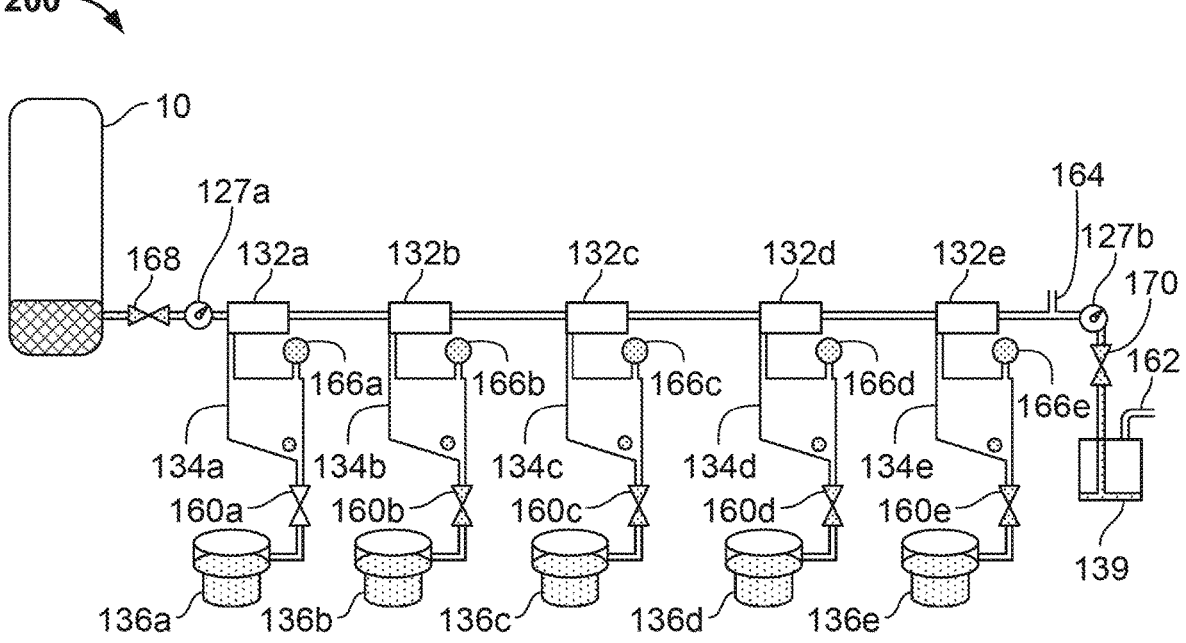

Referring to FIG. 8H, the completion of the process 200 is depicted. That is, the cups 136*a-c* all contain blood/reagent mixtures and rotary thromboelastometry can be taking place in the cups 136*a-e*. This state can be attained in accordance with the method of actuating the valves 168, 170, and 160*a-e*, and the vents 166*a-e*, in conjunction with applying vacuum to the vacuum application port 162 or pressure to the pressure application port 164 as described above.

Figure 9:
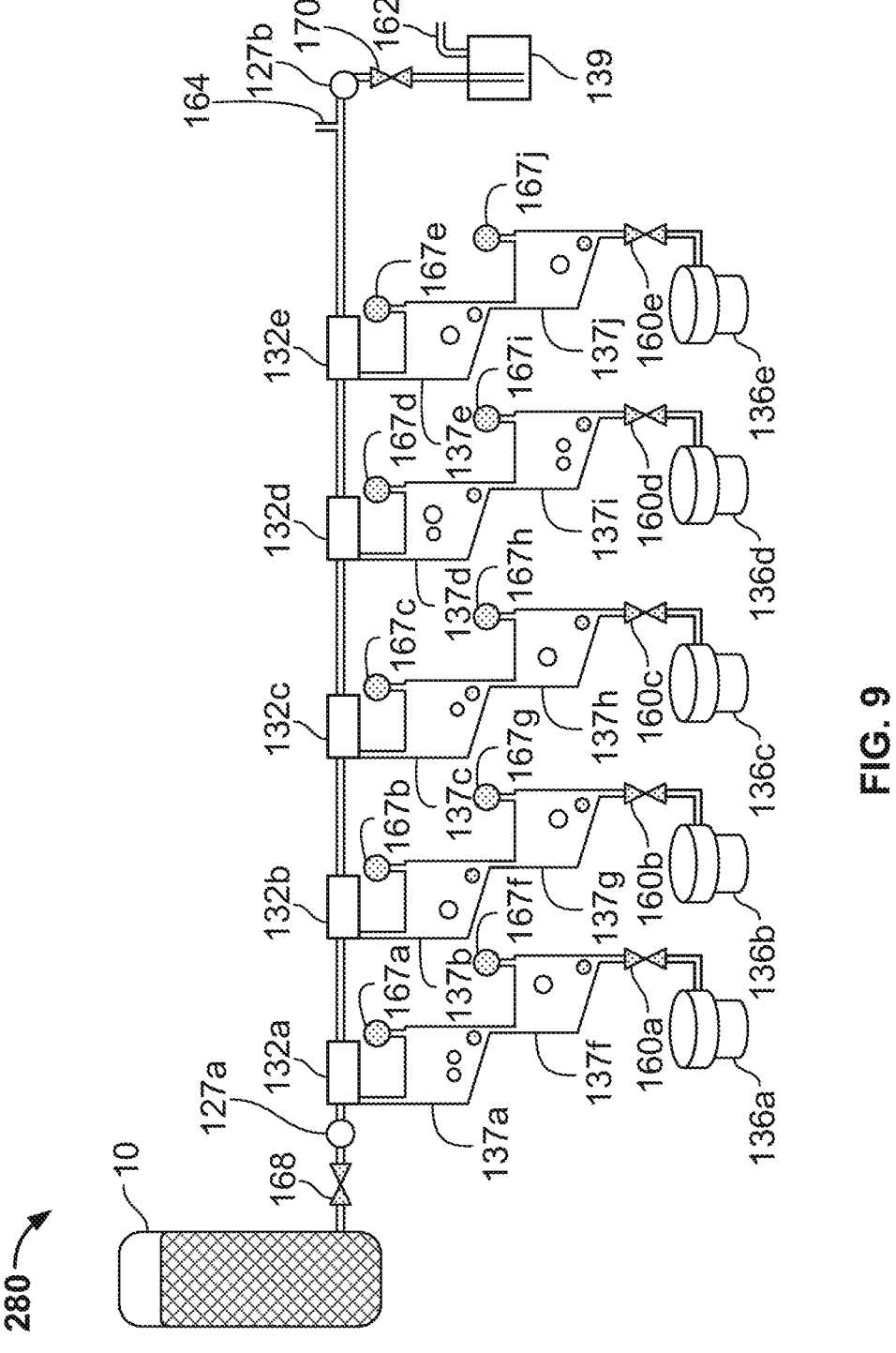
FIG. 9 is a schematic diagram of another example thromboelastometry system, in accordance with some embodiments.

Referring to FIG. 9, in some alternative embodiments, one or more of the individual blood flow channels or paths can include multiple mixing chambers that are arranged in series. For example, the example fluidic control process 280 includes five blood flow channels (similar to the number of channels in the embodiment of FIGS. 8A-H), but each of the channels include two mixing chambers that are arranged in series (rather than a single mixing chamber for each respective mixing chamber like the embodiment of FIGS. 8A-H). That is, mixing chambers 137*a* and 137*f* are arranged in series between the measurement chamber 132*a* and the cup 136*a*; mixing chambers 137*b* and 137*g* are arranged in series between the measurement chamber 132*b* and the cup 136*b*; mixing chambers 137*c* and 137*h* are arranged in series between the measurement chamber 132*c* and the cup 136*c*; mixing chambers 137*d* and 137*i* are arranged in series between the measurement chamber 132*d* and the cup 136*d*; and mixing chambers 137*e* and 137*j* are arranged in series between the measurement chamber 132*e* and the cup 136*e*.

In some embodiments, the reagent bead carrying the CaCl$_2$ reagent is separated from the other the reagent beads by locating the CaCl$_2$ reagent in the second of the two mixing chambers that are arranged in series. In that manner, the serial mixing chambers can allow the blood sample to be mixed with reagents and subsequently, at a controlled point in time, activation/clotting of the blood sample can be initiated.

While the example fluidic control process 280 includes five blood flow channels that each include two mixing chambers that are arranged in series, it should be understood that such a configuration is not required in all embodiments. For example, in some embodiments only a single blood flow channel that includes two mixing chambers that are arranged in series is included in a cartridge. Such a single blood flow channel with two mixing chambers may be the only blood flow channel in the cartridge, or may be combined in a cartridge with one or more other blood flow channels that include a single mixing chamber. It should be understood that all combinations and permutations of number of blood flow channels and mixing chambers are included within the scope of this disclosure.

Turning now to the blood coagulation testing chambers 136*a-e* in more detail, the chambers 136*a-e* can be configured to provide viscoelastic testing on the blood sample portion drawn into each chamber. Referring to FIGS. 10A and 10B, the pins 138*a-e* are located in the cartridge 120. A representative example showing the pin 138*b* located in the cup 136*b* illustrates that a clearance space exists between the outer diameter of the pin 138*b* and the inner diameter of the cup 136*b*. A blood/reagent mixture will at least partially fill the clearance space when rotary thromboelastometry is being performed therein. The pin 138*b* has a shoulder 138*bs*. The clearance space between the outer diameter of the pin 138*b* and the inner diameter of the cup 136*b* is less in the areas below the shoulder 138*bs* than in the areas above the shoulder 138*bs*. The areas between the outer diameter of the pin 138*b* and the inner diameter of the cup 136*b* that are below the shoulder 138*bs* are the areas that are active in regard to performing rotary thromboelastometry.

The cup 136*b* and pin 138*b* are shown in cross-section in FIG. 10B (in accordance with section 10B-10B of FIG. 10A). In addition, a sample inlet port 136*bi* (located behind pin 138*b* in the orientation of FIG. 10B) is provided so that the blood/reagent mixture will flow into the cup 136*b* via the sample inlet port 136*bi*. In the depicted embodiment, the cup inlet port 136*bi* is located in a sidewall of cup 136*b* at a height above the widened distal portion (refer to shoulder 138*bs*) of the pin 138*b* but below the proximal end of the pin 138*b* (refer to end near the entry to the axial bore 138*bb* of the pin 138*b*). In this configuration, the blood/reagent mixture will flow into the cup 136*b* so as to reduce the potential for bubble formation. In addition, locating the cup inlet port 136*bi* near the top of cup 136*b* eliminates the effects that the cup inlet port 136*bi* may otherwise have on the thromboelastometry measurements performed in the cup 136*b* if the cup inlet port 136*bi* is located in the active space between the inner diameter of the cup 136*b* and the outer diameter of the pin 138*b* below the shoulder 138*bs*.

In certain devices, bridging or other structure formation between the cup inlet port 136*bi* (in the interior diameter of the cup 136*b*) and the outer diameter of the pin 138*b* (i.e., the probe element) may occur. This may affect the ability of blood to flow into the cup 136*a-e*, or may cause error in the thromboelastometry measurements taken in the cup 136*a-e*. In some embodiments, the opening of the inlet port 136*bi* and the outer diameter of the pin 138*b* are at least a minimum clearance distance apart that prevents stable bridging of the blood sample or other coagulation structure formation between the pin 138*b* and the cup inlet port 136*bi*. At the minimum clearance distance, bridging between the sample inlet port and the pin may still occur upon filling the testing chamber, however, the bridge will not be stable enough to persist during measurement. Typically, a bridge will form around a bubble, which will be instable if the diameter is equal to or greater than the minimum clearance distance. In some embodiments, a stable bridge is one that lasts longer than 1 second, 2 seconds, 3 seconds, 4 seconds, or 5 seconds. In some embodiments, the minimum clearance distance is at least 1.5 mm. In some embodiments, the minimum clearance distance is at least 1.5 mm, 2 mm, 2.5 mm, or 3 mm. In the depicted embodiment in FIG. 10B, the cup inlet port 136*bi* is located in a sidewall of cup 136*b* at a height above the widened distal portion (refer to shoulder 138*bs*) of the pin 138*b* but below the proximal end of the pin 138*b* (refer to end near the entry to the axial bore 138*bb* of the pin 138*b*), and the inlet port 136*bi* is at least 1.5 mm from the pin 138*b*. In other words, the geometry of the pin can allow for this additional clearance since the pin has a narrower portion at the location at which the bridging might occur, thereby allowing for a greater clearance between the pin and the cup to prevent stable bridging.

In the depicted embodiment, the top of the cartridge 124 includes a vent 121. The vent 121 is in fluid communication with the needle 123*b*. Therefore, when air for venting a blood sample tube located in sample well 122 is needed, air is drawn through the vent 121 and channeled into the blood sample tube via the needle 123*b*.

Each of the pins 138*a-e* includes an axial bore. For example, the pin 138*b* includes an axial bore 138*bb*. The axial bore 138*bb* can be used to engage with a shaft (not shown in FIG. 10B) for performing rotary thromboelastometry.

Referring to FIG. 10C, an example rotary thromboelastometry assembly 300*b* can engage with the pin 138*b* to perform rotary thromboelastometry on a blood sample contained in the cup 136*b*. In this particular embodiment, the example rotary thromboelastometry assembly 300*b* includes a baseplate 302, a shaft 310*b*, a bearing 312*b*, a mirror 314*b*, a counterforce spring 320*b*, a light source 330*b*, and a detector 340*b* (e.g., a charge-coupled device or the like). The baseplate 302 can be lowered, as represented by arrows 318*b*, such that a tip portion of the shaft 310*b* enters the bore 138*bb* to become releasably coupled with the pin 138*b*. The bearing 312*b* is engaged with the baseplate 302 and the shaft 310*b* to facilitate rotational movement of the shaft 310*b* in relation to the baseplate 302. The counterforce spring 320*b* is coupled to the shaft 310*b* and oscillation of the spring 320*b* can induce the shaft 310*b* to oscillate back and forth by about +/−5° as represented by arrow 316*b*. The mirror 315 is coupled to the shaft 310*b*. The light source 330*b* is configured to project light towards the mirror 314*b*, and light can be reflected from the mirror 315 towards the detector 340*b* (depending on the rotational orientation of the shaft 310*b*). Accordingly, the motion of the pin 138*b* is detected by an optical detection system. It should be understood that other configurations of the rotary thromboelastometry assembly 300*b* are also envisioned within the scope of this disclosure.

The detected motion data is analyzed by an algorithm running on the analyzer console 140 (refer to FIGS. 1-3) to process and determine the thromboelastometry results. This system facilitates various thromboelastometry parameters such as, but not limited to, clotting time, clot formation time, alpha angle, amplitude, maximum clot firmness, lysis onset time, lysis time, lysis index (%), and maximum lysis (%).

As the blood in the cup 136*b* begins to coagulate, the motion amplitude of the shaft 310*b* starts to decrease (as detected by the deflection of the light beam from mirror 315 towards the detector 340*b*). During coagulation, the blood's fibrin backbone (together with platelets) creates a mechanical elastic linkage between the surfaces of the cup 136*b* and the pin 138*b*. A proceeding coagulation process induced by adding one or more of the aforementioned activating factors can thus be observed and quantified. In this way, various deficiencies of a patient's hemostatic status can be revealed and can be interpreted for proper medical intervention. At the end of the test process, the baseplate 302 can rise to uncouple the shaft 310*b* from the pin 138*b*.

Figure 11:
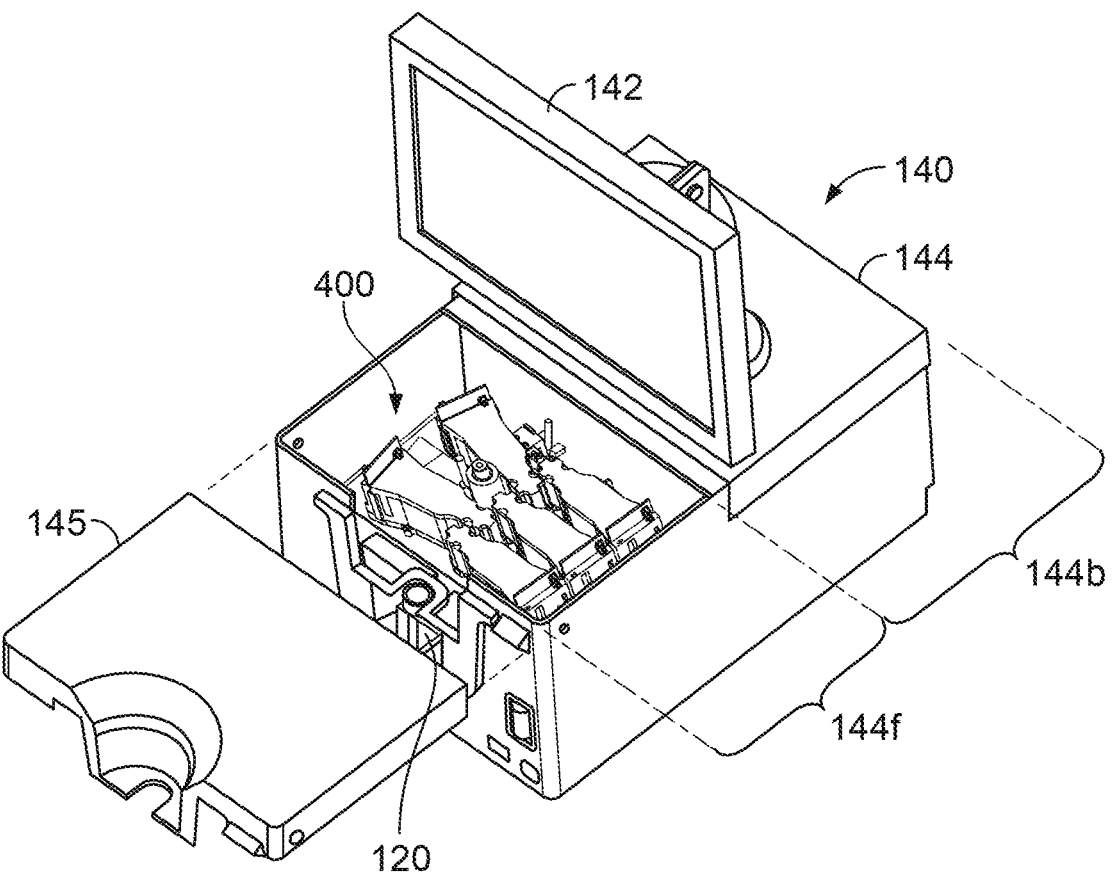
FIG. 11 is an exploded perspective view of a thromboelastometry analyzer console of the thromboelastometry system of FIGS. 1A, 1B, 2, and 3.

Referring to FIG. 11, the main chassis 144 of the analyzer console 140 can include a front portion 144*f* and a rear portion 144*b*. In some embodiments, the rear portion 144*b* houses at least some of the computer and electronic components that are necessary for the operations of the analyzer console 140. For example, the rear portion 144*b* can house hardware devices and software such as, but not limited to, computer processors, memory devices, an operating system and other executable instructions, power source(s), user interface controls, communication devices, circuit boards, and the like.

In the depicted embodiment, the front portion 144*f* includes a cover 145 and a sample handler assembly 400. The sample handler assembly 400 defines an interior space in which the cartridge 120 can be received. In some embodiments, the sample handler assembly 400 is a modular sub-assembly of the analyzer console 140, and the sample handler assembly 400 can be readily removed from the analyzer console 140 for service. The sample handler assembly 400 is electrically interconnected with the computer and electronic components that are housed in the rear portion 144*b*. As such, the analyzer console 140 can perform rotary thromboelastometry on a blood sample located in cartridge 120 and display the results on the touchscreen display 142.

Figure 12:
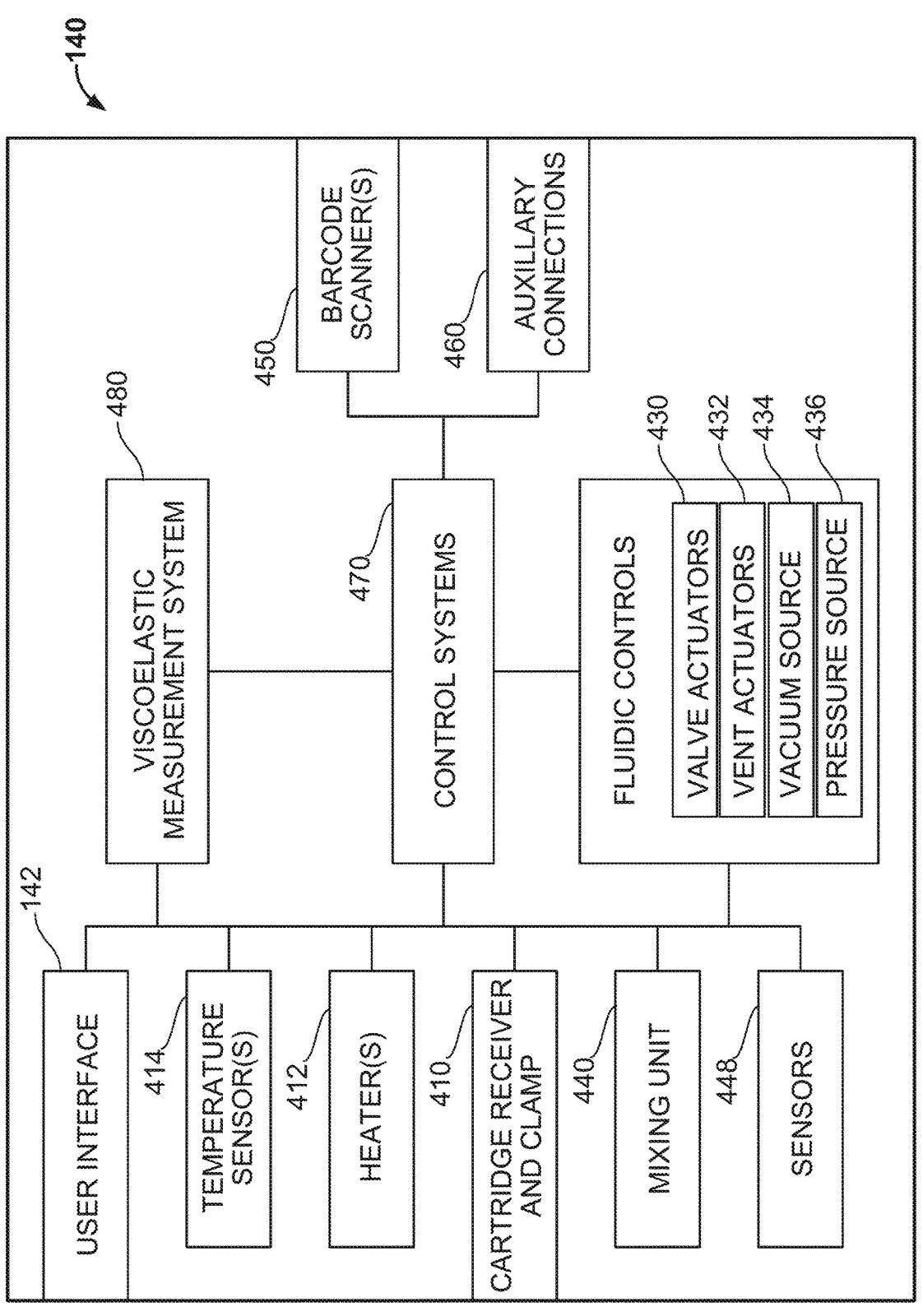
FIG. 12 is a block diagram that schematically depicts subsystems of the thromboelastometry analyzer console of the thromboelastometry system of FIGS. 1A, 1B, 2, and 3.

Referring now to FIGS. 11 and 12, the analyzer console 140 can include a cartridge receiver and clamp 410 and a viscoelastic measurement system 480. A mechanical frame assembly is used to support the cartridge receiver and clamp 410 and the viscoelastic measurement system 480 in orientations such that the cartridge receiver and clamp 410 and the viscoelastic measurement system 480 can function symbiotically.

Portions of the cartridge receiver and clamp 410 and the viscoelastic measurement system 480 are moveable in relation to the mechanical frame assembly (which is stationary in relation to the analyzer console 140). For example, the viscoelastic measurement system 480 can move upward and downward. As will be described further below, the viscoelastic measurement system 480 can move downward to engage with the cartridge 120 (e.g., refer to FIG. 11), and upward to disengage from the cartridge 120. A portion of the cartridge receiver and clamp 410 can move horizontally in relation to the mechanical frame assembly. As will be described further below, a portion of the cartridge receiver and clamp 410 can move horizontally to clamp or unclamp the cartridge 120 within the sample handler assembly 400.

In some embodiments, the cartridge receiver and clamp 410 includes a movable block sub-assembly and a stationary block sub-assembly. A space exists between the movable block sub-assembly and the stationary block sub-assembly in which the cartridge 120 can be received. The movable block sub-assembly can be translated towards or away from the stationary block sub-assembly. Accordingly, the cartridge 120 can be clamped and unclamped between the movable block sub-assembly and the stationary block sub-assembly by virtue of the relative movement therebetween. In some embodiments, the viscoelastic measurement system 480 is mounted to the movable block sub-assembly. Therefore, as the movable block sub-assembly is translated, the viscoelastic measurement system 480 is also translated.

In some embodiments, the moveable block sub-assembly can be translated by an electric motor. In particular embodiments, the motor is a stepper motor. In some embodiments, a gear reducer is coupled to the motor. Using a belt and pulley arrangement for compactness, the motor can be used to drive a lead screw. The threads of the lead screw can be engaged with complementary threads of the movable block such that a rotation of the lead screw results in horizontal translation of the movable block. In some embodiments, end-of-travel detectors (e.g., proximity sensors, optical sensors, micro-switches, and the like) are included to detect when the moveable block sub-assembly has been horizontally translated to the desired end-of-travel positions.

In some embodiments, one or more springs can extend between the movable moveable block sub-assembly and the stationary block sub-assembly. The springs can help facilitate a suitable clamping force between the movable block sub-assembly and the stationary block sub-assembly. In some embodiments, the springs are adjustable.

In some embodiments, portions of the moveable block sub-assembly and the stationary block sub-assembly that make contact with the cartridge 120 comprise a flexible or compressible material so that while the cartridge 120 is clamped it is also protected from damage.

In particular embodiments, the moveable block sub-assembly can include one or more features on the clamping face of the moveable block sub-assembly that serve to position the cartridge 120 in the desired location within the sample handler assembly 400. For example, in some embodiments the moveable block sub-assembly includes two locator pins that can mate with the locator pin receptacles 140*a* and 140*b* of the cartridge 120 (refer to FIG. 7) to accurately position the cartridge 120 in relation to the sample handler assembly 400.

In some embodiments, one or both of the moveable block sub-assembly and the stationary block sub-assembly include heating devices 412 that can warm the cartridge 120 when the cartridge 120 is clamped therebetween. For example, in some embodiments the heaters 412 are electrical resistance heaters that are used to heat at least portions of the cartridge 120. In some embodiments, the heaters 412 are configured to facilitate warming of individual portions of the cartridge 120 independently from other portions of the cartridge 120. For example, one or more of the individual blood flow channels 130*a*, 130*b*, 130*c*, 130*d*, and 130*e* (refer to FIGS. 4-7) can be independently warmed in some such embodiments. Warming may be performed to one or more sides of the cartridge 120. Other types of warming modalities may be used including, but not limited to, IR, ultrasonic, microwave, and the like.

In particular embodiments, one or more temperature sensors 414 are included that can detect the temperature of the cartridge 120 at one or more locations on the cartridge 120. For example, in some embodiments the one or more temperature sensors 414 can be thermocouples, thermistors, infra-red temperature sensors, and the like. Accordingly, the analyzer console 140 can control the heating of the cartridge 120 to a predetermined temperature (e.g., about 37° C.) using the heaters 412 and the temperature sensors 414.

The moveable block sub-assembly can include multiple solenoids that are used to actuate the aforementioned vents and valves of the cartridge 120. For example (referring also to FIG. 7), the valves 168, 170, and 160 *a-e*, can be actuated by valve actuators 430 and the vents 166*a-e* can be actuated by vent actuators 432. In some embodiments, the valve actuators 430 and the vent actuators 432 comprise solenoids. Actuation of the valves 168, 170, and 160 *a-e* by the valve actuators 430 can be accomplished by coupling pins to the valve actuators 430 that are extendable from the moveable block sub-assembly to make contact with and to distend valve elastomer members so that the elastomer members make contact with a valve seat within the cartridge 120. Actuation of the vents 166*a-e* by the vent actuators 432 can be accomplished by coupling pins with resilient tips that are extendable from the moveable block sub-assembly to obstruct the vents 166 *a-e*. Such pins with resilient tips can act as stoppers to substantially prevent airflow through the vents 166*a-e*. In some embodiments, the valve actuators 430 and the vent actuators 432 comprise solenoids that include internal springs that cause the valve actuators 430 and the vent actuators 432 to be normally extended (e.g., when the electrical power is removed from the solenoids). Accordingly, such normally closed solenoids will close the vents and valves of the cartridge 120 as a default configuration.

The sample handler assembly 400 also includes pressure source 436 and vacuum source 434 by which air pressure and vacuum can be applied to the pressure application port 164 and the vacuum application port 162 of cartridge 120 respectively (refer to FIG. 7). For example, the pressure source 436 and vacuum source 434 can make contact with the cartridge 120 and can convey pressure or vacuum to the pressure application port 164 and the vacuum application port 162 when the cartridge 120 is clamped within the cartridge receiver and clamp 410. The pressure source 436 and vacuum source 434 are at least partially made of a resilient material in some embodiments. For example, in some embodiments the pressure source 436 and vacuum source 434 are at least partially made of a resilient material such as, but not limited to, silicone, butyl rubber, nitrile rubber, ethylene propylene rubber, fluoroelastomers, and the like. One or more internally-housed pressure and/or vacuum pumps (not shown) can also be included in the analyzer console 140. Such internally-housed pressure and vacuum pumps can be used to generate the air pressure or vacuum that is applied to the cartridge 120 to induce the transport of blood within the cartridge 120 as described above in reference to FIGS. 8A-8H.

As previously described, the cartridge receiver and clamp 410 also includes the stationary block sub-assembly. In some embodiments, the stationary block sub-assembly does not move in relation to the mechanical frame assembly and in relation to the analyzer console 140 as a whole.

In some embodiments, the analyzer console 140 includes a mixing unit 440. In particular embodiments, the mixing unit 440 includes a motor, a crank and connecting rod assembly, and a magnet shuttle. These components can be used to magnetically couple with the mixing elements of the cartridge 120 and to induce movement of the mixing elements within the mixing chambers 134*a-e*. The movement of the mixing elements encourages the reagent beads to dissolve in the blood contained within the mixing chambers 134*a-e* as described above.

The analyzer console 140 can also include one or more sensors 448. The one or more sensors 448 can be used to detect the presence of blood in particular locations within the cartridge 120, such as blood detection locations 127*a* and 127*b* as described above (refer to FIG. 5). In some embodiments, the sensors 448 are optical sensors, such as IR (infrared) sensors. In some embodiments, the sensors 448 can be used to detect blood in other areas of the cartridge 120, such as, but not limited to, in the cups 136*a-e* (refer to FIGS. 8A-8H).

The sample handler assembly 400 of the analyzer console 140 also includes the viscoelastic measurement system 480. The viscoelastic measurement system 480 includes the baseplate 302 (e.g., refer to FIG. 10C), one or more thromboelastometry assemblies (e.g., thromboelastometry assembly 300*b*), and a linear actuator assembly. The one or more thromboelastometry assemblies can each be affixed to the baseplate 302. In some embodiments, the linear actuator assembly can be coupled to the baseplate 302 and to the cartridge receiver and clamp 410. Accordingly, actuation of the linear actuator assembly can translate the baseplate 302 and the cartridge receiver and clamp 410 towards each other or away from each other. A linear bearing assembly of the linear actuator can guide the baseplate 302 in a linear path, and stabilize the baseplate 302, as the baseplate 302 translates towards or away from the cartridge receiver and clamp 410.

In some embodiments, the linear actuator assembly causes the baseplate 302 to vertically raise or lower in relation to the cartridge receiver and clamp 410 using a motor (e.g., a DC motor or a stepper motor) that rotates a lead screw that has threads that are engaged with a drive nut. The drive nut is coupled to the baseplate 302. In some embodiments, end-of-travel detectors (e.g., proximity sensors, optical sensors, micro-switches, and the like) are included to detect when the baseplate 302 has been vertically translated to the desired end-of-travel positions.

The viscoelastic measurement system 480 includes one of more rotary thromboelastometry assemblies (e.g., rotary thromboelastometry assembly 300b of FIG. 10C) that include a shaft configured to couple with a pin (e.g., the shaft 310b configured to couple with the pin 138b). Because the thromboelastometry assemblies are mounted to the baseplate 302, the shafts are raised or lowered in conjunction with the raising or lowering of the baseplate 302. Accordingly, actuation of the linear actuator assembly causes the shafts to vertically raise or lower in relation to the cartridge receiver and clamp 410, and in relation to a cartridge 120 when a cartridge 120 is clamped within the cartridge receiver and clamp 410. Therefore, from the description herein it can be understood that actuation of the linear actuator assembly can engage and disengage the shafts from the pins of the cartridge 120 (e.g., refer to FIG. 10C that shows baseplate 302 being lowered to engage shaft 310b with pin 138b).

In addition to the aforementioned features of the analyzer console 140, in some embodiments the analyzer console 140 also includes one or more of the following features. The analyzer console 140 can include one or more barcode scanners 450 that, for example, can read a barcode at the barcode location 125 on the leading end of cartridge 120 (refer to FIG. 5). In some embodiments, the analyzer console 140 can include one or more devices to detect the presence of the cartridge 120 in a desired insertion location and/or orientation. For example, in some embodiments one or more micro switches can be used to detect when the cartridge 120 has been inserted in a desired location and orientation within the sample handler assembly 400. In some embodiments, the analyzer console 140 can include one or more auxiliary connections 460. The auxiliary connections 460 can include network and device connectors such as, but not limited to, one or more USB ports, Ethernet ports (e.g., RJ45), VGA connectors, Sub-D9 connectors (RS232), and the like. Such auxiliary connections 460 can be located on the rear of the main chassis 144, or at other convenient locations on the main chassis 144. For example, in some embodiments one or more USB ports may be located on or near the front of the main chassis 144.

The analyzer console 140 also includes a user interface 142 (e.g., with a touchscreen display in this embodiment). In the depicted embodiment, the user interface 142 is configured to receive user input and to display output information to the user. For example, the user can enter information to the analyzer console 140 by making selections of various soft-buttons that may be displayed on the user interface 142 at times during the beginning, middle, and end of the testing process. In some embodiments, other selections such as, but not limited to, soft keyboard entries can be provided via user interface 142. In some embodiments, data entry can be performed additionally or alternatively by voice entry. In some embodiments, the user interface may include other peripheral devices (e.g., a mouse, a keyboard, an additional display device, and the like) as part of the analyzer console 140. In some embodiments, a computer data network (e.g., intranet, internet, LAN, etc.) may be used to allow for remote devices to receive and/or input information from the system 100. For example, in some embodiments one or more remote displays can be utilized via auxiliary connections 460. In the depicted embodiment, the user interface 142 also includes an external barcode reader 146 (refer to FIG. 1A). Alternatively or additionally, the user interface 142 of the analyzer console 140 can be equipped with a reader configured to read near-field communication tags, RFID tags, or the like. The analyzer console 140 can also include one or more control systems 470 that can execute instructions embodied in a computer program. The control systems 470 can include, by way of example, both general and special purpose microprocessors, and any one or more processors of any kind of digital computer. In some embodiments, the control systems 470 includes one or more such processors, memory, storage devices, interfaces, and other types of electronic sub-systems and components. Such components may be mounted on a common motherboard or in other manners as appropriate. The control systems 470 can process instructions for execution within the analyzer console 140, including instructions stored in the memory or on the storage device. In some implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The storage devices are capable of providing mass storage for the control systems 470. In some implementations, the storage device may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above in reference to FIGS. 8A-8H. The computer program product can also be tangibly embodied in a computer- or machine-readable medium, such as the memory, the storage device, or memory on the processor(s).

Figure 13:
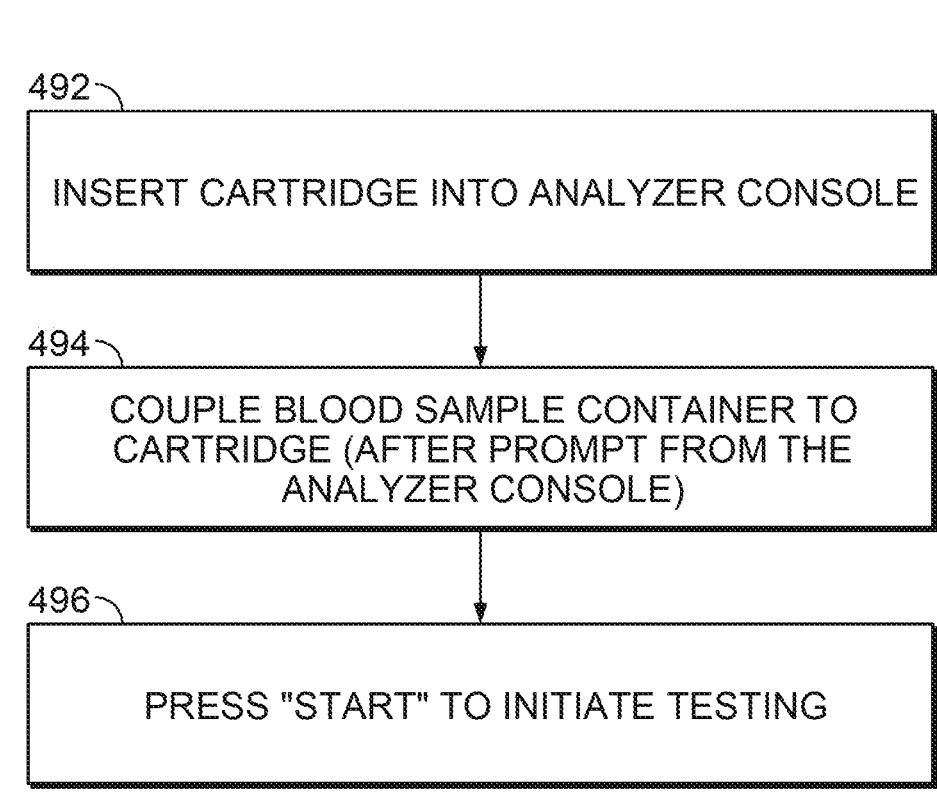
FIG. 13 is a flowchart of a method of using a thromboelastometry system, in accordance with some embodiments.

Referring to FIG. 13, in some implementations a user can interact with the thromboelastometry systems provided herein according to an example process 490. In step 492, the user can insert a cartridge into an analyzer console. In some examples, at least a portion of the cartridge remains exposed while other portions of the cartridge are concealed within the analyzer console. For example, this step is exemplified above in reference to FIG. 1A. In step 494, the user can couple a blood sample container to the cartridge after a prompt is received from the analyzer console. Step 494 can be performed while the cartridge remains inserted in the analyzer console as defined by step 492. At step 496, the user can press a "start" button (or equivalent) to initiate an automated transport of blood in the blood sample reservoir to the blood testing chambers of the cartridge such that the viscoelastic characteristics of the blood can be measured. In some examples, the analyzer console provides an indication that the testing is ready to be initiated, but that indication is not required as part of process 490.

Figure 14A:
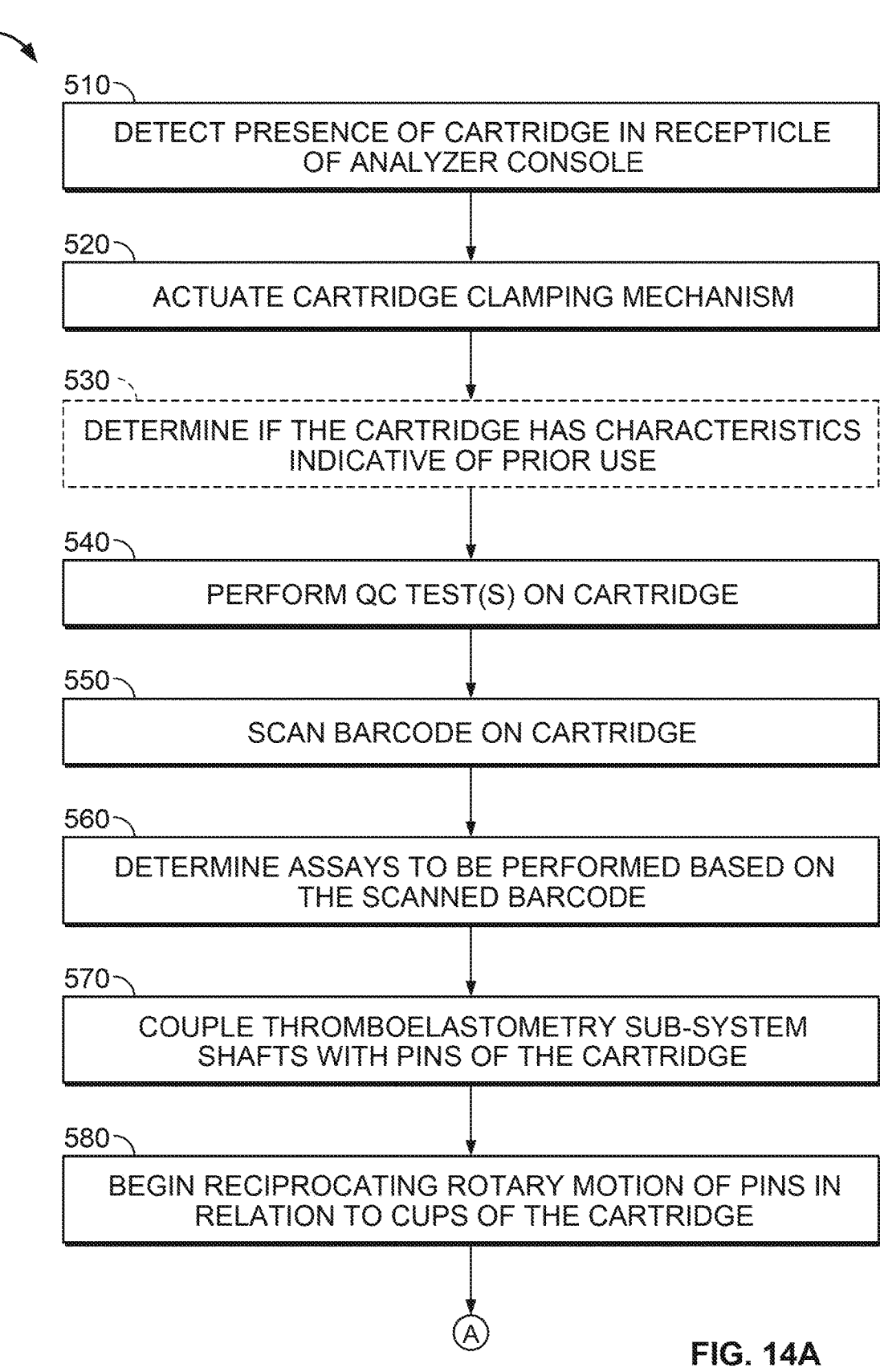

Referring to FIGS. 14A and 14B, in some implementations a thromboelastometry system can perform thromboelastometry according to an example process 500. The individual steps of the process 500 may not necessarily be performed in the order listed. Further, in some implementations some steps of the process 500 may be performed in parallel. The process 500 may be performed by the thromboelastometry systems described above, such as thromboelastometry system 100.

In step 510, the presence of a cartridge is detected in a receptacle of an analyzer console of the thromboelastometry system. For example, the detection may be performed by a micro switch, optical sensor, barcode scanner, and the like, or a combination thereof. Even though the cartridge is detected in the receptacle, at least a portion of the cartridge may be exterior to the analyzer console.

In step 520, the analyzer console actuates a clamping mechanism to clamp the cartridge at least partially in the analyzer console. For example, the cartridge receiver and clamp 410 as described above can be activated to clamp the cartridge.

In step 530, the analyzer console can optionally determine if the cartridge has characteristics that indicate the cartridge has been used previously. For example, the analyzer console may use optical sensors to inspect for the presence of blood in the cartridge. In some embodiments, if one or more characteristics that indicate the cartridge has been used previously are detected, the analyzer console may suspend further steps of process 500 and provide a pertinent message via the user interface.

In step 540, the analyzer console can perform one or more QC tests to test the integrity of the cartridge. For example, in some embodiments the cartridge can be tested for leaks such as by performing a pressure/vacuum decay test.

In step 550, the analyzer console scans the cartridge for a barcode. For example, the analyzer console may scan a leading end of the cartridge at which a 1D or 2D barcode may be present.

In step 560, the analyzer console determined the types of thromboelastometry assays to be performed based on the information attained from the scan of the barcode in step 550.

In step 570, the shafts of the thromboelastometry subsystem of the analyzer console are coupled with pins of the cartridge. The pins are located in cups of the cartridge. Accordingly, the coupling of the shafts of the thromboelastometry sub-system to the pins can configure the thromboelastometry system to be capable of performing thromboelastometry on a blood sample contained within the cups of the cartridge. For example, referring to FIG. 10C, the shaft 310b of the thromboelastometry assembly 300b can be lowered towards the cartridge so that the shafts 310b become friction-fit and releasably coupled with the pins 138b of the cartridge 120.

In step 580, the analyzer console can begin rotatory reciprocation of the pins in relation to the cups of the cartridge. For example, this step is exemplified above in reference to FIG. 10C.

In step 590, the analyzer console can heat the cartridge. In some implementations, the analyzer console may heat the cartridge to a predetermined temperature. In particular implementations, the analyzer console may maintain the cartridge at the predetermined temperature. For example, in some implementations the predetermined temperature may be about 35° C. to about 40° C., and preferably about 37° C.

In step 600, the analyzer console provides a prompt to couple a blood sample container to the cartridge. This prompt may be provided, for example upon the successful completion of one or more steps, or upon the successful verification of one or more conditions, or both. For example, this prompt may be provided upon the cartridge's successful attainment of the predetermined temperature as per step 590, among other things. The prompt may be provided via the user interface of the analyzer console. For example, the prompt may be a visual message displayed on a touchscreen monitor of the analyzer console. An audible prompt may be provided in some implementations.

In step 610, the analyzer console may optionally detect the presence of blood in the cartridge. Such detection may be performed, for example, using one or more IR sensors of the analyzer console. The detection of blood in the cartridge in this step can indicate that a blood sample container was successfully coupled to the cartridge.

In step 620, the analyzer console can provide a prompt to "start" testing. In some implementations, the prompt to "start" testing may be provided on the basis of the successful completion of one or more steps, or upon the successful verification of one or more conditions, or both. The prompt may be provided via the user interface of the analyzer console. For example, the prompt may be a visual message displayed on a touchscreen monitor of the analyzer console. In some embodiments, the touchscreen can receive a user input to start the testing.

In step 630, the analyzer console can cause blood to flow from the sample container into the cartridge. In some implementations, a vacuum source of the analyzer console is used to cause blood flow into the cartridge. In some implementations, an air pressure source of the analyzer console is used to cause blood flow into the cartridge. The analyzer console may also actuate various valves or vents to control the blood flow within the cartridge (e.g., refer to FIGS. 8A-8H).

In step 640, the analyzer console can induce agitation to assist with the dissolving of reagents in the blood contained within the cartridge. This step is exemplified above in regard to the horizontal reciprocation of the magnet shuttle with its one or more magnets that are magnetically coupled with mixing elements of the cartridge 120, causes movement of the mixing elements within the cartridge 120 to encourage the reagent beads to dissolve in the blood contained within the mixing chambers 134a-e.

In step 650, thromboelastometry testing is started. For example, the analyzer console can begin to analyze the data produced the thromboelastometry assemblies in regard to the reciprocating rotation of the shafts that are coupled with the pins 138a-e located in the cups 136a-e of the cartridge (refer to FIGS. 8A-8H). In some implementations, the analyzer console may begin to analyze the data produced by some of the thromboelastometry assemblies prior to beginning to analyze the data produced by others of the thromboelastometry assemblies. For example, as described above in reference to FIGS. 8A-8H, the analyzer console may begin to first analyze the data produced by the thromboelastometry assembly pertaining to cup 136e. Subsequently, the analyzer console may begin to analyze the data produced by the thromboelastometry assembly pertaining to cup 136d, and so on.

In step 660, the analyzer console displays the results of the thromboelastometry. Such results may be displayed concurrently with the performance of the testing and at the completion of the testing. The results can be displayed via the user interface of the analyzer console, such as on the touchscreen display. The results can be displayed using qualitative graphical representations and quantitative parameters.

In step 670, the analyzer console can unclamp the cartridge at the cessation of the testing. In some cases, such cessation may be initiated by a user input to the analyzer console to stop the testing, or by the completion of the test assays, or by the expiration of a time-based parameter. The unclamping may be performed, for example, by the horizontal translation of the moveable block sub-assembly. After the unclamping, the cartridge can be removed from the analyzer console.

A number of embodiments of the invention have been described. Nevertheless, it will be understood that various modifications may be made without departing from the spirit and scope of the invention. Accordingly, other embodiments are within the scope of the following claims.

What is claimed is:

1. A cartridge for a measuring system, the cartridge comprising:
    a blood sample receiver configured to mate with a blood sample reservoir containing a blood sample;
    a first fluid channel in fluid communication with the blood sample receiver and configured to receive a first portion of a blood sample in a first measuring chamber;
    a second fluid channel in fluid communication with the blood sample receiver and configured to receive a second portion of the blood sample in a second measuring chamber;
    the first fluid channel comprising a first mixing chamber containing a first reagent, and a first testing chamber that enables measuring a viscoelastic characteristic of a first liquid that is based on a mixture of the first portion of the blood sample and the first reagent; and
    the second fluid channel comprising a second mixing chamber containing a second reagent, and a second testing chamber that enables measuring a viscoelastic characteristic of a second liquid that is based on a mixture of the second portion of the blood sample and the second reagent;
    wherein the cartridge further comprises a first port, a second port, and a third port each accessible at an exterior of the cartridge, the first port being in fluid communication with the first measuring chamber, the second port being in fluid communication with the first measuring chamber, and the third port being in fluid communication with the first measuring chamber, the first port, the second port, and the third port being different from the blood sample receiver; and
    wherein the cartridge further comprises an assembly attached adjacent to the first testing chamber, the assembly being configured to receive a part of the measuring system that enables measurement of the viscoelastic characteristic of the first liquid.

2. The system of claim 1, wherein blood flow from the first measuring chamber into the first mixing chamber is implemented by applying a pressure at the third port.

3. The system of claim 2, wherein liquid flow between the first mixing chamber and the first testing chamber is implemented by applying a pressure at the third port.

4. The cartridge of claim 1, wherein the first and second fluid channels are arranged in parallel such that the first fluid channel comprising the first mixing chamber and the first testing chamber is in parallel with the second fluid channel comprising the second mixing chamber and the second testing chamber; and
    wherein the second reagent in the second mixing chamber is different from the first reagent in the first mixing chamber.

5. The cartridge of claim 1, wherein the first and second reagents comprise reagent beads configured to dissolve in a respective first or second portion of the blood sample.

6. The cartridge of claim 1, wherein the first and second reagents comprise liquid reagent.

7. The cartridge of claim 1, wherein at least one of the first reagent or the second reagent comprises an activator of coagulation.

8. The cartridge of claim 1, wherein the first testing chamber is associated with a first probe configured to measure the viscoelastic characteristic of the first liquid following application of heat to at least part of the cartridge, and the second testing chamber is associated with a second probe configured to measure the viscoelastic characteristic of the second liquid following application of heat to at least part of the cartridge.

9. The cartridge of claim 1, wherein the first portion of the blood sample and the second portion of the blood sample are each portions of a same test sample of blood.

10. The cartridge of claim 1, wherein the first reagent comprises one or more reagents that are different from the second reagent.

11. The cartridge of claim 1, wherein, to add the first portion of the blood sample to the first measuring chamber, the first port is configured to be closed and the second port is configured to receive pressure.

12. A cartridge for a test system, the cartridge comprising:
    a blood sample receiver configured to mate with a blood sample reservoir containing a blood sample;
    fluid channels, where a fluid channel among the fluid channels comprises:
        a testing chamber for holding a liquid, the liquid comprising a combination of blood from the blood sample and reagent, the testing chamber enabling a test on the liquid;
        a measuring chamber for holding the blood from the blood sample;
        a mixing chamber for holding the reagent; and
        an assembly attached adjacent to the testing chamber, the assembly being configured to receive a part of the test system that enables the test on the liquid; and
    a first port, a second port, and a third port each accessible at an exterior of the cartridge, the first port being in fluid communication with the measuring chamber, the second port being in fluid communication with the measuring chamber, and the third port being in fluid communication with the measuring chamber, the first port, the second port, and the third port being different from the blood sample receiver.

13. The cartridge of claim 12, wherein at least part of the cartridge is at a predetermined temperature before blood flow into the measuring chamber is implemented.

14. The cartridge of claim 12, wherein blood flow from the measuring chamber into the mixing chamber is implemented by applying a pressure at the third port.

15. The cartridge of claim 12, wherein liquid flow between the mixing chamber and the testing chamber is implemented by applying a pressure at the third port.

16. The cartridge of claim 12, wherein the cartridge comprises N (N>1) measuring chambers including the measuring chamber, N mixing chambers including the mixing chamber, and N testing chambers including the testing chamber;
    wherein each $N^{th}$ testing chamber is for holding a liquid that is based on a mixture of blood from an $N^{th}$ measuring chamber and a reagent from an $N^{th}$ mixing chamber;
    wherein each $N^{th}$ testing chamber enables a viscoelastic test on the liquid received in the $N^{th}$ testing chamber; and wherein tests performed are for measuring one or more viscoelastic characteristics of the liquid received in the N$^{th}$ testing chamber.

17. The cartridge of claim 16, wherein at least two of the N mixing chambers contain different reagents.

18. The cartridge of claim 12, further comprising a needle for adding the blood to the cartridge.

19. The cartridge of claim 12, wherein the mixing chamber is configured to mix, at least partly, the reagent with the blood to produce the combination of blood and reagent.

20. The cartridge of claim 12, wherein the cartridge is configured so that changes in pressure in a fluid channel among the fluid channels cause the blood to flow to the mixing chamber and the liquid comprising the combination of blood and reagent to flow to the testing chamber.

21. The cartridge of claim 20, wherein the cartridge is configured for connection to a pump to implement the changes in pressure.

22. The cartridge of claim 12, wherein the mixing chamber holds multiple reagents.

23. The cartridge of claim 12, wherein the test is designed to measure, over time, changes in viscoelastic properties of the liquid.

24. The cartridge of claim 12, wherein the test is designed to be performed using a probe, at least part of the probe being external to the testing chamber.

25. The cartridge of claim 12, wherein the cartridge comprises four measuring chambers including the measuring chamber, four mixing chambers including the mixing chamber, and four testing chambers including the testing chamber;

wherein each testing chamber is for receiving a liquid that is based on a mixture of blood from a corresponding measuring chamber and a reagent from a corresponding mixing chamber; and wherein each testing chamber enables a test to be performed on the liquid received in the testing chamber.

26. The cartridge of claim 12, wherein, to add the blood to the measuring chamber, the first port is configured to be closed and the second port is configured to receive pressure.

27. The cartridge of claim 12, wherein the fluid channels comprise a first testing chamber for holding a first liquid comprising a combination of first blood and first reagent and a second testing chamber for holding a second liquid comprising a combination of second blood and second reagent;

wherein the first testing chamber is configured to enable a first test on the first liquid in the first testing chamber, the first test for measuring a first characteristic of the first liquid, and wherein the second testing chamber is configured to enable a second test on the second liquid in the second testing chamber, the second test for measuring a second characteristic of the second liquid, the first test being different from the second test.

28. The cartridge of claim 27, wherein the fluid channels are arranged in parallel.

29. The cartridge of claim 27, wherein the fluid channels comprise:

a first mixing chamber containing the first reagent and a second mixing chamber containing the second reagent.

30. The cartridge of claim 29, wherein the fluid channels comprise:

a first measuring chamber configured to receive the first blood, and a second measuring chamber configured to receive the second blood;

wherein the first measuring chamber is along a first fluid channel with the first mixing chamber and the first testing chamber and the second measuring chamber is along a second fluid channel with the second mixing chamber and the second testing chamber.

31. The cartridge of claim 12, wherein the reagent comprises an activator of coagulation.

32. The cartridge of claim 12, further comprising:

an interface to a control apparatus configured to initiate fluid flows through the fluid channels.

33. The cartridge of claim 27, wherein at least part of a first probe for performing the first test is external to the first testing chamber, and at least part of a second probe for performing the second test is external to the second testing chamber.

34. The cartridge of claim 27, wherein the first test relates to viscoelastic characteristics of the first liquid and the second test relates to viscoelastic characteristics of the second liquid.

* * * * *